United States Patent
Price et al.

(10) Patent No.: US 10,507,236 B2
(45) Date of Patent: Dec. 17, 2019

(54) CHIMERIC PROTEINS

(71) Applicants: Lipotek Pty Ltd, Acton, Australian Capital Territory (AU); The Australian National University, Acton, Australian Capital Territory (AU)

(72) Inventors: Jason David Price, Kaleen (AU); Christopher Parish, Campbell (AU); Ines Atmosukarto, Kingston (AU)

(73) Assignees: Lipotek Pty Ltd, Acton (AU); The Australian National University, Acton (AU)

( * ) Notice: Subject to any disclaimer, the term of this patent is extended or adjusted under 35 U.S.C. 154(b) by 0 days.

(21) Appl. No.: 15/518,119

(22) PCT Filed: Oct. 9, 2015

(86) PCT No.: PCT/AU2015/050614
§ 371 (c)(1),
(2) Date: Apr. 10, 2017

(87) PCT Pub. No.: WO2016/054696
PCT Pub. Date: Apr. 14, 2016

(65) Prior Publication Data
US 2018/0185464 A1 Jul. 5, 2018

(30) Foreign Application Priority Data
Oct. 9, 2014 (AU) ................................ 2014904028

(51) Int. Cl.
*A61K 39/02* (2006.01)
*A61K 39/112* (2006.01)
*A61K 39/12* (2006.01)
*A61K 39/295* (2006.01)
*A61K 39/00* (2006.01)
*C07K 14/255* (2006.01)
*A61K 9/127* (2006.01)
*C07K 14/245* (2006.01)

(52) U.S. Cl.
CPC ........ *A61K 39/0275* (2013.01); *A61K 9/1271* (2013.01); *A61K 39/00* (2013.01); *A61K 39/12* (2013.01); *A61K 39/295* (2013.01); *C07K 14/245* (2013.01); *C07K 14/255* (2013.01); *A61K 2039/523* (2013.01); *A61K 2039/55555* (2013.01); *A61K 2039/572* (2013.01); *A61K 2039/70* (2013.01); *C07K 2319/00* (2013.01); *C07K 2319/21* (2013.01); *C12N 2740/16034* (2013.01); *Y02A 50/476* (2018.01); *Y02A 50/482* (2018.01)

(58) Field of Classification Search
None
See application file for complete search history.

(56) References Cited

U.S. PATENT DOCUMENTS

| 6,130,082 A * | 10/2000 | Majarian | C07K 14/005 |
| | | | 435/252.3 |
| 2009/0011982 A1 | 1/2009 | Gudkov et al. | |

FOREIGN PATENT DOCUMENTS

| WO | WO 2006/081631 | 8/2006 |
| WO | WO 2007/103048 | 9/2007 |
| WO | WO 2008/097016 | 8/2008 |
| WO | WO 2009/087508 | 7/2009 |
| WO | WO 2009/156405 | 12/2009 |
| WO | WO 2010/050903 | 5/2010 |

OTHER PUBLICATIONS

Crampton et al Applied Microbio. and Biotech. Jun. 2007. 75(3): 599-607.*
Altin et al., "Synthesis of the chelator lipid nitrilotriacetic acid ditetradecylamine (NTA-DTDA) and its use with the IAsys biosensor to study receptor-ligand interactions on model membranes," Biochim Biophys Acta., Aug. 6, 2001;1513(2):131-48.
Banerjee et al., "Anisamide-targeted stealth liposomes: a potent carrier for targeting doxorubicin to human prostate cancer cells," Int J Cancer, Nov. 20, 2004;112(4):693-700.
Burdelya et al., "An agonist of toll-like receptor 5 has radioprotective activity in mouse and primate models," Science, Apr. 11, 2008;320(5873):226-30. doi: 10.1126/science.1154986.
Cuadros et al., "Flagellin fusion proteins as adjuvants or vaccines induce specific immune responses," Infection and Immunity, 72(5):2810-2816, 2004.
Kristen N. Delaney et al., "A Recombinant Flagellin-Poxvirus Fusion Protein Vaccine Elicits Complement-Dependent Protection Against Respiratory Challenge with Vaccinia Virus in Mice," Viral Immunology, 23(2):201-210, 2010.
Emmetiere et al., "(18)F-labeled-bioorthogonal liposomes for in vivo targeting," Bioconjug Chem., Nov. 20, 2013;24(11):1784-9. doi: 10.1021/bc400322h. Epub Nov. 7, 2013.
Ting-Ting Feng et al., "Expression and Identification of Immunological Activities of the HIV-gp120N-Human Interferon Gamma Fusion Protein," The Anatomical Record, 292(3):381-386, 2009.
Gregory et al., Vaccine delivery using nanoparticles, Front Cell Infect Microbiol., Mar. 25, 2013;3:13. doi: 10.3389/fcimb.2013. 00013.
Huleatt et al., "Potent immunogenicity and efficacy of a universal influenza vaccine candidate comprising a recombinant fusion protein linking influenza M2e to the TLR5 ligand flagellin," Vaccine, 26(2):201-214, 2007.
Marques-Gallego et al., "Ligation strategies for targeting liposomal nanocarriers," Biomed Res Int., 2014;2014:129458. doi: 10.1155/2014/129458. Epub Jul. 14, 2014.

(Continued)

*Primary Examiner* — Jennifer E Graser
(74) *Attorney, Agent, or Firm* — Fish & Richardson P.C.

(57) ABSTRACT

The present invention is directed generally to chimeric proteins that can facilitate targeting of nanoparticulate carriers to antigen presenting cells, and to nanoparticulate carriers comprising these chimeric proteins. The invention is also directed to methods of internalizing an antigen in an antigen presenting cell, and methods of eliciting an immune response to an antigen in a subject, using the nanoparticulate carriers comprising the chimeric proteins.

13 Claims, 13 Drawing Sheets

Specification includes a Sequence Listing.

(56) References Cited

OTHER PUBLICATIONS

Mizel et al., "Flagellin as an adjuvant: cellular mechanisms and potential," *J Immunol.*, Nov. 15, 2010;185(10):5677-82. doi: 10.4049/jimmunol.1002156.

Nempont et al., "Deletion of flagellin's hypervariable region abrogates antibody-mediated neutralization and systemic activation of TLR5-dependent immunity," *J Immunol.*, Aug. 1, 2008;181(3):2036-43.

Orlandi et al., "Cloning immunoglobulin variable domains for expression by the polymerase chain reaction," *Proc Natl Acad Sci U S A.*, May 1989;86(10):3833-7.

Wagner et al., "Liposome technology for industrial purposes," *J Drug Deliv.*, 2011:591325. doi: 10.1155/2011/591325. Epub Dec. 5, 2010.

Yamashita et al., "Recent advances in the generation of human monoclonal antibody," *Cytotechnology*, Dec. 2007;55(2-3):55-60. doi: 10.1007/s10616-007-9072-5. Epub Apr. 21, 2007.

Yoon et al., "Structural basis of TLR5-flagellin recognition and signaling," *Science*, Feb. 17, 2012;335(6070):859-64. doi: 10.1126/science.1215584.

Yu et al., "Microfluidic methods for production of liposomes," *Methods Enzymol.*, 2009;465:129-41. doi: 10.1016/S0076-6879(09)65007-2.

Extended European Search Report in corresponding Application No. 15848180.4, dated Sep. 5, 2018, pp. 1-9.

\* cited by examiner

A.

BamHI-FliC-*Spel/TS linker*-gp120-Thrombin-His6-*NotI*

*GGATCC*ATGGCACAAGTCATTAATACAAACAGCCTGTCGCTGTTGACCCAGAATAACCTGAAC
AAATCCCAGTCCGCTCTGGGCACCGCTATCGAGCGTCTGTCTTCCGGTCTGCGTATCAACAGCG
CGAAAGACGATGCGGCAGGTCAGGCGATTGCTAACCGTTTTACCGCGAACATCAAAGGTCTGA
CTCAGGCTTCCCGTAACGCTAACGACGGTATCTCCATTGCGCAGACCACTGAAGGCGCGCTGAA
CGAAATCAACAACAACCTGCAGCGTGTGCGTGAACTGGCGGTTCAGTCTGCTAACAGCACCAA
CTCCCAGTCTGACCTCGACTCCATCCAGGCTGAAATCACCCAGCGCCTGAACGAAATCGACCGT
GTATCCGGCCAGACTCAGTTCAACGGCGTGAAAGTCCTGGCGCAGGACAACACCCTGACCATC
CAGGTTGGTGCCAACGACGGTGAAACTATCGATATCGATCTGAAGCAGATCAACTCTCAGACC
CTGGGTCTGGATACGCTGAATGTGCAACAAAATATAAGGTCAGCGATACGGCTGCAACTGTT
ACAGGATATGCCGATACTACGATTGCTTTAGACAATAGTACTTTTAAAGCCTCGGCTACTGGTC
TTGGTGGTACTGACCAGAAAATTGATGGCGATTTAAAATTTGATGATACGACTGGAAAATATT
ACGCCAAAGTTACCGTTACGGGGGGAACTGGTAAAGATGGCTATTATGAAGTTTCCGTTGATA
AGACGAACGGTGAGGTGACTCTTGCTGGCGGTGCGACTTCCCCGCTTACAGGTGGACTACCTG
CGACAGCAACTGAGGATGTGAAAAATGTACAAGTTGCAAATGCTGATTTGACAGAGGCTAAA
GCCGCATTGACAGCAGCAGGTGTTACCGGCACAGCATCTGTTGTTAAGATGTCTTATACTGATA
ATAACGGTAAAACTATTGATGGTGGTTTAGCAGTTAAGGTAGGCGATGATTACTATTCTGCAA
CTCAAAATAAAGATGGTTCCATAAGTATTAATACTACGAAATACACTGCAGATGACGGTACAT
CCAAAACTGCACTAAACAAACTGGGTGGCGCAGACGGCAAAACCGAAGTTGTTTCTATTGGTG
GTAAAACTTACGCTGCAAGTAAAGCCGAAGGTCACAACTTTAAAGCACAGCCTGATCTGGCGG
AAGCGGCTGCTACAACCACCGAAAACCCGCTGCAGAAAATTGATGCTGCTTTGGCACAGGTTG
ACACGTTACGTTCTGACCTGGGTGCGGTACAGAACCGTTTCAACTCCGCTATTACCAACCTGGG
CAACACCGTAAACAACCTGACTTCTGCCCGTAGCCGTATCGAAGATTCCGACTACGCGACCGAA
GTTTCCAACATGTCTCGCGCGCAGATTCTGCAGCAGGCCGGTACCTCCGTTCTGGCGCAGGCGA
ACCAGGTTCCGCAAAACGTCCTCTCTTTACTGCGT*ACTAGT*<u>ATGAGAGTGAAGGAGAAGTATCA</u>
<u>GCACTTGTGGAGATGGGGGTGGAAATGGGGCACCATGCTCCTTGGGATATTGATGATCTGTA</u>
<u>GTGCTACAGAAAAATTGTGGGTCACAGTCTATTATGGGGTACCTGTGTGGAAAGAAGCAACCA</u>
<u>CCACTCTATTTTGTGCATCAGATGCTAAAGCATATGATACAGAGGTACATAATGTTTGGGCCAC</u>
<u>ACATGCCTGTGTACCCACAGACCCCAACCCACAAGAAGTAGTATTGGAAAATGTGACAGAAAA</u>
<u>TTTTAACATGTGGAAAAATAACATGGTAGAACAGATGCATGAGGATATAATCAGTTTATGGGA</u>
<u>TCAAAGCCTAAAGCCATGTGTAAAATTAACCCCACTCTGTGTTACTTTAAATTGCACTGATTTGA</u>
<u>GGAATGTTACTAAT</u>

FIG. 1A

**ATCAATAATAGTAGTGAGGGAATGAGAGGAGAAATAAAAAACTGCTCTTTCAATATCACCACAAGCA
TAAGAGATAAGGTGAAGAAAGACTATGCACTTTTTTATAGACTTGATGTAGTACCAATAGATAATGAT
AATACTAGCTATAGGTTGATAAATTGTAATACCTCAACCATTACACAGGCCTGTCCAAAGGTATCCTTT
GAGCCAATTCCCATACATTATTGTACCCCGGCTGGTTTTGCGATTCTAAAGTGTAAAGATAAGAAGTTC
AATGGAACAGGGCCATGTAAAAATGTCAGCACAGTACAATGTACACATGGAATTAGGCCAGTAGTGT
CAACTCAACTGCTGTTAAATGGCAGTCTAGCAGAAGAAGAGGTAGTAATTAGATCTAGTAATTTCACA
GACAATGCAAAAAACATAATAGTACAGTTGAAAGAATCTGTAGAAATTAATTGTACAAGACCCAACA
ACAATACAAGGAAAAGTATACATATAGGACCAGGAAGAGCATTTTATACAACAGGAGACATAATAG
GAGATATAAGACAAGCACATTGCAACATTAGTAGAACAAAATGGAATAACACTTTAAATCAAATAGC
TACAAAATTAAAAGAACAATTTGGGAATAATAAAACAATAGTCTTTAATCAATCCTCAGGAGGGGAC
CCAGAAATTGTAATGCACAGTTTTAATTGTGGAGGGGAATTTTTCTACTGTAATTCAACACAACTGTTT
AATAGTACTTGGAATTTTAATGGTACTTGGAATTTAACACAATCGAATGGTACTGAAGGAAATGACAC
TATCACACTCCCATGTAGAATAAAACAAATTATAAACATGTGGCAAGAAGTAGGAAAAGCAATGTAT
GCCCCTCCCATCAGAGGACAAATTAGATGTTCATCAAATATTACAGGGCTGATATTAACAAGAGATGG
TGGAAATAACCACAATAATGATACCGAGACCTTTAGACCTGGAGGAGGAGATATGAGGGACAATTG
GAGAAGTGAATTATATAAATATAAAGTAGTAAAAATTGAACCATTAGGAGTAGCACCCACCAAGGCA
AAGAGAAGAGTGGTGCAGAGAGAAAAAAGA**CTGGTTCCGCGTGGATCT*CACCATCACCATCACCATT
AAGTAAGCGGCCGC*

FIG. 1A (CON'T)

B.

FliC-*TS*-gp120-thrombin-*His6*

**MAQVINTNSLSLLTQNNLNKSQSALGTAIERLSSGLRINSAKDDAAGQAIANRFTANIKG
LTQASRNANDGISIAQTTEGALNEINNNLQRVRELAVQSANSTNSQSDLDSIQAEITQRL
NEIDRVSGQTQFNGVKVLAQDNTLTIQVGANDGETIDIDLKQINSQTLGLDTLNVQQKYK
VSDTAATVTGYADTTIALDNSTFKASATGLGGTDQKIDGDLKFDDTTGKYYAKVTVTGGT
GKDGYYEVSVDKTNGEVTLAGGATSPLTGGLPATATEDVKNVQVANADLTEAKAALTAAG
VTGTASVVKMSYTDNNGKTIDGGLAVKVGDDYYSATQNKDGSISINTTKYTADDGTSKTA
LNKLGGADGKTEVVSIGGKTYAASKAEGHNFKAQPDLAEAAATTTENPLQKIDAALAQVD
TLRSDLGAVQNRFNSAITNLGNTVNNLTSARSRIEDSDYATEVSNMSRAQILQQAGTSVL
AQANQVPQNVLSLLR*TSMRVKEKYQHLWRWGWKWGTMLLGILMICSATEKLWVTVYYGVP
VWKEATTTLFCASDAKAYDTEVHNVWATHACVPTDPNPQEVVLENVTENFNMWKNNMVEQ
MHEDIISLWDQSLKPCVKLTPLCVTLNCTDLRNVTNINNSSEGMRGEIKNCSFNITTSIR
DKVKKDYALFYRLDVVPIDNDNTSYRLINCNTSTITQACPKVSFEPIPIHYCTPAGFAIL
KCKDKKFNGTGPCKNVSTVQCTHGIRPVVSTQLLLNGSLAEEEVVIRSSNFTDNAKNIIV
QLKESVEINCTRPNNNTRKSIHIGPGRAFYTTGDIIGDIRQAHCNISRTKWNNTLNQIAT
KLKEQFGNNKTIVFNQSSGGDPEIVMHSFNCGGEFFYCNSTQLFNSTWNFNGTWNLTQSN
GTEGNDTITLPCRIKQIINMWQEVGKAMYAPPIRGQIRCSSNITGLILTRDGGNNHNNDT
ETFRPGGGDMRDNWRSELYKYKVVKIEPLGVAPTKAKRRVVQREKR**LVPRGS*HHHHHH*

FIG. 1B

C.

FliC-gp120-6xHis

Mw: 110922.22
pI: 7.48

D = FliC domains
D1 contains TLR5 binding site
V = gp120 variable regions
Black lines = N-glycosylation sites
HHHHHH = 6xHis tag

D.

CHIMERIC PROTEINS

FIELD OF THE INVENTION

The present invention is directed generally to chimeric proteins that can facilitate binding of nanoparticulate carriers to antigen presenting cells and subsequent internalisation by the cells, and to nanoparticulate carriers comprising these chimeric proteins. The invention is also directed to methods of internalising an antigen in an antigen presenting cell, and methods of eliciting an immune response to an antigen in a subject, using the nanoparticulate carriers comprising the chimeric proteins.

RELATED APPLICATIONS

This application is the National Stage of International Application Serial No. PCT/AU2015/050614, filed 9 Oct. 2015, which is related to and claims priority from Australian Provisional Patent Application No. 2014904028, entitled "Chimeric proteins", filed on 9 Oct. 2014. The contents of International Application Serial No. PCT/AU2015/050614 and Australian Provisional Patent Application No. 2014904028 are incorporated herein by reference in their entirety.

BACKGROUND OF THE INVENTION

Optimal vaccine design requires a balance between maximal immunogenicity, safety and tolerability. The improved safety profile of modern recombinant vaccines has generally come with lower immunogenicity profiles. There is therefore a need for adjuvants and novel delivery systems that boost immunogenicity, while retaining safety and tolerability.

SUMMARY OF THE INVENTION

In one aspect, the present invention is directed to a chimeric protein, comprising a first polypeptide and a second polypeptide, wherein the first polypeptide is a Toll Like Receptor 5 (TLR5) agonist; and the second polypeptide has at least 50% sequence identity to the gp120 polypeptide set forth in SEQ ID NO:1 and at least 8 N-glycosylation sites.

In some embodiments, the TLR5 agonist is a flagellin polypeptide, an anti-TLR5 antibody or an anti-TLR5 aptamer. For example, the TLR5 agonist can be a flagellin polypeptide selected from among a *Salmonella* spp, *Escherichia* spp, *Borrelia* spp, *Helicobacter* spp, *Campylobacter* spp, *Caulobacter* spp, *Vibrio* spp, *Bacillus* spp, *Pseudomonas* spp, *Rhizobium* spp, *Halobacterium* spp, *Haloferax* spp, *Clostridium* spp, *Enterobacter* spp, *Envinia* spp, *Klebsiella* spp, *Yersinia* spp, *Proteus* spp, *Serratia* spp, *Shewanella* spp, *Shigella* spp, and *Streptomyces* spp. flagellin. In a particular example, the amino acid sequence of the flagellin polypeptide has at least 90% sequence identity to the sequence set forth in SEQ ID NO:2.

In some embodiments, the second polypeptide has at least 90% sequence identity to the gp120 polypeptide set forth in SEQ ID NO:1.

In one embodiment, the C-terminus of the first polypeptide is linked to the N-terminus of the second polypeptide. In another embodiment, the N-terminus of the first polypeptide is linked to the C-terminus of the second polypeptide.

In further embodiments of the present invention, the chimeric protein can also comprise a tag, such as, for example, a histidine tag.

In a particular embodiment, the TLR5 agonist is a flagellin polypeptide and is linked to a gp120 polypeptide. In a further embodiment, the chimeric protein has at least 90% sequence identity to the polypeptide set forth in SEQ ID NO:5.

In one embodiment of the present invention, the chimeric protein is glycosylated. For example, the chimeric protein can comprise an insect cell glycosylation pattern.

In a further aspect, the invention is directed to a nucleic acid molecule encoding a chimeric protein described above and herein.

Another aspect of the present invention is related to nanoparticulate carriers comprising a chimeric protein described above and herein.

In one embodiment, the nanoparticulate carrier comprises at least one additional TLR agonist, such as, for example, Pam3Cys, Pam2Cys, MALP2, MPLA, a triacylated lipopeptide, bacterial peptidoglycan, bacterial lipoprotein, lipoteichoic acid, lipopolysaccharide, a GPI-anchor protein, a Neisserial porins, phospholipomannan, CFA, FSL-1, Hib-OMPC, RSV F-protein, glycoinositolphospholipid, Hsp60, Hsp70, fibronectin domain A, surfactant protein A, hyaluronan, HMGB-1, AGP, RC-529, MDF2β, phenol-soluble modulin, diacylated lipopeptides, LTA, zymosan, an imidazoquinoline, loxoribine and hemozoin.

In some embodiments, the chimeric protein is attached to the surface of the nanoparticulate carrier via chelation. For example, the chimeric protein may comprise a histidine tag and the nanoparticulate carrier may comprise a nitrilotriacetic acid moiety, and the chimeric protein is attached to the nanoparticulate carrier via chelation between the histidine tag, the nitrilotriacetic acid moiety and a metal ion. In some examples, the nitrilotriacetic acid moiety is nitrilotriacetic acid (NTA) or trinitrilotriacetic acid (3NTA). In one embodiment, the nitrilotriacetic acid moiety is attached to at least one aliphatic chain. In particular examples, the nitrilotriacetic acid moiety is attached to ditetradecylamine (DTDA), Pam2Cys, or Pam3Cys. In one embodiment, the nanoparticulate carrier comprises nitrilotriacetic acid-ditetradecylamine (NTA-DTDA) or 3(nitrilotriacetic acid)-ditetradecylamine (3NTADTDA) or Pam2CysSerLys8Cys-3NTA.

In some embodiments, the nanoparticulate carrier is selected from among a liposome, virosome, virus-like particle, archaeosome, plasma membrane vesicle, niosome, lipid core peptide, immunostimulating complex and polymer based nanoparticle.

In one embodiment, the nanoparticulate carrier also comprises an antigen. In some examples, the antigen is attached to the surface of the nanoparticulate carrier. In other examples, the antigen is encapsulated within the nanoparticulate carrier.

In further aspects, the present invention is directed to a method of eliciting an immune response to an antigen in a subject, the method comprising administering to the subject a nanoparticulate carrier comprising a chimeric protein described above and herein and an antigen. In some embodiments, the immune response comprises a $CD8^+$ T cell response. In further embodiments, the immune response comprises a $CD4^+$ T cell response and an antibody response.

In another aspect, the present invention is directed to a method of internalizing an antigen in an antigen presenting cell, the method comprising contacting the antigen presenting cell with a nanoparticulate carrier comprising a chimeric protein described above and herein and an antigen. In particular embodiments, the antigen presenting cell is a dendritic cell.

DETAILED DESCRIPTION OF THE INVENTION

Figure 1C:
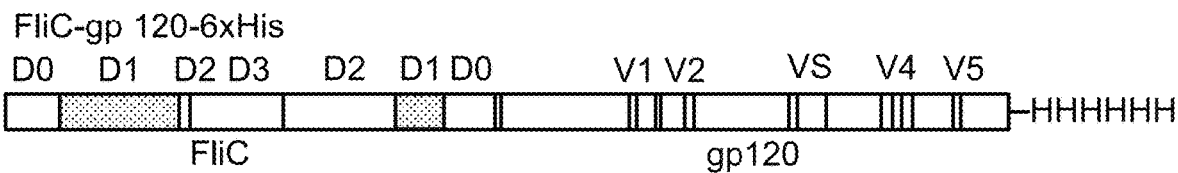
FIG. 1 shows the Fgl15 chimeric protein. (A) Nucleotide sequence of the Fgl15 expression cassette. (B) Amino acid sequence of the Fgl15 chimeric protein (C) Schematic of the Fgl15 chimeric protein showing potential N-glycosylation sites. (D) SDS-PAGE analysis of purified Fgl15 chimeric protein expressed in Sf9 cells, showing pooled peak A (lane 2) and peak B (lane 3) fractions, with molecular weight markers in lane 1.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

As used in the subject specification, the singular forms "a", "an" and "the" include plural aspects unless the context clearly dictates otherwise. Thus, for example, reference to "a" includes a single as well as two or more; reference to "an" includes a single as well as two or more; reference to "the" includes a single as well as two or more and so forth.

As used herein, the term "toll-like receptor 5" or "TLR5" has its general meaning in the art and is intended to mean a toll-like receptor 5 of any species. Most typically, the TLR5 is a human TLR5. TLR5 is expressed on monocytes, neutrophils, macrophages, dendritic cells and intestinal epithelial cells. Upon activation, a TLR5 induces a cellular immune response by transducing an intracellular signal that is propagated through a series of signaling molecules from the cell surface to the nucleus. Typically, the intracellular domain of TLR5 recruits the adaptor protein, MyD88, which recruits the serine/threonine kinases IRAK (IRAK-1 and IRAK-4). IRAK form a complex with TRAF6, which then interacts with various molecules that participate in transducing the TLR signal. These molecules and other TLR5 signal transduction pathway components stimulate the activity of transcription factors, such as NF-kB, and the corresponding induction of a range of inflammatory-related target genes, such as, for example, IL-8 and TNF-α.

As used herein, a TLR5 agonist is any molecule that can activate TLR5. For the purposes of this invention, the TLR5 agonist is a polypeptide. The ability of a polypeptide to activate TLR5 (i.e. to exhibit "TLR5 agonist activity") can be assessed using any method known in the art, such as methods that detect and/or measure NF-kB activation. For example, TLR5 reporter cell lines that stably expresses TLR5 and a reporter gene under the transcriptional control of an NF-kB response element (e.g. HEK-Blue™ hTLR5 or mTLR5: InvivoGen) can be used to assess the TLR5 agonist activity of a polypeptide.

The term "N-glycosylation site" refers to a site in a polypeptide where a sugar moiety is attached to an asparagine residue during glycosylation. N-glycosylation sites are identified by the sequence motif N-X-S/T/C, wherein X is any amino acid residue except proline, N is asparagine and S/T/C is either serine, threonine or cysteine, preferably serine or threonine, and most preferably threonine.

The term "nanoparticulate carrier" refers to a small particle of less than about 1000 nm diameter, to which one or more polypeptides or proteins can be attached. Nanoparticulate carriers may be neutral, anionic or cationic, and include, for example, liposomes, virosomes, virus-like particles (VLPs), archaeosomes, plasma membrane vesicles (PMVs), niosomes, lipid core peptides (LCPs), immunostimulating complexes (ISCOMs), and polymer based nanoparticles (e.g. biodegradeable nanoparticles such as Poly(D,L-lactic-co-glycolic acid)(PLGA) nanoparticles, polypropylene sulphide nanoparticles and polyhydroxylated-nanoparticles).

The terms "linked" and "attached" are used interchangeably and relate to any type of interaction that join two entities, such as two polypeptides or a chimeric protein and a nanoparticle, and include covalent bonds or non-covalent bonds, such as, for example, hydrophobic/hydrophilic interactions, van der Waals forces, ionic bonds or hydrogen bonds.

As used herein, "antibody" refers to immunoglobulins and immunoglobulin fragments, whether natural or partially or wholly synthetically, such as recombinantly, produced, including any fragment thereof containing at least a portion of the variable region of the immunoglobulin molecule that retains the binding specificity ability of the full-length immunoglobulin. Hence, an antibody includes any protein having a binding domain that is homologous or substantially homologous to an immunoglobulin antigen-binding domain (antibody combining site). Antibodies include antibody fragments. As used herein, the term antibody includes synthetic antibodies, recombinantly produced antibodies, multispecific antibodies (e.g., bispecific antibodies), human antibodies, non-human antibodies, humanized antibodies, chimeric antibodies, intrabodies, and antibody fragments, such as, but not limited to, Fab fragments, Fab1 fragments, F(ab')2 fragments, Fv fragments, disulfide-linked Fvs (dsFv), Fd fragments, Fd' fragments, single-chain Fvs (scFv), single-chain Fabs (scFab), diabodies or antigen-binding fragments of any of the above. Antibodies provided herein include members of any immunoglobulin type (e.g., IgG, IgM, IgD, IgE, IgA and IgY), any class (e.g. IgG1, IgG2, IgG3, IgG4, IgA1 and IgA2) or subclass (e.g., IgG2a and IgG2b).

As used herein, an "antigen-binding fragment" of an antibody includes any fragment of an antibody that retains the ability to bind to the same antigen as the antibody. Typically, the antigen binding fragment binds to the antigen with an affinity that is at least or about 30%, 40%, 50%, 60%, 70%, 80%, 90%, 100%, or more of the binding affinity exhibited by the antibody. Exemplary antigen-binding fragments include, but are not limited to, Fab fragments, Fab1 fragments, F(ab')2 fragments, Fv fragments, disulfide-linked Fvs (dsFv), Fd fragments, Fd' fragments, single-chain Fvs (scFv), single-chain Fabs (scFab) and diabodies.

As used herein, the term "% identical" means that in a comparison of two sequences over a specified region the two sequences have the specified number of identical residues in the same position. The term "% similar" has a similar meaning but in addition to the number of identical amino acids between the two sequences regard is also had to where the amino acids are not identical but are conservative substitutions.

The term "subject" as used herein refers to an animal, in particular a mammal and more particularly a primate including a lower primate and even more particularly, a human who can benefit from the medical protocol of the present invention. A subject regardless of whether a human or non-human animal or embryo may be referred to as an individual, subject, animal, patient, host or recipient. The present invention has both human and veterinary applications. For convenience, an "animal" specifically includes livestock animals such as cattle, horses, sheep, pigs, camelids, goats and donkeys. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates. In some embodiments, the subject is human.

TABLE A

List of sequences

| Sequence description | Amino acid (aa)/ nucleotide (nt) | SEQ ID NO |
|---|---|---|
| HIV gp120 | aa | 1 |
| HIV gp120 | nt | 2 |
| S. typhimurium FliC | aa | 3 |
| S. typhimurium FliC | nt | 4 |
| Fg115 chimeric protein | aa | 5 |
| Fg115 chimeric protein | nt | 6 |
| ACTAGT (TS) linker | nt | 7 |
| Thrombin cleavage sequence | aa | 8 |
| Thrombin cleavage sequence | nt | 9 |
| His(6) tag | aa | 10 |
| His(6) tag | nt | 11 |
| FlgT peptide | aa | 12 |

Chimeric Proteins

The chimeric proteins of the present invention comprise a first polypeptide that is a TLR5 agonist and a second polypeptide that has at least 50% sequence identity to the gp120 polypeptide set forth in SEQ ID NO:1 and at least 8 N-glycosylation sites. Accordingly, when produced in a manner that facilitates glycosylation, the second polypeptide is a highly glycosylated glycoprotein. The chimeric proteins can be used to facilitate binding of nanoparticulate carriers to antigen presenting cells and/or facilitate internalisation of nanoparticulate carriers by antigen presenting cells, such as dendritic cells. Accordingly, the chimeric proteins can facilitate internalisation of an antigen encapsulated within or attached to a nanoparticulate carrier by an antigen presenting cell, and also facilitate an immune response to that antigen.

Without wishing to be bound by theory, it is postulated that the chimeric proteins of the present invention bind antigen presenting cells, such as dendritic cells, through the highly glycosylated second polypeptide that has at least 50% sequence identity to the gp120 polypeptide set forth in SEQ ID NO:1 and at least 8 N-glycosylation sites. This glycoprotein can interact with lectins, such as DC-SIGN or the Mannose Receptor, on the antigen presenting cell. The chimeric proteins may also bind antigen presenting cells, such as dendritic cells, macrophages, and monocytes, via interaction between the TLR5 agonist in the chimeric protein and TLR5 on the cell surface. Accordingly, the chimeric proteins of the present invention can be used to facilitate delivery of a nanoparticulate carrier engrafted with the chimeric proteins to an antigen presenting cell, and subsequent internalisation of the carrier by antigen presenting cell. When the nanoparticulate carrier is loaded with an antigen (i.e. an antigen is encapsulated within and/or attached to the surface of the carrier), the chimeric proteins facilitate internalisation of the antigen by the antigen presenting cell. Typically, the antigen presenting cell is a dendritic cell.

As demonstrated herein, nanoparticulate carriers engrafted with the chimeric proteins exhibit increased binding to antigen presenting cells and increased internalisation by antigen presenting cells compared to an unengrafted carrier. Moreover, activation of TLR5 by the TLR5 agonist in the chimeric proteins can help stimulate a proinflammatory response to the antigen encapsulated within and/or attached to the surface of the carrier. Activation of TLR5 by a TLR5 agonist can result in, for example, the induction of proinflammatory cytokines and chemokines, increased T and B cell recruitment to secondary lymphoid sites, activation of DCs, direct stimulation of CD4$^+$ and CD8$^+$ T cells, and induction of a humoral immune response characterised by high titres of IgG1 and IgG2a. In addition, the immune response to an antigen may be further enhanced if the second polypeptide contains "non-self" glycan structures or patterns, i.e. glycan structures or patterns that are different to the glycan structures or patterns normally produced in the species to which the chimeric proteins are administered. The combination of the enhanced internalisation afforded by the chimeric proteins, the adjuvant effect of the activation of TLR5 by the TLR5 agonist in the chimeric protein, and in some cases the adjuvant effect of "non-self" glycosylation of the second polypeptide, results in an enhanced immune response to an antigen encapsulated within and/or attached to the surface of a nanoparticulate carrier engrafted with the chimeric proteins, compared the immune response generated using an unengrafted nanoparticulate carrier.

TLR5 Agonists

TLR5 agonists useful for the present invention include any polypeptide that can activate TLR5, including but not limited to, flagellin polypeptides, anti-TLR5 antibodies, and anti-TLR5 aptamers. Most typically, the TLR5 agonists activate human TLR5, but those skilled in the art would understand that TLR5 agonists that activate TLR5 from other species can also be used, depending upon the desired specificity and utility of the chimeric proteins. In some instances, the TLR5 agonist activated TLR5 from multiple species.

In some examples, the TLR5 agonist in the chimeric proteins of the present invention is a flagellin polypeptide. Flagellins are part of bacterial flagellae, which are responsible for motility and chemotaxis. Depending on bacterial species, the molecular weight of flagellins range from 28 to 80 kDa. Flagellins have conserved regions at the N-terminus (about 170 amino acid residues) and the C-terminus (about 100 amino acid residues), flanking a hypervariable region. The N- and C-terminal portions of flagellins form packed α-helical structures, which constitute the D0 and D1 domains. Studies indicate that the D1 domain is involved in both high affinity binding and TLR5 signaling, whereas D0 contributes to TLR5 activation, but has no or little effect on binding (Yoon et al. (2012) Science. 335(6070): 859-864).

Flagellins have been shown to have potent adjuvanting effects, including, but not limited to, the induction of cytokines and chemokines, increased T and B cell recruitment to secondary lymphoid sites, activation of DCs, direct stimulation of CD4$^+$ and CD8$^+$ T cells, and induction of a humoral immune response characterised by high titres of IgG1 and IgG2a (Mizel & Bates 2010 J Immunol. 185(10):5677-82). Flagellins also have the advantage of being effective at low doses, not promoting IgE responses, and its adjuvant effect not being impaired by pre-existing immunity (Mizel & Bates 2010 J Immunol. 185(10):5677-82).

Any flagellin polypeptide that is capable of activating TLR5 is useful for the present invention, including, but not limited to, flagellins derived from *Salmonella* spp, *Escherichia* spp, *Borrelia* spp, *Helicobacter* spp, *Campylobacter* spp, *Caulobacter* spp, *Vibrio* spp, *Bacillus* spp, *Pseudomonas* spp, *Rhizobium* spp, *Halobacterium* spp, *Haloferax* spp, *Clostridium* spp, *Enterobacter* spp, *Envinia* spp, *Klebsiella* spp, *Yersinia* spp, *Proteus* spp, *Serratia* spp, *Shewanella* spp, *Shigella* spp, and *Streptomyces* spp. The amino acid sequences and nucleotide sequences of flagellins are publically available in the NCBI Genbank and UniProt databases. Non-limiting examples of flagellin polypeptides useful for the present invention include *Salmonella enterica* subsp. *enterica* serovar Typhimurium flagellins (*S. typhimurium*; e.g. UniProt Acc. No. P06179), *S. dublin* flagellins (e.g. UniProt Acc. No. Q06971), *S. paratyphi* flagellins (e.g. UniProt Acc. No. P06178), *S. enteritidis* flagellins (e.g. UniProt Acc. No. Q06972), *Escherichia coli* flagellins (e.g. UniProt Acc. No. P04949), *Pseudomonas aeruginosa* flagellins (e.g. UniProt Acc. Nos. P21184 and P72151), *Shigella flexneri* flagellins (e.g. UniProt Acc. No. Q08860), *Proteus mirabilis* flagellins (e.g. UniProt Acc. Nos. P42272 and P42273), *Serratia marcescens* flagellins (e.g. UniProt Acc. No. P13713), and *Brucella melitensis* flagellins (e.g. UniProt Acc. No. Q8YDM5).

Flagellin polypeptides useful for the present invention include flagellin-derived polypeptides, such as fragments and variants of wild-type flagellins that retain TLR5 agonist activity. Typically, the fragments or variants retain at least 20% (e.g., 20%, 30%, 40%, 50%, 60%, 70%, 80%, 90% or more) of the TLR5 agonist activity of the wild-type flagellin polypeptide. Those skilled in art would be familiar with the many methods available to assess TLR5 agonist activity, such as assays that utilise a TLR5 reporter cell line that stably expresses TLR5 and a reporter gene under the transcriptional control of an NF-kB response element. In some instances, the variants have improved TLR5 agonist activity compared to the wild-type polypeptide (see, e.g., WO2008097016). The fragments or variants typically have at least 70%, 75%, 80%, 85%, 90%, or 95% sequence identity to a region of wild-type flagellin, such as the D0 and/or D1 regions. Those skilled in the art would understand that, for the purposes of generating or identifying flagellin variants that retain TLR5 agonist activity, regions of the flagellin polypeptide that are not involved in TLR5 binding and/or activation, such as the hypervariable region, would generally be more susceptible to variation than regions that are critical to TLR5 binding and/or activation, such as the D0 and D1 regions. Accordingly, in some instances, the flagellin variants or fragments are mostly modified in the hypervariable region. In some instances, a flagellin polypeptide with all or part of the hypervariable region deleted may be advantageous, as such a polypeptide can exhibit reduced immunogenicity compared to a wild-type flagellin (see e.g. Nempont et al. (2008) J. Immunol. 181:2036-2043). Flagellin polypeptides comprising essentially the D0 and D1 regions, with the hypervariable region completely or partially deleted, are known in the art and can be used as a TLR5 agonist in the chimeric polypeptides of the present invention (see, e.g. US20090011982, WO2009156405, Burdelya et al. (2008) Science 320: 226-230 and Nempont et al. (2008) J. Immunol. 181:2036-2043). It is well within the skill of a skilled artisan to produce, select and/or identify a flagellin polypeptide that is suitable for the purposes of the present invention.

In one particular example, the TLR5 agonist in the chimeric proteins of the present invention is a flagellin polypeptide derived from the FliC gene of *S. typhimurium*. In one embodiment, the flagellin polypeptide comprises an amino acid sequence set forth in SEQ ID NO:2. In another example, the TLR5 agonist is a flagellin polypeptide comprising an amino acid sequence that has at least 80%, 85%, 90%, 91%, 92%, 93%, 94%, 95%, 96%, 97%, 98% or 99% sequence identity to the sequence set forth in SEQ ID NO:2.

Alternatively, the TLR5 agonist according to the invention may be an anti-TLR5 antibody or antigen-binding fragment thereof. Anti-TLR5 antibodies that act as TLR5 agonists can be generated using standard techniques for preparing antibodies against antigens (see e.g. for review, Yamashita et al. (2007) Cytotechnology. 55(2-3): 55-60). For example, monoclonal antibodies specific for TLR5 can be obtained by injecting a non-human subject, such as a mouse, with TLR5. B-lymphocytes can then be obtained and fused with myeloma cells to produce hybridomas, which are cloned. Positive clones that produce antibodies to TLR5 are selected using standard techniques (e.g. ELISpot). The clones that produce antibodies to the antigen are then cultured and the secreted antibodies are isolated from the hybridoma cultures. Monoclonal antibodies can be isolated and purified from hybridoma cultures by a variety of well-established techniques including, but not limited to, affinity chromatography with Protein-A SEPHAROSE®, size-exclusion chromatography, and ion-exchange chromatography. After the initial raising of antibodies to the immunogen, the antibodies can be sequenced and subsequently prepared by recombinant techniques.

In instances where mouse monoclonal antibodies are produced, such antibodies can be humanised or chimerised using methods well known to those skilled in the art. Chimeric antibodies are recombinant proteins in which the variable regions of a human antibody have been replaced by the variable regions of, for example, a mouse antibody. Murine immunoglobulin variable domains can be cloned from nucleic acid encoding the antibody and chimeric antibodies produced using techniques well known in the art (see e.g. Orlandi et al., (1989) PNAS USA 5:3833-3837; Kaluza et al. (1992) Gene 122(2):321-8).

Techniques for producing humanized monoclonal antibodies by transferring the CDRs from the heavy and light variable chains of a mouse or chimeric antibody into the corresponding variable domains of a human antibody also are well known in the art (see, e.g., Riechmann et al., (1988) Nature 332:323-327; Singer et al., (1993) J. Immunol. 750:2844-2857). In some instances, further modifications are made in the human framework regions of the humanised antibody to increase affinity (see e.g. Tempest et al. (1991) Biotechnology 9:266-271).

Alternatively, transgenic animals that have been genetically engineered to produce human antibodies can be used to generate antibodies against TLR5 using standard immunization protocols (see e.g. Lonberg et al., (1994) Nature 55:856-859, Lonberg (2005) Nat Biotechnol. 23(9):1117-25). Such mice are available commercially, for example, the XenoMouse® from Amgen (Thousand Oaks, Calif.) (described by Green et al., (1999) J. Immunol. Methods 231: 11-23).

In another embodiment the TLR5 agonist is an aptamer. Aptamers are a class of molecule that represents an alternative to antibodies in term of molecular recognition, and are oligopeptide sequences with the capacity to recognize virtually any class of target molecules with high affinity and specificity. Peptide aptamers consists of a conformationally constrained antibody variable region displayed by a platform protein, such as *E. coli* Thioredoxin A, and are selected from combinatorial libraries by two hybrid methods.

Polypeptides Having at Least 50% Sequence Identity to gp120 and at Least 8 N-glycosylation Sites The second polypeptide of the chimeric protein has at least 50% sequence identity to the gp120 polypeptide set forth in SEQ ID NO:1 and at least 8 N-glycosylation sites. In some examples, the polypeptide has at least 55%, 60%, 65%, 70%, 75%, 80%, 85%, 90%, 91%, 92%, 93%, 94%, 95%, 96%, 97%, 98% or 99% sequence identity to the gp120 polypeptide set forth in SEQ ID NO:1 and at least 8 N-glycosylation sites, such as, for example, 8, 9, 10, 11 or 12 N-glycosylation sites.

When produced in an appropriate system that enables glycosylation of the polypeptide at the N-glycosylation sites, the second polypeptide is a heavily glycosylated glycoprotein and can bind to lectins such as DC-SIGN on antigen presenting cells, as has been shown with wild-type gp120 from HIV-1. DC-SIGN is a C-type lectin that recognises carbohydrates on microbes, interacting with either high mannose structures or fucose-containing glycans on a wide variety of bacteria, viruses, parasites and fungi (Gringhuis & Geijtenbeek (2010 Methods Enzymol. 480:151-64). Most typically, the second polypeptide can bind to human DC-SIGN on human dendritic cells. The second polypeptide may also bind other lectins, such as Langerin on Langerhans cells, the mannose receptor on dermal dendritic cells, galectin-1 on various $CD4^+$ antigen presenting cells, and DC immunoreceptor (DCIR) on dendritic cells, just as gp120 from HIV-1 has been shown to (Turville et al (2003) J Leukoc Biol. 74(5):710-8; Sato et al (2012) Ann N Y Acad Sci. 1253:133-48).

In one example, the second polypeptide is a gp120 polypeptide. In a particular embodiment, the gp120 polypeptide comprises the sequence set forth in SEQ ID NO:1, and has 12 N-glycosylation sites.

Production of Chimeric Proteins

The chimeric proteins can be produced using one or more of the methods well known to those skilled in the art, including recombinant methods, chemical synthesis methods, or a combination thereof. The chimeric proteins can be produced as a single polypeptide or can be produced by generating the first and second polypeptides separately and then linking them. In particular examples, the chimeric proteins are expressed from a single nucleic acid molecule encoding both the first and second polypeptides in-frame, such as the nucleic acid molecule set forth in SEQ ID NO:6. In other examples, the first and second polypeptides are generated separately and then subsequently linked to form the chimeric protein. Such linkage can be via any means, such as chemical crosslinking of the first polypeptide to the second polypeptide. Numerous chemical crosslinking agents are known in the art (e.g., commercially available from Pierce, Rockford Ill.)

The first and second polypeptides can be linked in any orientation. For example, in the chimeric proteins of the present invention, the N-terminus of the first polypeptide may be linked to the C-terminus of the second polypeptide. In other examples, the N-terminus of the second polypeptide is linked to the C-terminus of the first polypeptide. The first and second polypeptides can be linked directly (i.e. the N-terminal amino acid of one polypeptide is directly linked to and is adjacent to the C-terminal amino acid of the other polypeptide) or can be linked via a linker or spacer, such as a peptide linker, which can reduce steric hindrance. Furthermore, the chimeric proteins may comprise one or more additional entities, such as an affinity tag to facilitate purification (e.g. a myc epitope, GST fusion or histidine tag), or other entities to facilitate subsequent attachment of the chimeric protein to a nanoparticulate carrier. In a particular example, the chimeric proteins comprise a histidine tag, which can facilitate both purification of the chimeric proteins and also engraftment to nanoparticulate carriers. In further examples, the chimeric proteins can comprise one or more antigens, including one or more bacterial, viral, fungal, or tumour antigens.

Methods for producing recombinant polypeptides are well known in the art and can be used to obtain the first and/or second polypeptides for inclusion in the chimeric proteins of the invention. Nucleic acid encoding the first and/or second polypeptides can be cloned into an expression vector suitable for the expression system of choice, operably linked to regulatory sequences that effect expression of the heterologous nucleic acid molecule. Many expression vectors are available and known to those of skill in the art for the expression of polypeptides. The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

As would be understood from the above disclosure, at least the second polypeptide should be produced as a glycoprotein. When the chimeric protein is produced as a fusion protein from one transcript, the fusion protein is typically produced as a glycoprotein. Furthermore, and as discussed above, producing the second polypeptide or the entire chimeric protein with "non-self" glycans, i.e. glycan structures or patterns that are different to the glycan structures or patterns normally produced in the species to which the chimeric proteins are administered, can increase the adjuvant activity of the second polypeptide. Accordingly, if the chimeric proteins are to be engrafted on nanoparticulate carriers and administered to a human subject, the chimeric proteins (or at least the second polypeptide) may be produced using non-mammalian expression systems that facilitate glycosylation. It is well within the skill of a skilled artisan to select the most appropriate expression system for producing the chimeric proteins.

In one example, insects and insect cells are used for expressing polypeptides with post-translational modifications such as N-linked glycosylation, so as to produce a chimeric protein with an insect cell glycosylation pattern or structure. The baculovirus expression system can be used in conjunction with the insect cells. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV). Exemplary insect cell lines include such the Sf9 cell line derived from *Spodoptera frupperda*, the A7S cell line derived from *Pseudaletia unipuncta* and the DpN1 cell line derived from *Danaus plexippus*. For high level expression, the nucleotide sequence of the molecule to be expressed is fused immediately downstream of the polyhedrin initiation codon of the virus.

Yeasts such as *Saccharomyces cerevisiae, Schizosaccharomyces pombe, Yarrowia hpolytica, Kluyveromyces lactis,* and *Pichia pastoris* are also useful expression hosts for glycoproteins. Yeast can be transformed with episomal replicating vectors or by stable chromosomal integration by homologous recombination. Typically, inducible promoters, such as include GAL1, GAL7, and GAL5, are used to regulate gene expression. Yeast expression vectors often include a selectable marker such as LEU2, TRP1, HIS3, and URA3 for selection and maintenance of the transformed DNA.

Mammalian expression systems also can be used to express the proteins and polypeptides described herein. Expression constructs can be transferred to mammalian cells by viral infection, such as using adenovirus, or by direct DNA transfer such as using liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the S V40 promoter-enhancer, the human cytomegalovirus (CMV) promoter, and the long terminal repeat of Rous sarcoma virus (RSV). Exemplary cell lines available for mammalian expression include, but are not limited to, mouse, rat, human, monkey, and chicken and hamster cells, such as BHK, 293-F, CHO, Balb/3T3, HeLa, MT2, mouse NSO (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells.

Glycoproteins can also be synthesised using solid-phase glycopeptide synthesis, native chemical ligation (NCL), and expressed protein ligation (EPL).

Following production, the chimeric proteins or the first and second polypeptides (if being produced separately) can be purified using any method known to those of skill in the art including, but not limited to, SDS-PAGE, size fraction and size exclusion chromatography, ammonium sulfate precipitation, chelate chromatography, ionic exchange chromatography and affinity chromatography. Affinity purification techniques can be used to improve the efficiency and purity of the preparations. For example, antibodies, receptors and other molecules that bind the chimeric proteins or first or second polypeptides can be used in affinity purification. As discussed above, constructs can be engineered to add an affinity tag such as a myc epitope, GST fusion or His6 and purification can be performed with myc antibodies, glutathione resin, and Ni-resin, respectively. Purity can be assessed by any method known in the art including gel electrophoresis and staining and spectrophotometric techniques.

Nanoparticulate Carriers

The nanoparticulate carriers of the present invention comprise at least one chimeric protein described above and herein. Accordingly, the nanoparticulate carriers can comprise a chimeric protein comprising a first polypeptide that is a TLR5 agonist and a second polypeptide that has at least 50% sequence identity to the gp120 polypeptide set forth in SEQ ID NO:1 and at least 8 N-glycosylation sites. By virtue of the properties of the chimeric proteins, described above, nanoparticulate carriers comprising the chimeric proteins can bind to, and be internalised within, antigen presenting cells, such as dendritic cells.

Any nanoparticulate carrier to which one or more polypeptides can be attached, and which can be internalised by an antigen presenting cell, in particular a dendritic cell, is contemplated for the present invention. Exemplary nanoparticulate carriers include, but are not limited to, liposomes (including neutral, anionic or cationic liposomes; and ethosomes), virosomes, virus-like particles (VLPs), archaeosomes, plasma membrane vesicles (PMVs), niosomes, lipid core peptides (LCPs), immunostimulating complexes (ISCOMs), polymer based nanoparticles (e.g. biodegradeable nanoparticles such as Poly(D,L-lactic-co-glycolic acid) (PLGA) nanoparticles, polypropylene sulphide nanoparticles and polyhydroxylated-nanoparticles). A wide variety of nanoparticulate carriers are well known in the art and have been extensively studied and described elsewhere (for review, see e.g. Joshi et al. (2012) J Cont Release 161:25-37; Altin (2012) Liposomes and other nanoparticles as cancer vaccines and immunotherapeutics. Chapter 8 In: *Innovations in Vaccinology: from design, through to delivery and testing*. S. Baschieri Ed, Springer; Gregory et al. (2013) Front Cell Infect Microbiol. 3: 13; and Zhao et al. (2014) 32(3):327-337).

In particular examples, the nanoparticulate carriers of the present invention are liposomes, which are lipid based bilayer vesicles. Versatility in particle size and in the physical parameters of the lipids has resulted in liposomes been widely used as carriers of drugs, peptides, proteins, and nucleic acid molecules for pharmaceutical, cosmetic, and biochemical purposes. Liposomes are composed primarily of vesicle-forming lipids, which may be natural, semi-synthetic or fully synthetic, and neutral, negatively or positively charged. Exemplary vesicle-forming lipids include the sphingolipids, ether lipids, sterols, phospholipids, particularly the phosphoglycerides, and the glycolipids, such as the cerebrosides and gangliosides. Lipids suitable for use in liposomes are known to persons of skill in the art and are cited in a variety of sources, such as 1998 McCutcheon's Detergents and Emulsifiers, 1998 McCutcheon's Functional Materials, both published by McCutcheon Publishing Co., New Jersey, and the Avanti Polar Lipids, Inc. Catalog. In particular examples, the liposomes of the present invention comprise any one or more of 1,2-dioleoyl-sn-glycero-3-phosphocholine (DOPC), 1,2-dioleoyl-sn-glycero-3-phospho-(1'-rac-glycerol) (sodium salt) (DOPG), 1,2-dioleoyl-sn-glycero-3-phospho-L-serine (sodium salt) (DOPS), 1,2-dioleoyl-sn-glycero-3-phosphoethanolamine (DOPE), 1,2-dioleoyl-3-trimethylammonium-propane (chloride salt) (DOTAP), 1,2-dioleoyl-3-dimethylammonium-propane (DODAP), 1,2-distearoyl-sn-glycero-3-phosphoethanolamine-N-[methoxy(polyethylene glycol)-750] (ammonium salt) (DSPE-PEG750), 1-palmitoyl-2-oleoyl-sn-glycero-3-phosphocholine (POPC), or 2-(4,4-Difluoro-5-Methyl-4-Bora-3a,4a-Diaza-s-Indacene-3-Dodecanoyl)-1-Hexadecanoyl-sn-Glycero-3-Phosphocholine (Bodipy). Methods of producing liposomes are well known to those skilled in the art, and have been described extensively elsewhere (for review, see e.g. Wagner and Vorauer-Uhl (2011) J Drug Delivery, Article ID 591325; Yu et al. (2009) Methods Enzymol. 465: 129-141, and Laouini et al. (2012) J Colloid Sci Biotech 1:147-168), 2012.). These methods include, for example, thin-film hydration, detergent dialysis, reverse-phase evaporation, ethanol injection, freeze-drying of a monophase solution, microfluidic hydrodynamic focusing, and supercritical fluid methods.

The chimeric protein may be attached to the nanoparticulate carrier using any method known in the art providing the attachment allows interaction between the chimeric protein and the antigen presenting cells so as to enable binding and internalisation. Accordingly, most typically the chimeric protein is attached so that it is displayed on the surface of the nanoparticulate carrier. Many methods are widely known for attaching proteins to a nanoparticulate carrier, including covalent and non-covalent methods (see e.g. Nobs et al. (2004) J Pharm Sci. 93(8):1980-92; Marques-Gallego and de Kroon (2014) BioMed Research International, Article ID 129458). The protein can be attached to the nanoparticulate carrier during formation of the nanoparticulate carrier, or can be attached to the surface of pre-formed nanoparticulate carriers. For example, the protein can be attached to a lipid and the lipid-protein mixed with other components to prepare the nanoparticulate carrier (see e.g. Surace et al., (2009) Molecular Pharmaceutics 6:1062-1073; Banerjee et al. (2004) International Journal of Cancer 112:693-700). Alternatively, proteins can be ligated to the surface of nanoparticulate carriers by amide conjugation, amine-carboxyl conjugation, disulfide/thioether conjugation or biotin/streptavidin binding. In other examples, "click chemistry" can be utilised, including copper(I)-catalyzed Huisgen 1,3-dipolar cycloaddition (CuAAC) ligation (Hassaneet et al. (2006) Bioconjugate Chemistry 17:849-854), copper-free click chemistry ligation (Koo et al. (2012) Angewandte Chemie: International Edition 51:11836-11840), Staudinger ligation Zhang et al. (2009) Chemical Communications 21:3032-3034) and tetrazine/trans-cyclooctene inverse electron demand Diels-Alder cycloaddition (IEDDA) (Emmetiere et al., (2013) Bioconjugate Chemistry 24:1784-1789).

In particular examples, the chimeric protein comprises a histidine tag, and the protein is engrafted to the liposome via a chelator lipid with one or more nitrilotriacetic acid moieties, such as, but not limited to, nitrilotriacetic acid (NTA) or trinitrilotriacetic acid (3NTA), and a metal ion, such as a nickel (Ni) ion. Typically, the nitrilotriacetic acid moiety is attached to at least one aliphatic chain, which can be of varying length and can be saturated or unsaturated. In particular examples, the nitrilotriacetic acid moiety is attached to one or more aliphatic chains of between 8 and 20 carbons. Non-limiting examples of aliphatic chains include ditetradecylamine (DTDA) chains, Pam2Cys ((S-(2,3-dipalmitate-propyl)cysteine), and Pam3Cys (N-palmitoyl-S-[2,3-bis(palmitoyloxy)propyl]cysteine). Thus, in some examples, the nitrilotriacetic acid moiety is attached to one or more ditetradecylamine (DTDA) chains, resulting in, for example, nitrilotriacetic acid ditetradecylamine (NTA-DTDA) or 3(nitrilotriacetic acid)-ditetradecylamine (3NTADTDA) (Altin et al. (2001) Biochim Biophys Acta 1513(2):131-48; van Broekhaven et al. (2005) Biochimica et Biophysica Acta—Biomembranes 1716: 104-116). In further examples, the nitrilotriacetic acid moiety is attached to Pam2Cys, such as described in WO02006081631. For example, 3NTA attached to Pam2CysSerLys8Cys ($P_2CSK_8C$) produces Lipokel (Pam2CysSerLys8Cys-3NTA). Accordingly, exemplary nanoparticulate carriers of the present invention contain NTA-DTDA, 3NTADTDA, and/or, Pam2CysSerLys8Cys-3NTA.

The nanoparticulate carriers of the present invention may also comprise one or more other entities, such as one or more of a polypeptide, peptide, nucleic acid molecule, or drug, which can be encapsulated within the carrier and/or attached to the surface of the carrier. Particularly contemplated are nanoparticulate carriers that comprise an antigen to which an immune response can be elicited upon administration of the nanoparticulate carrier to a subject. Exemplary antigens include bacterial antigens (e.g. antigens from *Actinomyces, Bacillus, Bacteroides, Bordetella, Bartonella, Borrelia, Brucella, Campylobacter, Capnocytophaga, Chlamydia, Clostridium, Corynebacterium, Coxiella, Dermatophilus, Enterococcus, Ehrlichia, Escherichia, Francisella, Fusobacterium, Haemobartonella, Helicobacter, Klebsiella,* L-form bacteria, *Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Strep-* tococcus and *Yersinia* spp.), viral antigens (e.g. antigens from adenoviruses, caliciviruses, coronaviruses, distemper viruses, hepatitis viruses, herpesviruses, immunodeficiency viruses, infectious peritonitis viruses, leukemia viruses, oncogenic viruses, papilloma viruses, parainfluenza viruses, parvoviruses, rabies viruses, and reoviruses), fungal antigens (e.g. antigens from *Absidia, Acremonium, Alternaria, Aspergillus, Basidiobolus, Bipolaris, Blastomyces, Candida, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon*, and *Xylohypha* spp.), protozoan or parasite antigens (e.g. antigens from *Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, Trypanosoma, Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris. Uncinaria*, and *Wuchereria* spp.), and tumour antigens (e.g. CEA, MHC, CTLA-4, gp100, mesothelin, PD-L1, TRP1, CD40, EGFP, Her2, TCR alpha, trp2, TCR, MUC1, cdr2, ras, 4-1BB, CT26, GITR, OX40, TGF-β. WT1, MUC1, LMP2, HPV E6 E7, EGFRvIII, HER-2/neu, MAGE A3, p53 nonmutant, NY-ESO-1, PSMA, GD2, Melan A/MART1, Ras mutant, gp 100, p53 mutant, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-(3, MAD-CT-2, and Fos-related antigen 1). The antigen may be a polypeptide or peptide (including a glycoprotein or glycopeptide), or a nucleic acid molecule (e.g. DNA or RNA). The antigen can be encapsulated within or attached to the surface of the nanoparticle using any method known to those skilled in the art. In particular examples, the antigen is attached to the surface of the nanoparticulate carrier. The nanoparticulate carriers of the present invention can comprise one or more antigens.

Also contemplated are nanoparticulate carriers comprising one or more other immunomodulating agents, including, for example, other TLR agonists, chemokines, and/or cytokines. TLR agonists include both natural agonists, such as PAMP (pathogen-associated molecular patterns) or DAMP (damage-associated molecular pattern) ligands, and synthetic agonists. TLR agonists for the purposes of the present invention are known in the art and include TLR1/2 agonists (e.g. triacylated lipopeptides, Pam3Cys), TLR2 agonists (e.g. peptidoglycan from Gram positive bacteria, bacterial lipoprotein, lipoteichoic acid, lipopolysaccharide (LPS), GPI-anchor proteins, Neisserial porins, phospholipomannan, CFA, MALP2, Pam2Cys, FSL-1 and Hib-OMPC), TLR3 agonists (e.g. single-stranded and double-stranded viral RNA, poly I:C, poly A:U), TLR4 agonists e.g. LPS, RSV F-protein; mannan, glycoinositolphospholipids, RSV and MMTV envelope proteins, Hsp60, Hsp70, fibronectin domain A, surfactant protein A, hyaluronan, HMGB-1, AGP, MPLA, RC-529, MDF2β and CFA), TLR2/6 agonists (e.g. phenol-soluble modulin, diacylated lipopeptides, LTA, zymosan, MALP-2, Pam2Cys and FSL-1), TLR7 agonists (e.g. viral single-stranded RNA, human RNA, guanosine analogs, and imidazoquinolines (e.g. Imiquimod, Aldara®, R848, Resiquimod®) and loxoribine), TLR8 agonists (e.g. viral single-stranded RNA, human RNA, imidazoquinolines, loxoribine and ssPolyU), TLR9 agonists (dsDNA viruses, hemozoin, unmethylated CpG DNA, human DNA/chromatin, LL37-DNA and CpG-oligonucleotides) and TLR10 agonists. In particular examples, the nanoparticulate carriers include Pam2Cys. For example, the nanoparticulate carrier can include Lipokel, which comprises the lipid moiety $P_2CSK_8C$ coupled to 3NTA via the heterobifunctional linker molecule N-Succinimidyl 6-maleimidocaproate (MCS) (WO2006081631).

Uses and Methods

The nanoparticulate carriers of the present invention that comprise a chimeric protein described herein are of particular use in internalizing an antigen in an antigen presenting cell. Nanoparticulate carriers comprising a chimeric protein of the invention and one or more antigens can be contacted with an antigen presenting cell to facilitate internalization of the nanoparticulate carrier, and thus the antigen, by the antigen presenting cell. In particular examples, the antigen presenting cell is a dendritic cell. Contact between the antigen presenting cell and the nanoparticulate carrier can be performed in vitro or in vivo.

The nanoparticulate carriers of the present invention that comprise a chimeric protein described herein are also of particular use in eliciting an immune response to an antigen carried by the nanoparticulate carrier. Nanoparticulate carriers comprising a chimeric protein and one or more antigens can be administered to a subject in an amount sufficient to elicit an immune response to the antigen. The immune response may be a cellular and/or humoral immune response, and include a $CD4^+$ T cell response, a $CD8^+$ T cell response, a humoral response (i.e. B cells), and/or the induction of proinflammatory cytokines and/or chemokines. In particular instances, the methods elicit at least a $CD8^+$ T cell response.

The nanoparticulate carriers can be formulated in any conventional manner with one or more physiologically acceptable carriers or excipients. Selection of the carrier or excipient is within the skill of the administering profession and can depend upon a number of parameters, such as the mode of administration (i.e., intravenous, intramuscular or any other mode). The nanoparticulate carriers provided herein can be formulated for direct administration or can be formulated for dilution or other modification. Accordingly, the nanoparticulate carriers can be formulated in single (or unit) dosage forms or multiple dosage forms. Examples of single dose forms include ampoules and syringes. Examples of multiple dose forms include vials and bottles that contain multiple unit doses.

Generally, nanoparticulate carriers for therapeutic use are prepared in view of approval from a regulatory agency or otherwise prepared in accordance with generally recognized pharmacopeia for use in animals and in humans. The nanoparticulate carriers can include carriers such as a diluent, excipient, or vehicle. Such pharmaceutical carriers can be sterile liquids, such as water and oils. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A vaccine composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents. Examples of suitable pharmaceutical carriers are described in "Remington's Pharmaceutical Sciences" by E. W. Martin.

The precise amount or dose of the nanoparticulate carrier administered to the subject depends on the amount of antigen loaded on or into the carrier, the antigenicity of the antigen, the type of TLR5 agonist, the route of administration, the number of dosages administered, and other considerations, such as the weight, age and general state of the subject. Particular dosages and administration protocols can be empirically determined or extrapolated from, for example, studies in animal models or previous studies in humans.

The nanoparticulate carriers can be administered by any method and route understood to be suitable by a skilled artisan, including, but not limited to, intramuscular, intradermal, parenteral, intravenous, subcutaneous, intranasal, oral, intraperitoneal or topical administration, as well as by any combination of any two or more thereof, formulated in a manner suitable for each route of administration. The carriers can be administered to a subject one time or more than one time, including 2, 3, 4, 5 or more times. If the vaccines are administered more than one time, the time between dosage administration can be, for example, 1, 2, 3, 4, 5, 6, 7, 8, 9, 10, 11, 12 or more weeks, or 1, 2, 3, 4, 5, 6, 7, 8, 9, 10, 11, 12 or more months. Selecting an optimal vaccination protocol is well within the level of skill of the skilled artisan.

The nanoparticulate carriers, if desired, can be presented in a package, in a kit or dispenser device, such as a syringe with a needle, or a vial and a syringe with a needle, which can contain one or more unit dosage forms. The kit or dispenser device can be accompanied by instructions for administration.

Having generally described the invention, the same will be more readily understood by reference to the following examples, which are provided by way of illustration and are not intended as limiting.

EXAMPLES OF THE INVENTION

Example 1

Materials and Methods

Generation and Purification of FliC-120 Fusion Protein

A FliC-gp120 chimeric protein, Fg115 (SEQ ID NO:5; FIG. 1b) was generated by fusing the FliC gene from *Salmonella typhimurium* (SEQ ID NO:4) in frame and to the 3' end of the HIV gp120 gene (SEQ ID NO:2). A short linker having the sequence ACTAGT (SEQ ID NO:7), which is translated to a threonine-serine dipeptide linker, was included to separate the two coding regions. Included at the 5' end of the fusion protein cassette (translated as the C terminal portion of the fusion protein), was nucleic acid encoding a thrombin cleavage sequence (nucleotide sequence set forth in SEQ ID NO:9; amino acid sequence set forth in SEQ ID NO:8) and a histidine tag (6H; nucleotide sequence set forth in SEQ ID NO:11; amino acid sequence set forth in SEQ ID NO:10).

The resulting fusion protein cassette (SEQ ID NO:6; FIG. 1a) was cloned into the pFastBac plasmid vector for expression using the baculovirus system inSf9 or High Five™ (Life Technologies) insect cells to produce 3 batches of Fg115.

The first batch of Fg115 (2011) recombinant protein was produced at the University of Queensland Protein Expression Facility. Briefly, infected SD cells were cultured in SF900-II medium at 28° C. and harvested 72 hours later. Fg115 protein was purified from the supernatant with a two-step process utilising immobilized metal ion affinity chromatography (IMAC) and ion exchange chromatography (IEX). The IMAC purification utilised a 5 ml HisTrap FF (GE) column, with a binding/washing buffer of 20 mM Tris-HCl, 200 mM Sodium Chloride, 20 mM Imidazole pH 8.5, and elution buffer of 20 mM Tris-HCl, 200 mM Sodium Chloride, 500 mM Imidazole pH 8.5. The IEX purification utilised a 5 ml HiTrap Q FF (GE) column with a binding/washing buffer of 20 mM Tris-HCl, 10 mM Sodium Chloride, pH 8.5 and an elution buffer of 20 mM Tris-HCl, 1M Sodium Chloride, pH 8.5. Two peaks (A and B) were observed, with approximately equal yield for each peak (Peak A fraction: 0.33 mg/mL; Peak B fraction: 0.34 mg/mL).

The second batch of Fg115 (May 2014) was produced by infection of High Five™ cells, which were then cultured in SF900-II medium at 27° C. and harvested 48 hours later. Fg115 protein was purified from the supernatant with a two-step process utilising IMAC and size exclusion chromatography (SEC). The IMAC purification utilised a 5 ml HisTrap FF (GE) column, with a binding/washing buffer of 20 mM NaP, 500 mM NaCl, 60 mM Imidazole, pH 7.0, and elution buffer of 20 mM NaP, 500 mM NaCl, 500 mM Imidazole, pH 7.0. The SEC purification utilised a HiLoad 26/600 Superdex 200 (GE Healthcare) column with PBS buffer. Two peaks (A and B) were observed, with a yield for Peak A of 0.30 mg/mL and Peak B of 0.58 mg/mL.

The third batch of Fg115 (July 2014) was also produced by infection of High Five™ cells, which were then cultured in SF900-II medium at 27° C. and harvested 66 hours later. The supernatant was first concentrated using a 50 kDa MWCO Hydrosart ultrafiltration cassette (Sartorius Crossflow Systems) before the Fg115 protein was purified with a two-step process utilising IMAC and SEC. The IMAC purification utilised a 5 ml HisTrap FF (GE) column, with a binding/washing buffer of 20 mM NaP, 500 mM Sodium Chloride, 80 mM Imidazole pH 7, and elution buffer of 20 mM NaP, 500 mM NaCl, 700 mM Imidazole, pH 7.0. The SEC purification utilised a HiLoad 26/600 Superdex 200 (GE Healthcare) column with PBS buffer. Two peaks (A and B) were observed, with a yield for Peak A of 0.88 mg/mL and Peak B of 0.1.16 mg/mL.

Figure 1D:
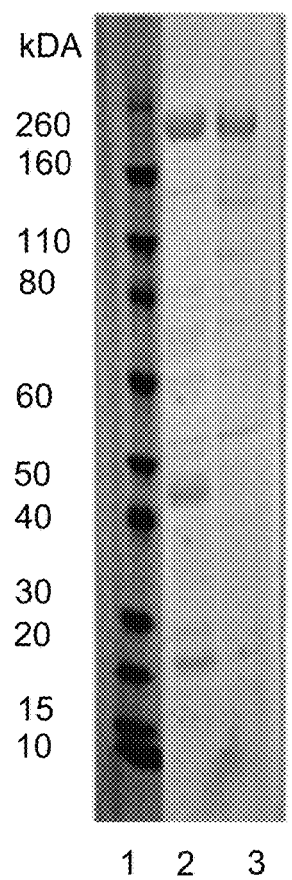

FIG. 1c is a schematic of the Fg115 chimeric protein showing the 12 potential N-glycosylation sites in the gp120 polypeptide. The expected molecular weight of the chimeric protein (by sequence) is about 110 kDa. With glycosylation during expression in insect cells, the Fg115 protein has a much higher apparent molecule weight (FIG. 1d).

Preparation of Liposomes

For the studies described below, five types of liposomes were prepared: stock liposomes with no internal cargo, for the analysis of Fg115 engraftment; fluorescent liposomes prepared with the fluorescent tracer β-BODIPY® 500/510 C12-HPC for binding/targeting and internalisation studies; liposomes prepared with a cargo of NT-FITC peptide (this is a synthetic neurotensin peptide that carries the fluorescent label FITC); liposomes prepared with an internal cargo of SIINFEKL peptide; liposomes prepared with an internal cargo of chicken egg albumin (ovalbumin or OVA) protein.

Lipids were purchased from Avanti Polar Lipids and included 1,2-dioleoyl-sn-glycero-3-phosphocholine (DOPC), 1,2-dioleoyl-sn-glycero-3-phospho-(1'-rac-glycerol) (sodium salt) (DOPG), 1,2-dioleoyl-sn-glycero-3-phospho-L-serine (sodium salt) (DOPS), 1,2-dioleoyl-sn-glycero-3-phosphoethanolamine (DOPE), 1,2-dioleoyl-3-trimethylammonium-propane (chloride salt) (DOTAP), 1,2-dioleoyl-3-dimethylammonium-propane (DODAP), 1,2-distearoyl-sn-glycero-3-phosphoethanolamine-N-[methoxy (polyethylene glycol)-750] (ammonium salt) (DSPE-PEG750), 1-palmitoyl-2-oleoyl-sn-glycero-3-phosphocholine (POPC), or 2-(4,4-Difluoro-5-Methyl-4-Bora-3a,4a-Diaza-s-Indacene-3-Dodecanoyl)-1-Hexadecanoyl-sn-Glycero-3-Phosphocholine (Bodipy).

TLR4 agonist Monophosphoryl Lipid A (synthetic) (PHAD) (MPLA (PHAD)) (Avanti Polar lipids) and TLR 2 agonist Lipokel (Pam2Cys-3NTA) (in house reagent) were also used in some liposome preparations.

Preparation of Hand-Shaken 48 mM Lipid Vesicles for Extrusion

In general liposomes were prepared as follows. Stock solutions of the constituent lipids were prepared in volatile solvents (chloroform or ethanol), and were mixed at the correct ratios and volumes in a round bottomed flask of appropriate volume, then dried to a thin film using a rotary evaporator. The thin film was rehydrated in a solution of either saline or PBS, or either of these solutions containing a cargo protein or peptide as described below. The film was rehydrated by gentle hand shaking, which produced a suspension of multi-lamellar vesicles (MLVs) of diverse size. The MLVs were resized by extrusion through a polycarbonate membrane with pores of a defined size (typically 0.2 pm), either using a simple manual syringe-driven extruder (such as an Avanti Polar Lipids "Mini extruder"), or a nitrogen gas-driven extrusion system (such as a Northern lipids "Lipex" extruder), essentially according to manufacturer's instructions.

Specifically, 1000 mL flasks were prepared by removing endotoxin and any traces of residual lipids, by treatment with a 0.5% solution of E-Toxa Clean (SIGMA) for a minimum of 2 hours (preferably overnight). The E-Toxa clean solution was discarded and the flask rinsed with copious amounts of tap water then 5 volumes of MilliQ water. Finally, the flask was rinsed with ~50 mL of ethanol before being air dried.

To prepare the dried lipid film, the appropriate lipids were removed from storage and allowed to stand at room temperature (RT) for 30 minutes. As needed, the correct amount of DOPC (Avanti Polar Lipids) was dissolved in 15 mL of chloroform in a clean 20 mL amber glass vial; the correct amount of DOPG (Avanti Polar lipids) was dissolved in 15 mL of chloroform in a clean 20 mL amber glass vial; the correct amount of DSPE-PEG750 (Avanti Polar Lipids) was dissolved in 5 mL of chloroform in a clean 20 mL amber glass vial; and the correct volume of 3NTA-DTDA stock (7.1 mg/mL in ethanol) was added to the treated 1000 mL flask. The lipids were then added to the 1000 mL flask containing the 3NTA-DTDA and all amber glass vials were rinsed 3 times with ~2 mL of chloroform, and this chloroform was also added to the 1000 mL flask.

The solvent was then removed using a rotary evaporator, with the water bath set at 42° C., and adjusted to 400-600 mmHg of vacuum, until a thin film of dried lipids was deposited on the walls of the flask. If the lipid film was not uniform, or contained a large amount of air bubbles, the film was redissolved in 5-10 mL of chloroform and dried again on a rotary evaporator. When there was no more visible solvent left in flask, the rotary evaporator vacuum was increased to maximum (~600 mmHg) for 10 minutes, and the flask removed from the rotary evaporator and transferred to a vacuum oven set at 42° C. for a minimum of 2 hours (preferably overnight) to remove all residual traces of chloroform.

To reconstitute the dried lipid film, PBS and $NiSO_4$ stocks were added to a 50 mL tube and warmed to 37° C. The PBS/$NiSO_4$ solution was added to the flask containing the dried lipids and swirled gently for 30 minutes to rehydrate the lipids. If there was still lipids visible on the walls of the flask after 30 minutes, swirling was continued until they were dissolved. The liposomes were then extruded 5 times through a 0.4 μm, then 10 times through a 0.2 μm PC membrane using a Northern Lipids "Lipex" extruder with a 10 mL thermobarrel warmed to 52° C., essentially according to manufacturer's instructions. For material to be used in vivo, an additional filtration step using a sterile 0.2 μm filter and sterile syringe was performed.

Preparation of Peptide-Containing Liposomes

To generate liposomes that carried a peptide cargo (e.g. NT-FITC or SIINFEKL) cargo, a thin lipid film was prepared by adding lipid stocks in chloroform/ethanol to a round bottomed flask (10-50 mL volume), and removing the solvents using a rotary evaporator. The thin lipid film was rehydrated in a solution of peptide in PBS, by gentle hand shaking, which produced a suspension of MLVs of diverse size. The MLVs were resized by extrusion through a polycarbonate membrane with pores of a defined size (typically 0.2 μm), either using an Avanti Polar Lipids "Mini extruder" or a Northern lipids "Lipex" extruder. The resized liposomes were then dialysed using 300 kDa MWCO tubing to remove any unencapsulated peptide. Peptide content of the dialysed liposomes was determined by HPLC and/or fluorescence analysis of the sample using a Nanodrop instrument.

Specifically, the dried lipid film was prepared as described above. Peptide solutions (SIINFEKL or NT-FITC) at pH 7.5-8 were used as required. The appropriate volume of peptide was added to the flask containing the dried lipids and the flask was swirled gently for 30 minutes to rehydrate the lipids. If there were still lipids visible on the walls of the flask after 30 minutes, swirling was continued until they dissolved.

The liposomes were then extruded 5 times through a 0.2 μm PC membrane using a Northern Lipids "Lipex" extruder with a 10 mL thermobarrel warmed to 52° C., essentially according to manufacturer's instructions. The extruded liposomes were loaded into lengths of 300 kDa MWCO tubing, with the ends secured with 'Universal' Nylon dialysis closures, and dialysed against at least 100 volumes of saline for 2 hours, then overnight at 4° C. in refreshed saline. The amount of peptide present in the liposomes was determined by HPLC, by comparison with peptide standards. Typically, a C18 analytical column (Grace Everest 300A C18 5 μm 100 mm×2.1 mm) and a water/acetonitrile gradient was used, with both solvents containing 0.1% trifluoroacetic acid (TFA).

Preparation of OVA Liposomes

To generate liposomes that carried an OVA cargo, a thin lipid film was prepared as described above before being was rehydrated in a solution of 1.5 mg/mL OVA in PBS, by gentle hand shaking for 30 minutes, which produced a suspension of MLVs of diverse size. The MLVs were resized by extrusion 5 times through a 0.2 μm PC membrane using a Northern Lipids "Lipex" extruder with a 10 mL thermo-barrel warmed to 52° C., essentially according to manufacturer's instructions. The extruded liposomes were loaded into lengths of 300 kDa MWCO tubing, with the ends secured with 'Universal' Nylon dialysis closures, and dialysed against at least 100 volumes of saline for 2 hours, then overnight at 4° C. in refreshed saline. OVA content was determined by Silver-stained SDS-PAGE gel, by comparing the OVA content of dialysed liposomes with standards using QuantIT gel analysis software.

Engraftment of Liposomes

Liposomes prepared as described above were engrafted with histidine tagged proteins (e.g. Fg115, FliC-6his, or gp120-6his) as required. The amount of protein that can be engrafted was determined empirically. An important assumption is that at most, only 50% of the 3NTA-DTDA molecules are able to complex his-tagged molecules (because the other 50% will be facing the internal aqueous compartment of the liposome). Briefly, the required amount of extruded liposomes was transferred into a clean tube and the appropriate amount of histidine-tagged protein was then added. The formulation was made up to the desired volume with PBS if necessary. The formulation was mixed by inversion and incubated overnight at room temperature (in the dark for BODIPY-containing formulations) or 4° C.

Example 2

Targeting of Fg115-engrafted Liposomes to Human Monocyte-derived Dendritic Cells The binding of Fg115-engrafted liposomes to human monocyte derived dendritic cells (moDCs) was assessed by FACS, as described above in Example 1. Briefly, chelating liposomes were produced at 24 mM total lipid with 0.25% 3NTADTDA and the fluorescent tracer β-BODIPY 500/510 C12-HPC (0.2%), with a lipid backbone of DOPC, DOPG (30%) and DSPE-PEG750 (2.5%). Liposomes were engrafted with 100 μg/mL Fg115 protein, 10 μg/mL FlgT peptide (SEQ ID NO: 12; a Flagellin derived peptide—Auspep Pty Ltd), 50 μg/mL DC-SIGN-specific antibody DMS5000 (Domantis Ltd) or left unengrafted. The final lipid content of the engrafted liposomes was 3.6 mM.

Figure 2:
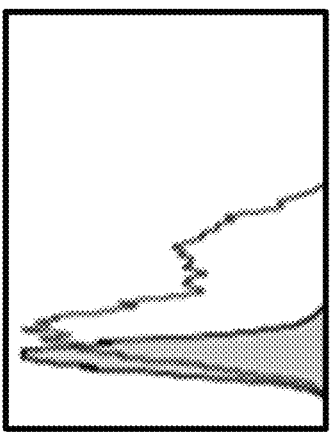
FIG. 2 shows FACs analysis human monocyte-derived dendritic cells (moDCs) that were cultured with liposomes engrafted with Fgl15, FlgT or the DMS5000 antibody, or unengrafted liposomes.
Figure 2:
Figure 2:
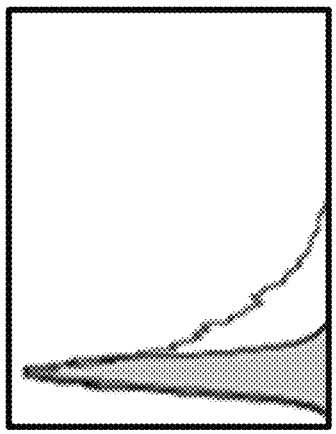
Figure 2:
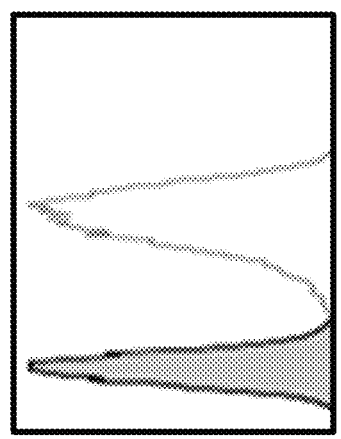
Figure 2:
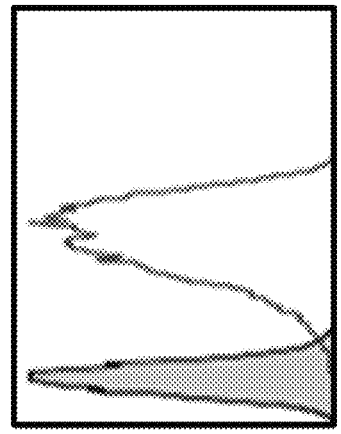

Ten μL liposomes were added to 50,000 moDCs and the mixture was incubated on ice for 30 minutes to 1 hour, protected from light. The cells were gently washed with PBS and binding of liposomes to the cells was then analysed by FACS (FIG. 2), and targeting of the liposomes was assessed based on mean fluorescence intensity (MFI) values. It was observed that Fg115-engrafted liposomes bound to moDCs with higher efficiency (MFI of 27.7) than unengrafted liposomes (MFI of 9.7). Liposomes engrafted with the related FlgT peptide do not exhibit this enhanced binding (MFI of 16.3), while liposomes engrafted with DMS5000 showed strong binding (MFI of 143).

Example 3

Internalisation of Fg115-engrafted Liposomes

Figure 3A:
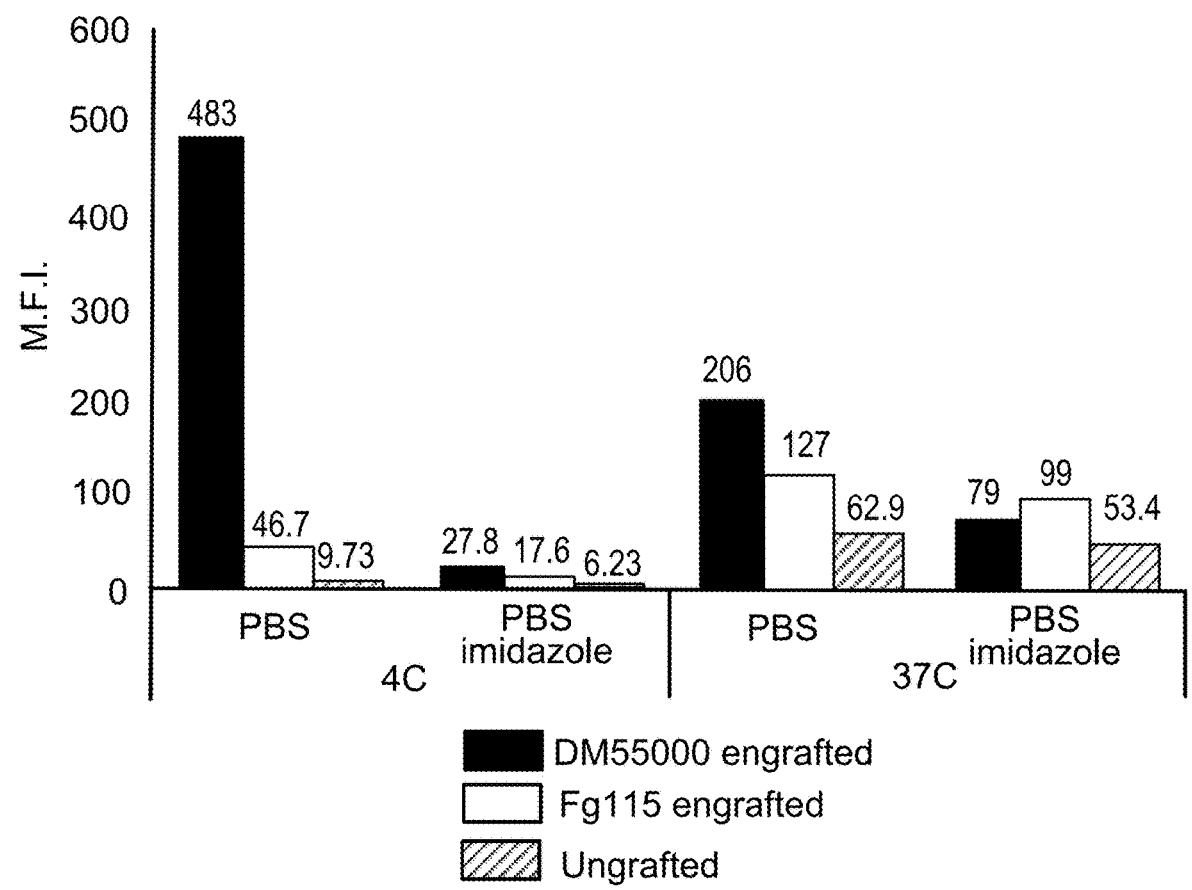
FIG. 3 shows the results of two studies assessing the internalisation of Fgl15-engrafted liposomes by human moDCs. Liposomes engrafted with Fgl15, DMS5000, or unengrafted liposomes, were cultured with human moDCs at 4° C. or 37° C. Cell-liposome mixtures were then washed either with PBS or PBS/imidazole and analysed by FACS. MFI reflecting internalised liposomes from a first donor (A) and a second donor (B) are shown.
Figure 3B:
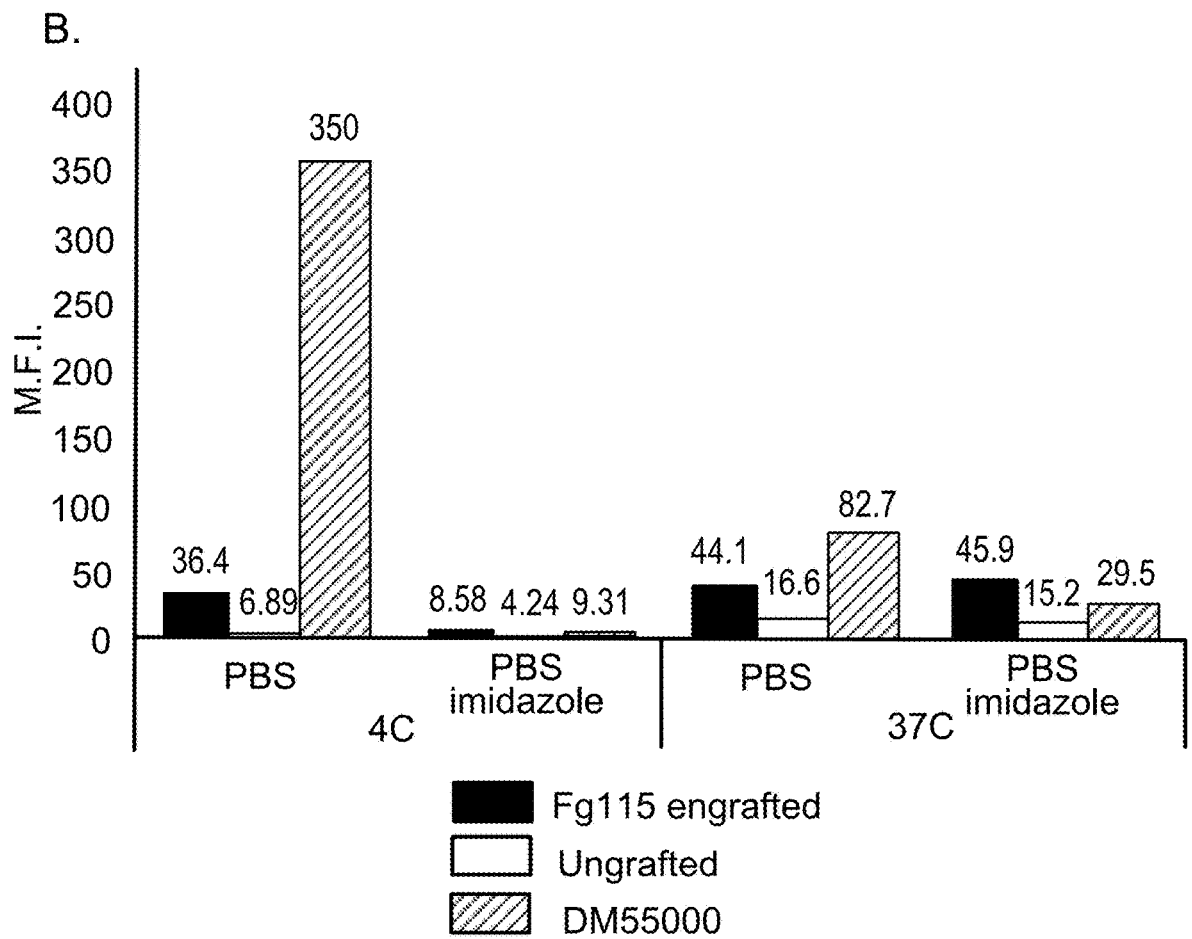

The internalisation of Fg115-engrafted liposomes into human moDCs cells in vitro was assessed FACS, as described above in Example 1. Briefly, chelating liposomes were produced at 24 mM total lipid with 0.25% 3NTADTDA and the fluorescent tracer β-BODIPY 500/510 $C_{12}$-HPC (0.2%). The lipid backbone used for the liposomes was DOPC, DOPG (30%) and DSPE-PEG750 (2.5%). Liposomes were engrafted with 100 μg/mL Fg115 protein, 50 μg/mL DMS5000, or left unengrafted. Liposomes were added to either pre-chilled moDCs (minimal internalisation expected) or moDCs maintained at 37° C. (20 μL of engrafted liposomes mixed with 50,000 cells) and the mixtures were incubated at 4° C. or 37° C., respectively, protected from light for 2 hours. Cell-liposome mixtures were then washed either with PBS or PBS/imidazole and analysed by FACS. PBS washes enable the assessment of cell-associated (i.e. surface-associated or internalized) liposomes, while PBS/imidazole washes away surface-associated liposomes so that the MFI of these cells reflects internalised liposomes only. As shown by the MFI values of FACs analysis from two separate experiments using moDCs from different donors (FIGS. 3A and 3B), there was negligible association and minimal internalisation of unengrafted liposomes at 4° C., as expected. When Fg115 was engrafted on the surface of liposomes, increased binding of the liposomes to moDC was detected at 4° C. (approximately 3-fold increase). These liposomes could be stripped away from cells maintained at 4° C., as shown by the MFI of Fg115-liposome-cell mixtures washed with PBS/imidazole. At 37° C., higher levels of fluorescence were found associated with all cells and most of this appeared to be the result of internalisation. These results clearly show an enhanced internalisation of Fg115-engrafted liposomes compared to unengrafted liposomes.

Example 4

The Effect of Fg115 Density on the Internalisation of Fg115-engrafted Liposomes to Human moDCs Cell Liposomes were engrafted with 100 μg/mL or 50 μg/mL Fg115 protein to assess the effect of Fg115 density on internalization. Briefly, chelating liposomes were produced at 24 mM total lipid with 0.25% 3NTADTDA and the fluorescent tracer β-BODIPY 500/510 $C_{12}$-HPC (0.2%). The lipid backbone was DOPC (67.05%), DOPG (30%) and DSPE-PEG750 (2.5%). Liposomes were engrafted with 100 μg/mL or 50 μg/mL Fg115 protein, 25 μg/mL, 50 μg/mL or 75 μg/mL DMS5000 or left unengrafted. Final lipid content was 3.6 mM. Liposomes were then added to moDCs from two donors (20 μL of engrafted liposomes mixed with 50,000 cells). The moDCs were either pre-chilled or maintained at 37° C., and the mixtures were incubated at the relevant temperature protected from light for 2 hours. Cell-liposome mixtures were then washed either with PBS or PBS/imidazole and analysed by FACS.

Increased internalisation of Fg115-engrafted liposomes compared to unengrafted liposomes was observed with moDCs prepared from multiple donors, with MFI values for Fg115-engrafted liposomes approximately double those of the unengrafted liposomes under the same conditions (data not shown). Furthermore, internalisation was enhanced by approximately 25-40% when liposomes were engrafted at 100 μg/mL Fg115 compared to 50 μg/mL, indicating that increased Fg115 density on the surface of liposomes increased liposome binding to moDCs and enhanced liposome internalisation.

Example 5

Binding of Liposomes Engrafted with Different Fractions of Fg115-engrafted Liposomes Two peaks (labeled A and B) are typically detected when Fg115 is purified as described in Example 1. Fg115 from peaks A and B was isolated following expression in High Five insect cells and assessed separately for its ability to enhance internalization of engrafted lipids. Briefly, chelating liposomes were produced at 24 mM total lipid with 0.25% 3NTADTDA and the fluorescent tracer β-BODIPY 500/510 $C_{12}$-HPC (0.2%). The lipid backbone was DOPC (67.05%), DOPG (30%) and DSPE-PEG750 (2.5%). Liposomes were engrafted with the Fg115 protein at final concentrations ranging from 10 to 90 mg/mL (or unengrafted) to produce the formulations shown in Table 1 below.

Twenty μL liposomes were added to 50,000 moDCs from one of two donors, and the mixtures were incubated on ice protected from light. Binding of liposomes to the cells was analysed by FACS binding and MFI values were determined. It was observed that Fg115 from Peak B appeared to facilitate improved binding compared to Fg115 from peak A (Table 1). A dose effect was also confirmed over a range of doses.

TABLE 1

| | Liposome formulations | | | | Binding to cells | |
|---|---|---|---|---|---|---|
| Fg115 Peak | % 3NTADTDA | Fg115 μg/mL | Final total lipid (mM) | total volume μL | MFI (donor 1) | MFI (donor 2) |
| Peak A | 0.25 | 90.0 | 3.6 | 50 | 13.5 | 7.63 |
| Peak B | 0.25 | 92.8 | 3.6 | 50 | 24.9 | 12.6 |
| Peak B | 0.25 | 46.4 | 3.6 | 50 | 21.7 | 10.8 |
| Peak B | 0.25 | 23.2 | 3.6 | 50 | 18.2 | 9.1 |
| Peak B | 0.25 | 11.6 | 3.6 | 50 | 14.9 | 7.87 |
| unengrafted | 0.25 | 0 | 3.6 | 50 | 6.79 | ND |

Example 6

Binding of Peak B Fg115-engrafted Liposomes to CD11c+ Cells

Binding of Fg115-engrafted liposomes to CD11c+ cells from C57/B16 DC-SIGN transgenic mice was assessed using peak B Fg115. Briefly, chelating liposomes were produced at 24 mM total lipid with 0.25% 3NTADTDA and the fluorescent tracer β-BODIPY 500/510 $C_{12}$-HPC (0.2%). The lipid backbone was DOPC (67.05%), DOPG (30%) and DSPE-PEG750 (2.5%). Liposomes were engrafted with the Fg115 protein expressed from High Five cells at final concentrations ranging from 10 to 90 μg/mL, or DMS5000 at 0.75 or 75 μg/mL, to produce the liposome formulations shown in Table 2 below.

TABLE 2

| Liposome | % 3NTADTDA | total volume μL | Fg115 μg/mL | Final total lipid (mM) |
|---|---|---|---|---|
| Fg115 peak B | 0.25 | 200 | 92.8 | 3.6 |
| Fg115 peak B | 0.25 | 200 | 46.4 | 3.6 |
| Fg115 peak B | 0.25 | 200 | 23.2 | 3.6 |
| Fg115 peak B | 0.25 | 200 | 11.6 | 3.6 |
| DMS5000 | 0.25 | 200 | 75 | 3.6 |
| DMS5000 | 0.25 | 200 | 0.75 | 3.6 |
| Unengrafted | 0.25 | 200 | 0.0 | 3.6 |

Liposomes were added to CD11c+ cells purified from the spleen of C57B1/6 DC-SIGN transgenic mice (20 μL of liposomes mixed with 50,000 cells) and the mixtures were incubated on ice protected from light for 1 hour. Binding of liposomes to the cells was analysed by FACS. It was observed that Fg115-engraftment improved the binding of liposomes to CD11c+ cells (data not shown). Engraftment of DMS5000 improved binding even at low engraftment levels of 0.75 μg/mL.

Example 7

Internalisation of Peak B Fg115-engrafted Liposomes by Human moDCs Cells

Internalisation of liposomes engrafted with Fg115 from peak B was assessed using human moDCs. Briefly, chelating liposomes were produced at 24 mM total lipid with 0.25% 3NTADTDA and the fluorescent tracer β-BODIPY 500/510 $C_{12}$-HPC (0.2%). The lipid backbone was DOPC (67.05%), DOPG (30%) and DSPE-PEG750 (2.5%). Liposomes were engrafted with the Fg115 protein from peak B of protein expressed in High Five cells, or DMS5000 at 0.75 or 75 μg/mL, to produce the liposome formulations shown in Table 3 below.

TABLE 3

| Liposome | % 3NTADTDA | total volume μL | Fg115 μg/mL | Final total lipid (mM) |
|---|---|---|---|---|
| Fg115 peak B | 0.25 | 200 | 92.8 | 3.6 |
| Fg115 peak B | 0.25 | 200 | 46.4 | 3.6 |
| Fg115 peak B | 0.25 | 200 | 23.2 | 3.6 |
| Fg115 peak B | 0.25 | 200 | 11.6 | 3.6 |
| DMS5000 | 0.25 | 200 | 75 | 3.6 |
| DMS5000 | 0.25 | 200 | 0.75 | 3.6 |
| Unengrafted | 0.25 | 200 | 0.0 | 3.6 |

Twenty μL liposomes were added to 50,000 moDCs from one of two donors (donor 1 or donor 2), where the cells were either pre-chilled or maintained at 37° C., and the mixtures were incubated at the relevant temperature protected from light for 20 minutes. Cell-liposome mixtures were then washed either with PBS or PBS/imidazole and analysed by FACS. MFI values representing liposomes internalized in donor 1 and donor 2 moDCs are shown in Table 4. The data indicate that engraftment of peak B Fg115 at the highest Fg115 density tested (90 μg/mL) improves internalisation of liposomes by up 10 times, depending on the donor cells. Whilst targeting of liposomes to moDCs by DMS5000 was highly efficient, higher levels of internalisation were observed with Fg115-engrafted liposomes.

TABLE 4

|  | MFI (donor 1) | | MFI (donor 2) | |
| --- | --- | --- | --- | --- |
| Liposome | Internalisation | Targeting | Internalisation | Targeting |
| Fg115 peak B 92 μg/mL | 41.9 | 43.9 | 83.6 | 48.9 |
| Fg115 peak B 46 μg/mL | 3.01 | 42.9 | 52.9 | 35.7 |
| Fg115 peak B 23 μg/mL | 18.2 | 31.7 | 33.6 | 26.1 |
| Fg115 peak B 11.5 μg/mL | 15.6 | 24 | 24.1 | 27.4 |
| DMS5000 75 μg/mL | 10.1 | 165 | 13.9 | 375 |
| DMS5000 0.75 μg/mL | 6 | 11.5 | 9.1 | 17.4 |
| Unengrafted | 5.3 | 5 | 7.6 | 4.8 |

Example 8

Internalisation of Fluorescent Fg115-engrafted Liposomes

The internalization of Fg115-engrafted liposomes was assessed using liposomes with NT-FITC as the fluorescent tracer as part of the internal aqueous cargo rather than the lipid bilayer. Briefly, chelating liposomes were produced at 24 mM total lipid with 0.25% 3NTADTDA and the fluorescent tracer β-BODIPY 500/510 $C_{12}$-HPC (0.2%). The lipid backbone was DOPC (67.05%), DOPG (30%) and DSPE-PEG750 (2.5%). Similar liposomes with NT-FITC instead of β-BODIPY 500/510 $C_{12}$-HPC were also prepared. Liposomes were engrafted with the Fg115 protein to produce the liposome formulations shown in Tables 5 and 6 below.

TABLE 5

| BODIPY liposomes | | | |
| --- | --- | --- | --- |
| % 3NTADTDA | total volume μL | Fg115 μg/mL | Final total lipid (mM) |
| 0.25 | 60 | 60 | 12 |
| 0.25 | 60 | 50 | 12 |
| 0.25 | 60 | 40 | 12 |
| 0.25 | 60 | 20 | 12 |
| 0.25 | 60 | 10 | 12 |
| 0.25 | 60 | 0 | 12 |

TABLE 6

| NT-FITC liposomes | | | |
| --- | --- | --- | --- |
| % 3NTADTDA | total volume μL | Fg115 μg/mL | Final total lipid (mM) |
| 0.25 | 180 | 50 | 4 |
| 0.25 | 180 | 0 | 4 |

Twenty μL liposomes were added to 50,000 moDCs from one of two donors (donor 3 or donor 2), where the cells were either pre-chilled or maintained at 37° C., and the mixtures were incubated at the relevant temperature protected from light for 20 minutes. Cell-liposome mixtures were then washed either with PBS or PBS/imidazole and analysed by FACS. MFI values representing internalized liposomes are shown in Table 7. The enhanced internalisation observed with Fg115-engrafted BODIPY lioposomes (Table 7) was confirmed with Fg115-engrafted NT-FITC liposomes (Table 8). DMS5000 engrafted liposomes, whilst targeting moDCs with greater efficiency, showed lower internalisation than Fg115-engrafted liposomes.

TABLE 7

|  | MFI | |
| --- | --- | --- |
| Liposome | Donor 3 | Donor 2 |
| Fg115 60 μg/mL | 38.3 | 72.6 |
| Fg115 50 μg/mL | 34.4 | 61.8 |
| Fg115 40 μg/mL | 30.6 | 54.5 |
| Fg115 20 μg/mL | 21.5 | 33.9 |
| Fg115 10 μg/mL | 12.8 | 18.2 |
| Unengrafted | 5.9 | 9 |

TABLE 8

|  | MFI (donor 2) | | MFI (donor 3) | |
| --- | --- | --- | --- | --- |
| Liposome | Internalisation | Targeting | Internalisation | Targeting |
| Fg115 50 μg/mL | 37.2 | 17.4 | 13.6 | 9.4 |
| DMS5000 | 13.8 | 112 | 7.2 | 78.9 |
| Unengrafted | 3 | 5.9 | 2.4 | 2.5 |

Example 9

Internalisation of Fg115-admixed Liposomes by Human moDCs Cells

The effect of admixing Fg115 with the liposomes was assessed by mixing Fg115 with liposomes that contained no 3NTADTDA (i.e. non-chelating liposomes), and comparing internalization of these liposomes to Fg115-engrafted liposomes. Briefly, chelating liposomes were produced at 24 mM total lipid with 0.25% 3NTADTDA and the fluorescent tracer β-BODIPY 500/510 $C_{12}$-HPC (0.2%). The lipid backbone was DOPC (67.05%), DOPG (30%) and DSPE-PEG750 (2.5%). Non-chelating liposomes with no 3NTADTDA were also prepared. Chelating and non-chelating liposomes were then mixed with the Fg115 protein to produce the liposome preparations shown in Table 9.

Liposomes were added to either pre-chilled moDCs or moDCs maintained at 37° C. (20 μL of liposomes mixed with 50,000 cells) and the mixtures were incubated at the relevant temperature protected from light for 20 minutes. Cell-liposome mixtures were then washed either with PBS or PBS/imidazole and analysed by FACS. As demonstrated by the MFI values presented in Table 9, the internalization of liposomes admixed with Fg115 was no greater or only marginally greater, depending on the concentration of Fg115, than unengrafted (no Fg115) liposomes, indicating that increased internalisation of liposomes is dependent upon the attachment of Fg115 to the liposomes via 3NTADTDA.

TABLE 9

| Liposome type | Formulation | | | | Internalisation (MFI) |
|---|---|---|---|---|---|
| | Engraftment Details | total Volume | Fg115 µg/mL | Final total lipid | |
| 0.25% 3NTADTDA | Unengrafted | 100 | 0.00 | 4 | 9.1 |
| 0.25% 3NTADTDA | Fg115 | 100 | 50 | 4 | 57.2 |
| NO 3NTADTDA | Fg115 | 100 | 50 | 4 | 18.9 |
| NO 3NTADTDA | Fg115 | 100 | 25 | 4 | 13.7 |
| NO 3NTADTDA | Fg115 | 100 | 12.5 | 4 | 12.7 |
| NO 3NTADTDA | Unengrafted | 100 | 0 | 4 | 10.8 |

Example 10

Internalisation of Peak A or B Fg115-admixed Liposomes by Human moDCs

The effect of admixing Fg115 from peak A or peak B with the liposomes was assessed. Briefly, chelating liposomes were produced at 24 mM total lipid with 0.25% 3NTADTDA and the fluorescent tracer β-BODIPY 500/510 C12-HPC (0.2%). The lipid backbone was DOPC (67.05%), DOPG (30%) and DSPE-PEG750 (2.5%). Liposomes were then mixed with the Fg115 protein from peak A or the Fg115 protein from peak B in the presence or absence of $NiSO_4$ to produce the engrafted or admixed liposomes, respectively, shown in Table 10.

Liposomes were added to either pre-chilled moDCs or moDCs maintained at 37° C. (20 µL of liposomes mixed with 50,000 cells) and the mixtures were incubated at the relevant temperature protected from light for 20 minutes. Cell-liposome mixtures were then washed either with PBS or PBS/imidazole and analysed by FACS. As demonstrated by the MFI values presented in Table 10, liposomes admixed with either peak A or peak B Fg115 exhibited similar internalization into moDCs as unengrafted liposomes, and only Fg115-engrafted liposomes exhibited enhanced internalization.

TABLE 10

| Liposomes | Engraftment details | | | | Internalisation (MFI) |
|---|---|---|---|---|---|
| | % 3NTADTDA | total vol. | Fg115 µg/mL | Final lipid (mM) | |
| Unengrafted | 0.25 | 100 | 0.0 | 3.6 | 1.9 |
| Fg115 Peak A | 0.25 | 100 | 45 | 3.6 | 18.3 |
| Fg115 Peak B | 0.25 | 100 | 45 | 3.6 | 28.2 |
| Fg115 peak A ADMIX | 0.25 | 100 | 45.0 | 3.6 | 2.6 |
| Fg115 peak B ADMIX | 0.25 | 100 | 46.4 | 3.6 | 4.3 |

Example 11

Internalisation by Human moDCs of Liposomes Engrafted with Fg115 or Fg115 Components The internalization of liposomes engrafted with the chimeric Fg115 protein, or the components of the Fg115 protein, was assessed using human moDCs. Briefly, chelating liposomes were produced at 24 mM total lipid with 0.25% 3NTADTDA and the fluorescent tracer β-BODIPY 500/510 C12-HPC (0.2%). The lipid backbone was DOPC (67.05%), DOPG (30%) and DSPE-PEG750 (2.5%). Liposomes were then engrafted in 50 µL total volume with Fg115, histidine-tagged FliC (FliC-6his), histidine tagged gp120 (gp120-6his), or FliC-6his and gp120-6his proteins, to produce the liposome preparations set forth in Table 11. FliC-6his was produced in *E. coli* and gp120-6his was produced in SF9 cells.

Liposomes were added to moDCs maintained at 37° C. (20 µL of liposomes mixed with 50,000 cells) and the mixtures were incubated protected from light for 20 minutes. Cell-liposome mixtures were then washed either with PBS or PBS/imidazole and analysed by FACS. As shown by the MFI values (Table 11), improved internalisation of liposomes was seen only when the liposomes were engrafted with the Fg115 chimeric protein and not when liposomes were engrafted with either FliC or gp120, or both.

TABLE 11

| Liposomes | Engraftment details | | | | Internalisation (MFI) | |
|---|---|---|---|---|---|---|
| | Fg115 µg/mL | FliC µg/mL | gp120 µg/mL | Final total lipid (mM) | PBS | imidazole |
| Unengrafted | 0 | 0 | 0 | 5 | 22.2 | 14.8 |
| Fg115 | 25 | 0 | 0 | 5 | 196 | 156 |
| FliC-6his | 0 | 11.52 | 0 | 5 | 21 | 14.6 |
| gp120-6his | 0 | 0 | 13.72 | 5 | 60.3 | 39.4 |
| FliC-6his/ gp120-6his | 0 | 11.52 | 13.72 | 5 | 54.8 | 36.6 |

Example 12

Internalisation by CD11c+ Cells of Liposomes Engrafted with Fg115 or Fg115 Components The internalization of liposomes engrafted with the chimeric Fg115 protein, or the components of the Fg115 protein, was assessed using CD11c+ cells from wild-type mice or DC-SIGN transgenic mice. Briefly, chelating liposomes were produced at 24 mM total lipid with 0.25% 3NTADTDA and the fluorescent tracer β-BODIPY 500/510 C12-HPC (0.2%). The lipid backbone was DOPC (67.05%), DOPG (30%) and DSPE-PEG750 (2.5%). Liposomes were then engrafted with Fg115, FliC-6his, gp120-6his, or FliC-6his and gp120-6his, to produce the liposome preparations set forth in Table 12. FliC was produced in *E. coli* and gp120 was produced in SF9 cells.

TABLE 12

| Engraftment Details | total volume µL | Fg115 µg/mL | FliC µg/mL | gp120 µg/mL | Final total lipid (mM) |
|---|---|---|---|---|---|
| Unengrafted | 100 | 0 | 0 | 0 | 5 |
| Fg115 | 100 | 25 | 0 | 0 | 5 |
| Fg115 | 100 | 50 | 0 | 0 | 5 |
| FliC | 100 | 0 | 23.04 | 0 | 5 |
| gp120-his | 100 | 0 | 0 | 27.43 | 5 |
| FliC/gp120-his | 100 | 0 | 23.04 | 27.43 | 5 |

Liposomes were added to CD11c+ cells prepared from the spleens of wild-type or DC-SIGN transgenic C57/Bl6 mice. Cells were maintained at 37° C., and 20 µL of liposomes were mixed with 50,000 cells. The mixtures were then incubated protected from light for 20 minutes. Cell-liposome mixtures were then washed either with PBS or PBS/ imidazole and analysed by FACS. Improved internalisation of Fg115-engrafted liposomes was evident only when using DC-SIGN transgenic CD11c+ cells, and not with wild-type mouse cells that do not display human DC-SIGN (Table 13). Engraftment of other proteins (FliC and gp120) did not have the same enhanced internalisation effect.

TABLE 13

| Liposomes | Internalisation (MFI) wild-type cells | | Internalisation (MFI) DC-SIGN transgenic CD11c+ cells | |
|---|---|---|---|---|
| | PBS | imidazole | PBS | imidazole |
| Unengrafted | 79.4 | 80.4 | 74.3 | 77.2 |
| Fg115 25 µg/mL | 66.4 | 66.9 | 164 | 165 |
| Fg115 50 µg/mL | 67.5 | 70.9 | 173 | 200 |
| FliC-6his | 67.7 | 77.1 | 70.8 | 79.2 |
| gp120-6his | 68.2 | 82.3 | 118 | 126 |
| FliC-6his/ gp120-6his | 85 | 83.9 | 132 | 154 |

Example 13

Activation of TLR5 Receptor

HEK-Blue™ mTLR5 cell line (Invitrogen) was used to confirm that Fg115 activated TLR5. HEK-Blue™ mTLR5 cells are HEK293 cells that stably express the SEAP (secreted embryonic alkaline phosphatase) reporter gene under the control of the IL-12 p40 minimal promoter fused to five NF-κB and AP-1-binding sites. Stimulation with a TLR5 ligand activates NF-κB and AP-1, which induce the production of SEAP. TLR activation is visualised by a change in the colour of the HEK-Blue™ Detection media. TLR5 activation was confirmed for Fg115 engrafted liposomes, using different batches of Fg115 (data not shown). TLR5 activation was also observed with FliC-engrafted liposomes and a commercial preparation of flagellin (Biofarma), as well as liposomes co-engrafted with EAH (a recombinant protein that consists of the fusions of two TB antigens) and Fg115 or FliC. No TLR5 activation was observed with unengrafted liposomes, liposomes engrafted with EAH alone, or with PaM2CSK4 (a TLR2 agonist).

Example 14

Internalisation of Liposomes Engrafted with Different Batches of Fg115 and Using Different Liposome Backbones The consistency between different batches of Fg115 (batch May 2014 and batch July 2014), and using different liposome backbones, was assessed. Briefly, chelating liposomes were produced at 24 mM total lipid with 0.1% 3NTADTDA and the fluorescent tracer β-BODIPY 500/510 $C_{12}$-HPC (0.2%). The first lipid backbone was DOPC (67.2%), DOPG (30%) and DSPE-PEG750 (2.5%) (referred to as "DOPC/DOPG"), and the second lipid backbone was DOPC (97.4%) and DSPE-PEG750 (2.5%) (referred to as "DOPC"). In addition, DOPC/DOPG liposomes were prepared that carried an internal fluorescent peptide cargo (NT-FITC) rather than the lipid bilayer tracer β-BODIPY 500/510 $C_{12}$-HPC (percentage of DOPC in these liposomes was increased by 0.2% compared to the BODIPY liposomes). Liposomes were engrafted with the Fg115 protein in a total volume of 50 µL to produce the preparations set forth in Table 14 (5 mM total lipid).

Liposomes were added to moDCs maintained at 37° C. (20 µL of liposomes mixed with 50,000 cells) and the mixtures were incubated at the relevant temperature protected from light for 20 minutes. Cell-liposome mixtures were then washed either with PBS or PBS/imidazole and analysed by FACS. As shown in Table 14, improved internalisation by Fg115-engraftment was observed with both liposome types, with an approximately 5-fold increase in internalisation with both types of liposome backbones engrafted with Fg115 compared to unengrafted liposomes. Furthermore, the different batches of Fg115 provided comparable enhancement of internalisation.

TABLE 14

| Liposomes | Amount of engrafted Fg115 (µg/mL) | Internalisation (MFI) |
|---|---|---|
| Unengrafted DOPC/DOPG | 0 | 20.4 |
| DOPC/DOPG/Fg115 #05/2014 | 25 | 118 |
| DOPC/DOPG/Fg115 #07/2014 | 25 | 109 |
| Unengrafted DOPC | 0 | 11 |
| DOPC Fg115 #05/2014 | 25 | 52.6 |
| DOPC Fg115 #07/2014 | 25 | 53.9 |
| Unengrafted DOPC/DOPG NT-FITC | 0 | 8 |
| DOPC/DOPG NT-FITC/Fg115 #05/2014 | 25 | 25.8 |
| DOPC/DOPG NT-FITC/Fg115 #07/2014 | 25 | 23.8 |

Example 15

Internalisation of Fg115-engrafted DOPC/DOPG and POPC/DOPE Liposomes by Human moDCs Cells A study was performed to test the internalisation of NT-FITC liposomes prepared with two different liposome backbones, DOPC/DOPG and POPC/DOPG, each containing either 0.05% or 0.25% 3NTADTDA, 30% DOPG and the remaining percentage DOPC or POPC. Briefly, the chelating liposomes were produced at 48 mM total lipid with 0.05% or 0.25% 3NTADTDA and the internal fluorescent peptide NT-FITC (NT-FITC encapsulation was conducted at 1 mg/mL). Liposomes were engrafted with the Fg115 protein in a total volume of 100 µL to produce the liposome preparations described in Table 15, having a final total lipid content of 5 mM.

Liposomes were added to moDCs maintained at 37° C. (20 µL of liposomes mixed with 50,000 cells) and the mixtures were incubated protected from light for 60 minutes. Cell-liposome mixtures were then washed either with PBS or PBS/imidazole and analysed by FACS. The MFI values show in Table 15 show that enhancement of liposome internalization by Fg115-engraftment was more pronounced with liposomes prepared with a DOPC/DOPG backbone than a POPC/DOPG backbone, suggesting that liposome composition can affect internalisation. The results shown in Table 15 also demonstrate that engrafting Fg115 on liposomes with a lower 3NTADTDA content of 0.05% reduced enhancement of internalisation compared to that observed for Fg115-engrafted liposomes with 0.25% 3NTADTDA. Accordingly, both liposome backbone and 3NTADTDA content can affect the degree of enhancement of liposome internalization into moDCs.

TABLE 15

| Liposomes | Amount of engrafted Fg115 (µg/mL) | Internalisation (MFI) Donor 1 | Internalisation (MFI) Donor 2 |
|---|---|---|---|
| DOPC/PG-NT/FITC 0.05% 3 NTA | | | |
| Unengrafted | 0 | 10 | 8.9 |
| Fg115 | 80 | 63.1 | 33.3 |
| Fg115 | 25 | 53.5 | 25.6 |
| DOPC/PG-NT/FITC 0.25% 3 NTA | | | |
| Unengrafted | 0 | 11 | 10.2 |
| Fg115 | 80 | 141 | 70 |
| Fg115 | 25 | 86.4 | 42.2 |
| POPC/DOPG-NT/FITC 0.05% 3 NTA | | | |
| Unengrafted | 0 | 9.2 | 8.6 |
| Fg115 | 80 | 38 | 20.6 |
| Fg115 | 25 | 31.3 | 15.1 |
| POPC/DOPG-NT/FITC 0.25% 3 NTA | | | |
| Unengrafted | 0 | 9.1 | 9.1 |
| Fg115 | 80 | 50.2 | 27.2 |
| Fg115 | 25 | 34.9 | 36.6 |

Example 16

Internalisation of Fg115-engrafted DOPC/DOPG and POPC/DOPE Liposomes by Human moDCs Cells Another study was performed to test the internalisation of NT-FITC liposomes prepared with different liposome backbones: DOPC/DOPG ("DOPC/PG"); POPC/DOPG ("POPC/PG"); POPC; DOPC; DOPC/DOPE; DOPC/DOTAP; DOPC/DOPS; and DOPC/MPLA. Briefly, the chelating liposomes were produced at 48 mM total lipid with 0.25% 3NTADTDA and the internal fluorescent peptide NT-FITC (NT-FITC encapsulation was conducted at 1 mg/mL). Liposomes were engrafted with 25 or 80 µg/mL Fg115 protein to produce the liposome preparations described in Table 16.

TABLE 16

| Engraftment Number | Engraftment Details | Fg115 (July 2014) | Liposomes | PBS | Total Volume | [targeting molecule] mg/mL | Final total lipid (mM) |
|---|---|---|---|---|---|---|---|
| NT-FITC 6 DOPC/PG 0.25% | | | | | | | |
| 1 | Unengrafted | | 20.83 | 79.2 | 100 | 0 | 5 |
| 2 | FG 115 | 6.90 | 20.83 | 72.3 | 100 | 80 | 5 |
| 3 | FG 115 | 2.16 | 20.83 | 77.0 | 100 | 25 | 5 |
| NT-FITC 9 POPC/PG 0.25% | | | | | | | |
| 4 | Unengrafted | | 10.42 | 89.6 | 100 | 0 | 5 |
| 5 | FG 115 | 6.90 | 10.42 | 82.7 | 100 | 80 | 5 |
| 6 | FG 115 | 2.16 | 10.42 | 87.4 | 100 | 25 | 5 |
| NT-FITC 10 POPC 0.25% | | | | | | | |
| 7 | Unengrafted | | 10.42 | 89.6 | 100 | 0 | 5 |
| 8 | FG 115 | 6.90 | 10.42 | 82.7 | 100 | 80 | 5 |
| 9 | FG 115 | 2.16 | 10.42 | 87.4 | 100 | 25 | 5 |
| NT-FITC 11 DOPC 0.25% | | | | | | | |
| 10 | Unengrafted | | 10.42 | 89.6 | 100 | 0 | 5 |
| 11 | FG 115 | 6.90 | 10.42 | 82.7 | 100 | 80 | 5 |
| 12 | FG 115 | 2.16 | 10.42 | 87.4 | 100 | 25 | 5 |
| NT-FITC 12 DOPC/DOPE 0.25% | | | | | | | |
| 13 | Unengrafted | | 10.42 | 89.6 | 100 | 0 | 5 |
| 14 | FG 115 | 6.90 | 10.42 | 82.7 | 100 | 80 | 5 |
| 15 | FG 115 | 2.16 | 10.42 | 87.4 | 100 | 25 | 5 |
| NT-FITC 13 DOPC/DOTAP 0.25% | | | | | | | |
| 16 | Unengrafted | | 10.42 | 89.6 | 100 | 0 | 5 |
| 17 | FG 115 | 6.90 | 10.42 | 82.7 | 100 | 80 | 5 |
| 18 | FG 115 | 2.16 | 10.42 | 87.4 | 100 | 25 | 5 |
| NT-FITC 14 DOPC/DOPS 0.25% | | | | | | | |
| 19 | Unengrafted | | 10.42 | 89.6 | 100 | 0 | 5 |
| 20 | FG 115 | 6.90 | 10.42 | 82.7 | 100 | 80 | 5 |
| 21 | FG 115 | 2.16 | 10.42 | 87.4 | 100 | 25 | 5 |
| NT-FITC 15 DOPC/MPLA 0.25% | | | | | | | |
| 22 | Unengrafted | | 10.42 | 89.6 | 100 | 0 | 5 |
| 23 | Fg115 | 6.90 | 10.42 | 82.7 | 100 | 80 | 5 |
| 24 | Fg115 | 2.16 | 10.42 | 87.4 | 100 | 25 | 5 |

Liposomes were added to moDCs from one of two donors (donor 1 or 2) maintained at 37° C. (20 μL of liposomes mixed with 50,000 cells) and the mixtures were incubated protected from light for 60 minutes. Cell-liposome mixtures were then washed either with PBS or PBS/imidazole and analysed by FACS. Consistent with the results described above, Fg115-engraftment enhanced liposome internalization (data not shown). The results of this study also demonstrated that enhancement of liposome internalization by Fg115-engraftment tended to be more pronounced with liposomes prepared with DOPC.

Example 17

Inhibition of Fg115-engrafted Liposome Binding by Mannan

Liposome formulations were prepared to test the effect of the yeast derived polysaccharide mannan (Sigma Aldrich) on the binding of Fg115-engrafted liposomes to human moDCs cells in vitro. Briefly, chelating liposomes were produced at 24 mM total lipid with 0.25% 3NTADTDA and the fluorescent tracer β-BODIPY 500/510 $C_{12}$-HPC (0.2%). The lipid backbone was DOPC (67.05%), DOPG (30%) and DSPE-PEG750 (2.5%). Liposomes were engrafted with Fg115 or DMS5000 at a final concentration of 25 μg/mL and at final lipid content of 5 mM. Unengrafted liposomes were also prepared. moDCs were pre-incubated with mannan at 10 mg/mL before the addition of liposomes (20 μL of liposomes mixed with 50,000 cells), and the mixtures were incubated at 4° C. protected from light for 60 minutes. Binding of liposomes to moDCs was then analysed by FACs, and MFI values were quantitated. The inhibition of Fg115-engrafted liposome binding to moDCs by mannan (a reduction in MFI from 52.4 in untreated cells to 18 in mannan-treated cells) suggests that Fg115-engrafted liposomes bind to moDCs through the sugars on the polypeptide backbone. A similar inhibition of binding was observed using DMS5000-engrafted liposomes (a reduction in MFI from 787 in untreated cells to 517 in mannan-treated cells) but not unengrafted liposomes (a reduction in MFI from 19.8 in untreated cells to 17.7 in mannan-treated cells).

Example 18

Inhibition of the Internalization of Fg115-engrafted Liposomes with Varying Amounts of 3NTADTDA by Mannan The effect of varying amounts of 3NTADTDA on the inhibition of internalisation by mannan was assessed. Briefly, chelating liposomes were produced at 24 mM total lipid with a DOPC/DOPG/DSPE-PEG750 backbone and 0.05% or 0.25% 3NTADTDA (i.e. 2.5% DSPE-PEG750, 30% DOPG, and either 67.05% or 67.25% DOPC or POPC). The liposomes were prepared with the internal fluorescent peptide NT-FITC, with encapsulation conducted at 2 mg/mL. Liposomes were engrafted with Fg115 to produce the preparations shown in Table 17 (final volume of 100 μL and final total lipid content of 5 mM).

moDCs were pre-incubated with mannan at 10 mg/mL before the addition of engrafted liposomes (20 μL of engrafted liposomes mixed with 50,000 cells) and the mixtures were incubated at 4° C. protected from light for 60 minutes. Cell-liposome mixtures were then washed either with PBS or PBS/imidazole and analysed by FACS. MFI values were quantitated and the results shown in Table 17. Internalisation of Fg115-engrafted liposomes with 0.05% 3NTADTDA was inhibited by mannan to a greater extent than that observed with Fg115-engrafted liposomes with 0.25% 3NTADTDA, providing further proof that Fg115-engrafted liposomes bind to moDCs through the sugars on the polypeptide backbone.

TABLE 17

| Liposomes | Engrafted Fg115 (g/mL) | Internalisation (MFI) | |
|---|---|---|---|
| | | Untreated cells | Mannan-treated cells |
| DOPC/PG-NT/FITC 0.05% 3 NTA | | | |
| Unengrafted | 0 | 8.3 | 8.1 |
| Fg115 | 80 | 23.1 | 9.4 |
| Fg115 | 25 | 16.7 | 8.5 |
| DOPC/PG-NT/FITC 0.25% 3 NTA | | | |
| Unengrafted | 0 | 8.8 | 8.4 |
| Fg115 | 80 | 62.3 | 9.6 |
| Fg115 | 25 | 34.3 | 8.5 |

Example 19

Cross-presentation of the SIINFEKL Peptide by MHC Class I Complex Using Fg115-engrafted Liposomes in DC-SIGN Transgenic Mice Cross-presentation of encapsulated SIINFEKL peptide was assessed using Fg115-engrafted liposomes. Briefly, chelating liposomes were produced at 24 mM total lipid with backbones consisting of DOPC/DOPG/DSPE-PEG750 (67.25% DOPC, 30% DOPG and 2.5% DSPE-PEG750). 3NTADTDA was included at 0.25%. Liposomes were prepared that carried either 'high' or 'low' SIINFEKL cargo. 'high' SIINFEKL liposomes were prepared by rehydrating the liposomes (24 mM) with 0.5 mg/mL SIINFEKL and 'low' SIINFEKL liposomes were prepared by rehydrating the same lipid with SIINFEKL at 0.050 mg/mL. All liposomes were extruded through 0.2 μm membrane and unencapsulated SIINFEKL was removed by dialysis (300 kDa MWCO). This resulted in liposomes with approximately 4× difference in SIINFEKL content (Table 18). These liposomes were then engrafted with Fg115 in a total volume of 50 μL to produce the liposome preparations set forth in Table 19, having a final lipid content of 5 mM.

TABLE 18

| Liposomes | Lipid composition | Encapsulation | SIINFEKL μg/mL | Lipid mM |
|---|---|---|---|---|
| SIINFEKL Low | 0.25% 3NTADTDA/ DOPC/DOPG/DSPE-PEG750 | 2 mL of 24 mM lipid film rehydrated 50 μg/mL SIINFEKL saline | 27.05 | 23.69 |
| SIINFEKL High | 0.25% 3NTADTDA/ DOPC/DOPG/DSPE-PEG750 | 2 mL of 24 mM lipid film rehydrated 500 μg/mL SIINFEKL saline | 129.7 | 29.71 |

CD11c+ cells were prepared from mouse C57/B16 DC-SIGN transgenic mice (top panel) or wild type C57B1/6 mice (bottom panel) using anti-CD11c Microbeads via magnetic MACS separation (Miltenybiotec). Cells were either pulsed (20 minutes) or co-cultured (16 hours) with SIINFEKL liposomes listed in Table 19. SIINFEKL presentation was assessed by staining with mAb 25-D1.16 (eBioscience), which reacts with the ovalbumin-derived peptide SIINFEKL bound to H-2Kb of MHC class I, but not with unbound H-2Kb, or H-2Kb bound with an irrelevant peptide. Cells were then analysed by FACS. The effect of liposome backbone and Fg115-engraftment on SIINFEKL cross presentation was assessed by comparing the MFI values (Table 19). Liposomes engrafted with Fg115 were able to improve cross-presentation of the SIINFEKL peptide. Improved cross presentation was observed with wild-type and DC-SIGN transgenic cells when liposomes were engrafted with Fg115 content of 80 μg/mL.

TABLE 19

| Liposomes | Fg115 μg/mL | SIINFEKL μg/mL | SIINFEKL presentation by DC-SIGN transgenic CD11+ cells (MFI) | | SIINFEKL presentation by wild type C57Bl/6 CD11+ cells (MFI) | |
|---|---|---|---|---|---|---|
| | | | Pulsed | Co-cult. | Pulsed | Co-cult. |
| SIINFEKL (low) unengrafted | 0 | 5.71 | 15.8 | 153 | 25.1 | 199 |
| SIINFEKL (high) unengrafted | 0 | 21.83 | 25.5 | 524 | 27.8 | 643 |
| SIINFEKL (low) Fg115 | 80 | 5.71 | 21.7 | 247 | 33.2 | 289 |
| SIINFEKL (high) Fg115 | 80 | 21.83 | 51.9 | 703 | 61.3 | 754 |

Example 20

Effect of Liposome Backbone on SIINFEKL Cross Presentation Using Fg115-engrafted Liposomes in Wild-type Mice Cross-presentation of encapsulated SIINFEKL peptide was assessed using Fg115-engrafted liposomes with different liposome backbones. Briefly, chelating liposomes were produced at 24 mM total lipid with encapsulated SIINFEKL peptide with the liposome backbones shown in Table 18. 3NTADTDA was included at 0.05%. Liposomes were prepared with 'high' SIINFEKL cargo by rehydrating the liposomes (24 mM) with 0.5 mg/mL SIINFEKL. All liposomes were extruded through 0.2 μm membrane and unencapsulated SIINFEKL was removed by dialysis (300 kDa MWCO). This resulted in liposomes with an approximately 4-fold difference in SIINFEKL content (Table 20). Liposomes were engrafted with 25 μg/mL Fg115 or 20 μg/mL FliC in 100 μL to produce the liposome preparations for testing shown in Table 21 (each having a final, total lipid content of 5 mM).

TABLE 20

| Liposomes | Lipid composition | Encapsulation | SIINFEKL μg/mL | Lipid mM |
|---|---|---|---|---|
| SIINFEKL DOPC | 0.05% 3NTADTDA/DOPC/DSPE-PEG750 | 1 mL of 24 mM lipid film rehydrated 500 μg/mL SIINFEKL saline | 51.12 | 26.94 |
| SIINFEKL DOPC/DOPG | 0.05% 3NTADTDA/DOPC/DOPG/DSPE-PEG750 | 1 mL of 24 mM lipid film rehydrated 500 μg/mL SIINFEKL saline | 152.76 | 26.77 |
| SIINFEKL DOPC/DOPE | 0.05% 3NTADTDA/DOPC/DOPE/DSPE-PEG750 | 1 mL of 24 mM lipid film rehydrated 500 μg/mL SIINFEKL saline | 45.74 | 25.56 |
| SIINFEKL POPC/DOPG | 0.05% 3NTADTDA/POPC DOPG/DSPE-PEG750 | 1 mL of 24 mM lipid film rehydrated 500 μg/mL SIINFEKL saline | 124.84 | 26.52 |

CD11c+ cells were prepared from mouse C57/B16 wild type mice using anti-CD11c Microbeads via magnetic MACS separation (Miltenybiotec). Cells were then pulsed for 20 minutes with the liposomes, and SIINFEKL presentation was assessed by staining with mAb 25-D1.16 and analysis by FACS. The effect of liposome backbone and Fg115-engraftment on SIINFEKL cross presentation was assessed by comparing the MFI values (Table 21). The improved cross presentation observed with wild-type and DC-SIGN transgenic cells when liposomes were engrafted with Fg115 content of 80 µg/mL in Example 19, above, was not generally observed in wild type cells when liposomes were engrafted with the lower dose of 25 µg/mL.

TABLE 21

| Liposomes | Fg115 µg/mL | SIINFEKL µg/mL | SIINFEKL presentation by wild type C57Bl/6 CD11+ cells (MFI) |
|---|---|---|---|
| DOPC-unengrafted | 0 | 9.49 | 32.3 |
| DOPC-Fg115 | 25 | 9.49 | 29.7 |
| DOPC-FliC | 20 | 9.49 | 24.8 |
| DOPC/DOPG- unengrafted | 0 | 28.53 | 36.1 |
| DOPC/DOPG-Fg115 | 25 | 28.53 | 35 |
| DOPC/DOPG-FliC | 20 | 28.53 | 30.9 |
| DOPC/DOPE- unengrafted | 0 | 8.95 | 16.1 |
| DOPC/DOPE-Fg115 | 25 | 8.95 | 16.3 |
| DOPC/DOPE-FliC | 20 | 8.95 | 14.2 |
| POPC/DOPG- unengrafted | 0 | 23.54 | 22.3 |
| POPC/DOPG-Fg115 | 25 | 23.54 | 42.4 |
| POPC/DOPG-FliC | 20 | 23.54 | 31.9 |

Example 21

Ability of Fg115-engrafted Liposomes to Induce CB8+ T Cell Responses in Vitro

The ability of Fg115-engrafted liposomes to induce CD8+ T cell responses in vitro was assessed using ovalbumin-loaded liposomes. Briefly, chelating liposomes with encapsulated ovalbumin (OVA) were produced at 24 mM total lipid with a 67.25% DOPC, 30% DOPG and 2.5% DSPE-PEG750 backbone with 0.25% 3NTADTDA. The OVA-loaded liposomes (LipOVA) were prepared by rehydrating the liposomes with 1.5 mg/mL OVA, and the liposomes were then extruded through a 0.2 µm membrane and dialysed (300kDa MWCO). The resulting LipOVA formulations contained 29.7 mM lipid and 476 µg/mL OVA. When the LipOVA formulations were diluted to 215 µg/mL OVA, the OVA:lipid ratio was 19.85 µg OVA per mg lipid. This diluted LipOVA formulation was then used for engraftment with 100 µg/mL Fg115 to produce LipOVA-Fg115 liposomes with a total lipid content of 13 mM, or with 74 µg/mL control molecule (his-tagged control domain antibody; Domantis Ltd) to produce LipOVA-cont liposomes with a total lipid content of 13 mM.

CD11c+ cells were prepared from mouse C57/B16 DC-SIGN transgenic mice using anti-CD11c Microbeads via magnetic MACS separation (Miltenybiotec). CD11c+ cells, at a density of 1.2×10⁶ cells /ml and in replicates of 5, were then cultured with liposome formulations in wells of a u-bottomed 96 well plate for 18 hrs at 37° C. (10 µg/mL OVA final for each well). Cells were then harvested and used to stimulate OVA-specific CD8+ T cells (OT-I cells), which were purified by negative selection from OT-I TCR-transgenic mice via magnetic MAC separation (Miltenybiotec) using anti-B220/anti-TER119 antibodies attached to Microbeads (Miltenybiotec). OT-I T cells were cultured with CD11c+ dendritic cells at a ratio of ~5-20:1 in wells of a u-bottomed 96 well plate for 18 hrs at 37° C. Liposome immunogenicity was then assessed by determining CD8+ T cell activation through CD69 and CD44 upregulation using antibodies and flow cytometry, i.e. with CD69hiCD44hi CD8 T cell populations used as a indicator of T cell activation. Controls of T cells alone, or T cells incubated with saline or OVA were also included in the study. Engraftment of Fg115 on the surface of DOPC/DOPG liposomes improved activation of CD8+ T cells almost 3-fold compared to liposomes engrafted with a control molecule (data not shown).

Example 22

Capacity of Fg115-engrafted and Fg115-admixed Liposomes to Induce CD8+ T Cell Responses The ability of Fg115-engrafted liposomes to induce CD8+ T cell responses was confirmed in an additional study. Briefly, chelating liposomes were produced at 24 mM total lipid with a backbone of 67.25% DOPC, 30% DOPG and 2.5% DPSE-PEG750 and 0.25% 3NTADTDA, and rehydrated with 1.5 mg/mL OVA. The LipOVA liposomes were then engrafted with 100 µg/mL Fg115, for final lipid content of at 7.48 mM and 215 µg/mL OVA, or left unengrafted.

CD11c+ cells were prepared from mouse C57/B16 DC-SIGN transgenic mice using anti-CD11c Microbeads via magnetic MACS separation (Miltenybiotec). CD11c+ cells, at a density of 1.2×10⁶ cells /ml and in replicates of 5, were then cultured with liposome formulations in wells of a u-bottomed 96 well plate for 18 hrs at 37° C. Cells were then harvested and used to stimulate OVA-specific CD8+ T cells (OT-I cells), which were purified by negative selection from OT-I TCR-transgenic mice via magnetic MAC separation (Miltenybiotec) using anti-B220/anti-TER119 antibodies attached to Microbeads (Miltenybiotec). OT-I T cells were cultured with CD11c+ dendritic cells at a ratio of ~5-20:1 in wells of a u-bottomed 96 well plate for 18 hrs at 37° C. Liposome immunogenicity was then assessed by determining CD8+ T cell activation through CD69 and CD44 upregulation using antibodies and flowcytometry, i.e. with CD69hiCD44hi CD8 T cell populations used as a indicator of T cell activation. Controls of T cells alone, or T cells cultured with CD11c+ cells and saline, Fg115, OVA, or OVA +Fg115 were also included in the study. Fg115-engraftment of liposomes improved activation of CD8+ T cells compared to unengrafted liposomes (approximately 55% activated OT-I CD8 T cells using Fg115-engrafted liposomes compared to approximately 35% using unengrafted liposomes) and compared to soluble OVA+Fg115 (approximately 30% activated OT-I CD8 T cells). As expected, negligible CD8+ T cell activation was observed with the negative controls.

Example 23

Capacity of Fg115-engrafted and Fg115-admixed Liposomes to Induce CD8+ T Cell Responses The ability of liposomes engrafted with high and low concentration of Fg115, or admixed with Fg115, to induce CD8+ T cell responses was assessed. Briefly, chelating liposomes were produced at 24 mM total lipid with a backbone of 67.25% DOPC, 30% DOPG and 2.5% DPSE-PEG750 and 0.25% 3NTADTDA, and rehydrated with 1.5 mg/mL OVA. The LipOVA liposomes were then engrafted with 5 or 50 µg/mL Fg115, for final lipid content of at 10 mM and 215 µg/mL OVA, or left unengrafted. LipOVA liposomes admixed with Fg115 were also prepared by mixing LipOVA liposomes with Fg115 in the absence of NiSO$_4$.

CD11c$^+$ cells were prepared from mouse C57/B16 DC-SIGN transgenic mice using anti-CD11c Microbeads via magnetic MACS separation (Miltenybiotec). CD11c$^+$ cells, at a density of 1.2×10$^6$ cells /ml and in replicates of 5, were then cultured with liposome formulations in wells of a u-bottomed 96 well plate for 18 hrs at 37° C. (10 µg/mL OVA final for each well). Cells were then harvested and used to stimulate OVA-specific CD8$^+$ T cells (OT-I cells), which were purified by negative selection from OT-I TCR-transgenic mice via magnetic MAC separation (Miltenybiotec) using anti-B220/anti-TER119 antibodies attached to Microbeads (Miltenybiotec). OT-I T cells were cultured with CD11c$^+$ dendritic cells at a ratio of ~5-20:1 in wells of a u-bottomed 96 well plate for 18 hrs at 37° C. Liposome immunogenicity was then assessed by measuring CD69hiCD44hi CD8 T cell populations as a indicator of T cell activation. Controls of T cells alone, or T cells cultured with CD11c$^-$ cells and saline, Fg115, OVA, or OVA+Fg115 were also included in the study.

Fg115-engraftment of liposomes improved activation of CD8$^+$ T cells compared to unengrafted liposomes and compared to soluble OVA+Fg115, consistent with the results from Example 22. It was also observed that admixing Fg115 with liposomes improved CD8$^+$ T cell activation compared to soluble OVA+Fg115 or unengrafted liposomes (data not shown).

Example 24

Effect of Encapsulated OVA Levels on the Ability of Fg115-engrafted Liposomes to Induce CD8$^+$ T Cell Responses The effect of encapsulated OVA levels on the ability of Fg115-engrafted liposomes to induce CD8$^+$ T cell responses was assessed. Briefly, chelating liposomes with high levels of OVA (LipOVA(high): 436 µg/mL OVA) or low high levels of OVA (LipOVA(low): 129 µg/mL OVA) were produced (Tables 22 and 23). Liposomes were then engrafted with Fg115, gp120 or FliC, or left unengrafted, at 13 mM total lipid to produce the lipid formulations in Table 24.

TABLE 22

LipOVA(high) 13.6 µg/mL OVA per mM lipid

| Formulation | 0.25% 3NTADTDA, 67.25% POPC, 30% DOPG, 2.5% DSPE-PEG750 |
| --- | --- |
| Encapsulation/rehydration of lipid film | 1.5 mg/mL in saline (no Nickel) |
| extrusion | 5x 0.2 µm |
| [OVA] | 436 µg/mL |
| [Lipid] | 32.17 mM |

TABLE 23

LipOVA(low) 4.8 µg/mL OVA per mM lipid

| Formulation | 0.25% 3NTADTDA, 67.25% POPC, 30% DOPG, 2.5% DSPE-PEG750 |
| --- | --- |
| Encapsulation/rehydration of lipid film | 0.375 mg/mL in saline (no Nickel) |
| extrusion | 5x 0.2 µm |
| [OVA] | 129 µg/mL |
| [Lipid] | 26.77 mM |

TABLE 24

| Liposome | Final volume (µL) | mM Lipid | OVA µg/mL | Fg115 µg/mL | FliC µg/mL | gp120 µg/mL |
| --- | --- | --- | --- | --- | --- | --- |
| LipOVA(high)-Fg115 | 150 | 7.38 | 100 | 36.89 | 0 | 0 |
| LipOVA(high)-unengrafted | 150 | 7.38 | 100 | 0 | 0 | 0 |
| LipOVA (high)-gp120 | 75 | 7.38 | 100 | 0 | 0 | 20.24 |
| LipOVA(high)-FliC | 150 | 7.38 | 100 | 0 | 17.00 | 0 |
| LipOVA(high)-FliC (treated)-gp120 | 75 | 7.38 | 100 | 0 | 17.00 | 20.24 |
| LipOVA (low)-unengrafted | 75 | 20.75 | 100 | 0.00 | 0 | 0 |
| LipOVA (low)-Fg115 | 100 | 20.75 | 100 | 103.76 | 0 | 0 |
| LipOVA(low)-Fg115(low) | 75 | 20.75 | 100 | 36.89 | 0 | 0 |

Figure 4:
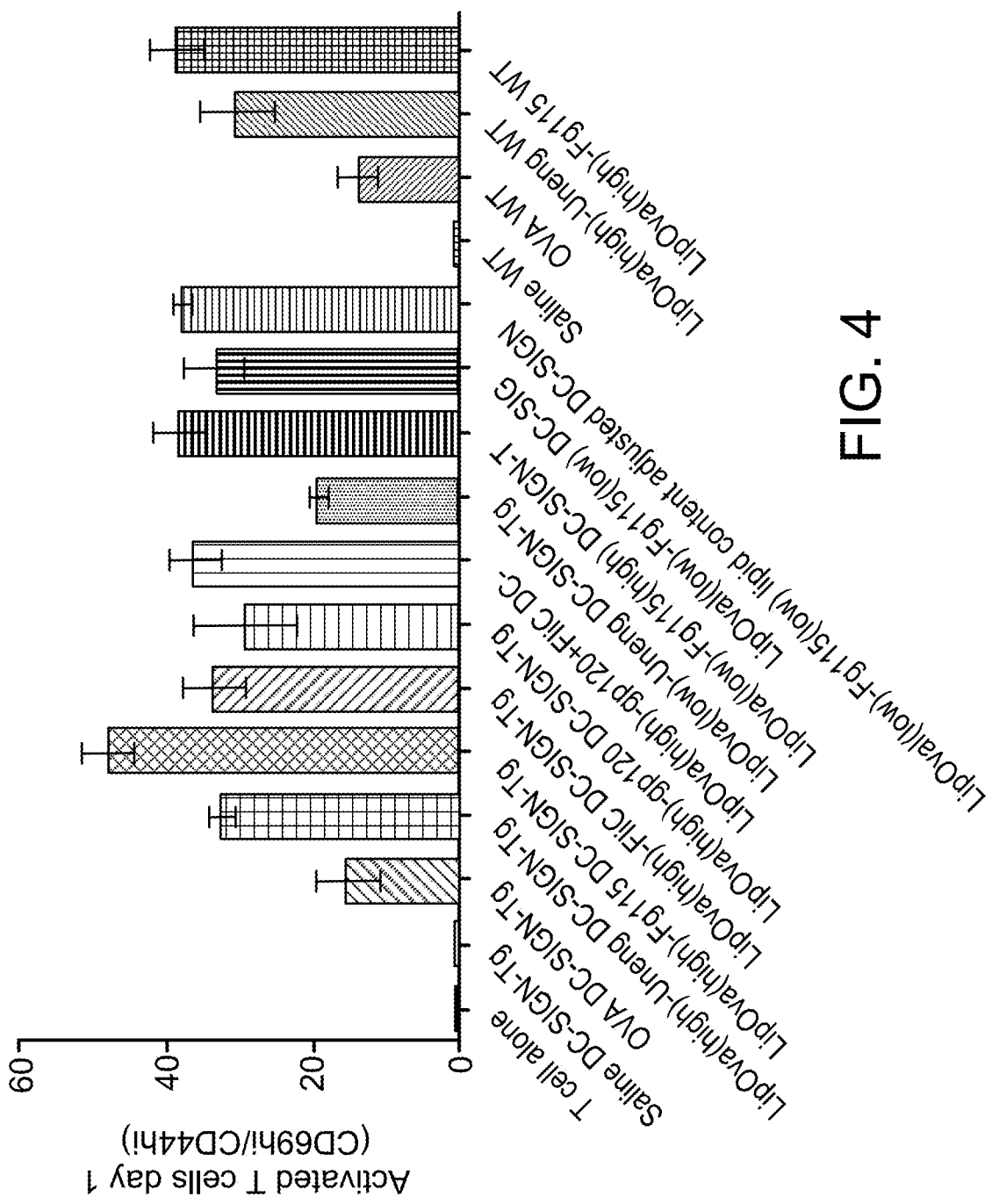
FIG. 4 shows the results of FACs analysis of OT-I cells incubated with CD11c$^+$ cells from DC-SIGN transgenic mice (DC-SIGN Tg) that had been cultured with liposomes loaded with high levels of OVA (LipOVA(high): 100 μg/mL per 7.38 mM lipid final concentration) or low levels of OVA (LipOVA(low): 100 μg/mL per 20.75 mM lipid final concentration) and engrafted with Fgl15, FliC or gp120. Unengrafted liposomes (Uneng) were also used in the study. Fgl15 was engrafted at 104 μg/mL at 20.75 mM lipid or 37 μg/mL at 20.75 mM (Fgl15(low)). Controls using OT-I cells cultured with CD11c$^+$ cells from DC-SIGN transgenic mice and saline or OVA, or dendritic cells from wild-type mice (WT) and saline or OVA or FACs analysis of T cells alone, were also included. The percentage of activated, CD69hiCD44hi CD8 T cells is shown.

CD11c$^+$ cells were prepared from mouse C57/B16 DC-SIGN transgenic mice using anti-CD11 c Microbeads via magnetic MACS separation (Miltenybiotec). CD11c$^+$ cells, at a density of 1.2×10$^6$ cells /ml and in replicates of 5, were then cultured with liposome formulations in wells of a u-bottomed 96 well plate for 18 hrs at 37° C. (10 µg/mL OVA final for each well). Cells were then harvested and used to stimulate OVA-specific CD8$^+$ T cells (OT-I cells), which were purified by negative selection from OT-I TCR-transgenic mice via magnetic MAC separation (Miltenybiotec) using anti-B220/anti-TER119 antibodies attached to Microbeads (Miltenybiotec). OT-I T cells were cultured with CD11c$^+$ dendritic cells at a ratio of ~5-20:1 in wells of a u-bottomed 96 well plate for 18 hrs at 37° C. Liposome immunogenicity was then assessed by measuring CD69hiCD44hi CD8 T cell populations as a indicator of T cell activation. Controls of T cells alone, T cells cultured with CD11c$^-$ cells and saline or OVA, or T cells cultured with wild-type dendritic cells and saline or OVA were also included in the study. As shown in FIG. 4, the levels of encapsulated OVA affected the ability of the liposomes to induce CD8 activation, with LipOVA(high) liposomes inducing higher levels of CD8$^+$ T cell activation.

Example 25

Effect of Different Liposome Backgrounds on Fg115-engrafted Liposome CD8+ T Cell Activation OVA-loaded liposomes with various backbones were prepared to assess the effect of different liposome backgrounds on the anility of Fg115-engrafted liposomes to activate CD8+ T cells. Briefly, chelating liposomes having 0.25% 3NTADTDA and various liposome backbones were rehydrated with 1.5 mg/mL OVA to produce the OVA-loaded liposomes shown in Table 25. All liposomes were extruded through 0.2 µm membrane and unencapsulated OVA was removed by overnight dialysis (300 kDa MWCO). The LipOVA liposomes were engrafted with various concentrations of Fg115 and total lipid as shown in Table 26.

TABLE 25

| Liposome backbone | OVA start mg/mL | Lipid start mM | OVA final µg/mL |
|---|---|---|---|
| DOPC/DSPE-PEG750 | 0.6 | 24 | 108 |
| DOPC/DOPG/DSPE-PEG750 | 0.6 | 24 | 121 |
| DOPC/DOPS/DSPE-PEG750 | 0.6 | 24 | 67 |
| DOPC/DOPE/DSPE-PEG750 | 0.6 | 24 | 80 |
| DOPC/DOTAP/DSPE-PEG750 | 0.6 | 24 | 49 |
| POPC/DSPE-PEG750 | 0.6 | 24 | 98 |
| POPC/DOPG/DSPE-PEG750 | 0.6 | 24 | 63 |
| POPC/DOPE/DSPE-PEG750 | 0.6 | 24 | 49 |
| POPC/DOTAP/DSPE-PEG750 | 0.6 | 24 | 34 |
| DOPC/MPLA/DSPE-PEG750 | 0.6 | 24 | 58 |
| DOPC/LIPOKEL/DSPE-PEG750 | 0.6 | 24 | 50 |

DOPG, DOPE, DOTAP, DOPS, MPLA and LIPOKEL included at 30% total lipid. DSPE-PEG750 included at 2.5% total lipid.

TABLE 26

| Liposomes | Final volume (µL) | mM Lipid | OVA µg/mL | Fg115 µg/mL |
|---|---|---|---|---|
| Fg115-engrafted liposomes | | | | |
| DOPC/PEG/OVA liposomes | 100.0 | 10.0 | 45.0 | 25.0 |
| DOPC/DOPG/PEG/OVA liposomes | 100.0 | 8.9 | 45.0 | 22.3 |
| DOPC/DOPS/PEG/OVA liposomes | 100.0 | 16.2 | 45.0 | 40.5 |
| DOPC/DOPE/PEG/OVA liposomes | 100.0 | 13.5 | 45.0 | 33.9 |
| DOPC/DOTAP/PEG/OVA liposomes | 100.0 | 22.0 | 45.0 | 55.0 |
| POPC/PEG/OVA liposomes | 100.0 | 11.0 | 45.0 | 27.5 |
| POPC/DOPG/PEG/OVA liposomes | 100.0 | 17.2 | 45.0 | 43.1 |
| POPC/DOPE/PEG/OVA liposomes | 100.0 | 21.9 | 45.0 | 54.7 |
| POPC/DOTAP/PEG/OVA liposomes | 105.0 | 22.9 | 45.0 | 55.2 |
| DOPC/MPLA/PEG/OVA liposomes | 100.0 | 18.6 | 45.0 | 46.5 |
| DOPC/LIPOKEL/PEG/OVA liposomes | 100.0 | 21.5 | 45.0 | 53.8 |
| Negative controls | | | | |
| OVA | 100 | | 45 | |
| DOPC/PEG/OVA liposomes | 100.0 | 10.0 | 45.0 | 0.0 |
| DOPC/MPLA/PEG/OVA liposomes | 100.0 | 18.6 | 45.0 | 0.0 |
| DOPC/LIPOKEL/PEG/OVA liposomes | 100.0 | 21.5 | 45.0 | 0.0 |

Figure 5:
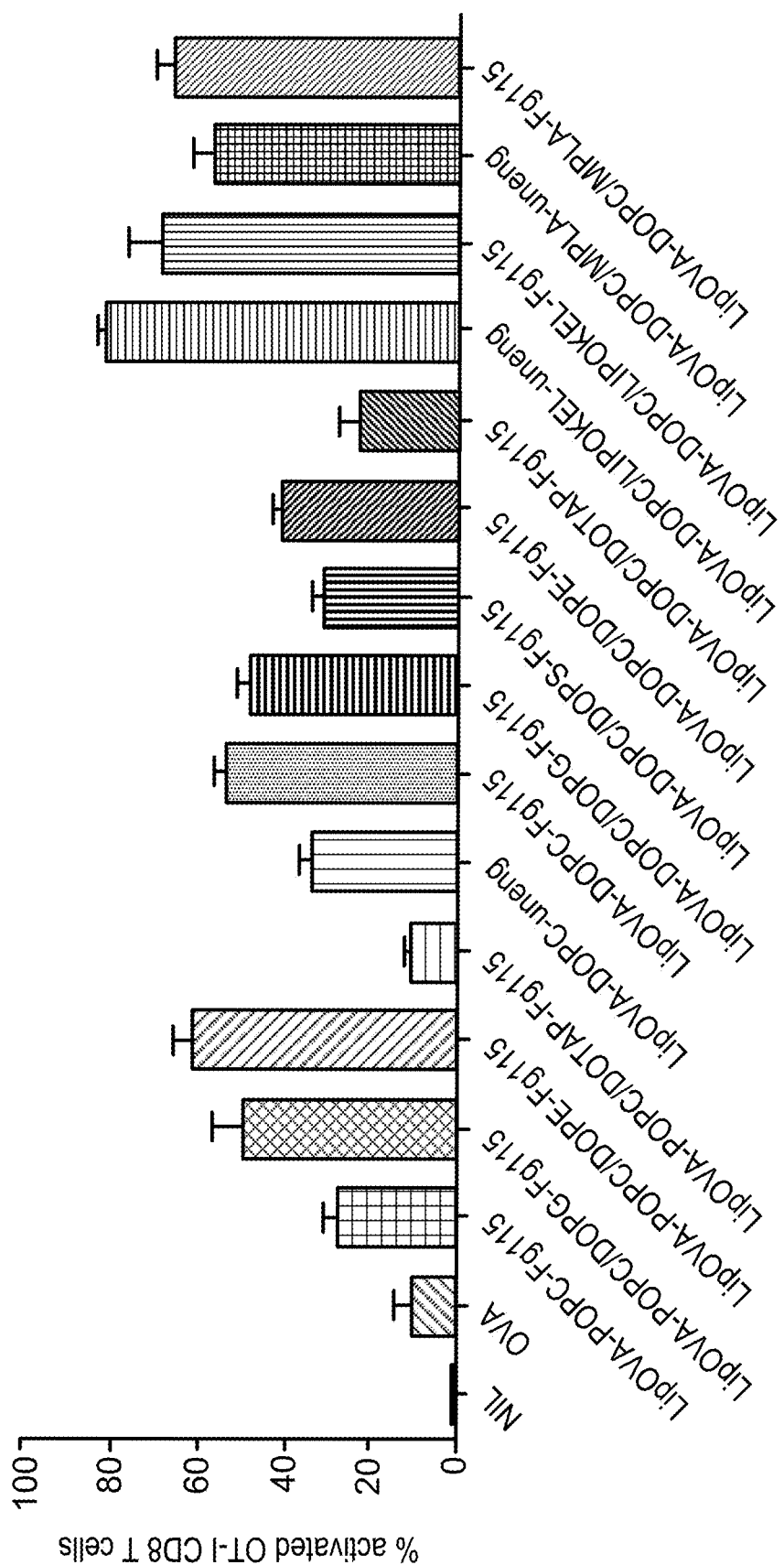
FIG. 5 shows the results of FACs analysis of OT-I cells incubated with CD11c$^+$ cells from C57BL/6J wild type mice that had been cultured with liposomes loaded with OVA (LipOVA) and engrafted with Fgl15. Liposomes with various backbones were used. Liposome backbones included DOPC ('LipOVA-DOPC'), DOPC/DPOP(30%) ('LipOVA-DOPC/DOPG'), DOPC/DOPS(30%) ('LipOVA-DOPC/DOPS'), DOPC/DOTAP(30%) ('LipOVA-DOPC/DOTAP'), POPC (LipOVA-POPC), POPC/DOPG(30%) ('LipOVA-POPC/DOPG'), POPC/DOPE(30%) ('LipOVA-POPC/DOPE'), POPC/DOTAP(30%) ('LipOVA-POPC/DOTAP), DOPC/MPLA ('LipOVA-DOPC/MPLA) and DOPC/LIPOKEL (LipOVA-DOPC/LIPOKEL). Unengrafted liposomes (Uneng) were also used in the study. Controls using OT-I cells cultured with CD11c+ cells and saline ("Nil") or OVA were also included. The percentage of activated, CD69hiCD44hi CD8 T cells is shown.

CD11c+ cells were prepared from mouse C57/B16 wild type mice. Cells were cultured with the liposomes overnight, and OT-I CD8 T cell activation by CD11c+ cells was assessed as described above. As shown in FIG. 5, liposome backbone composition affected the levels of CD8+ T cell activation, with the best activation observed with POPC/DOPE, POPC/DOPG and DOPC/DOPG backbones.

Example 26

Ability of Fg115-engrafted Liposomes to Induce CD8+ T Cell Responses in Vivo The ability of Fg115-engrafted liposomes to induce CD8+ T cell responses in vivo was assessed. Chelating liposomes were produced at 24 mM total lipid. Briefly, liposomes were prepared with OVA and backbones of 67.25% DOPC, 30%DOPG and 2.5% DPSE-PEG750 with 0.25% 3NTADTDA, as described above (Table 27). LipOVA liposomes were engrafted with 100 µg/mL Fg115 at 17.38 mM total lipid, with a final OVA concentration of 500 µg/mL. Mice were immunised with the LipOVA-Fg115 or unengrafted LipOVA liposome preparations in Table 28.

TABLE 27

| | LipOVA |
|---|---|
| Formulation | 0.25% 3NTADTDA/67.25% DOPC/30% DOPG/2.5% DPSE-PEG750 (24 mM) |
| Encapsulation/rehydration of lipid film | 1.5 mg/mL in saline (no Nickel) |
| extrusion | 5x 0.2 µm |
| [OVA] | 649 µg/mL |
| [Lipid] | 22.6 mM |

TABLE 28

| | Final volume (µL) | mM Lipid | OVA µg/mL | Fg115 µg/mL |
|---|---|---|---|---|
| LipOVA - unengrafted | 350 | 17.38 | 500 | 0 |
| LipOVA-Fg115 | 650 | 17.38 | 500 | 116.3 |

OVA-specific CD8$^+$ T cells were purified by negative selection from OT-I TCR-transgenic mice via magnetic MACS separation (Miltenybiotec) using anti-B220/anti-TER119 antibodies attached to Microbeads (Miltenybiotec). Cells were also labeled with the vital dye CFSE, to allow assessment of cell division by dye dilution. CD8$^-$ T cells (10$^6$ cells) were adoptively transferred into C57BL/6J host mice via intraveous injection into the lateral tail vein. After 24 hrs, host mice were then immunized in replicates of 5 mice per group with various liposome formulations in a 50 µl bolus of saline injected intarmuscularly. After 6 days, a fluorescent target array (FTA) was generated using splenocytes from CD45.1$^+$ C57BL/6J mice and comprised of target cells pulsed with different concentrations of several variant OVA MHC-I-binding peptides. 1-5×10$^6$ FTA cells were injected intravenously into host mice via the lateral tail vein. After 18 hr in host animals, FTA cells were assessed for death in spleen cells isolated from sacrificed host mice using antibody and Hoechst 33258 (to assess viability of cells) labeling and flowcytometry. % specific killing of FTA cells was assessed using the flowing formula, $$\% \text{ specific killing} = \left[ 1 - \left( \frac{\text{Targets}_{primed}^{+peptide} / \text{Targets}_{primed}^{+nil}}{\text{Targets}_{naive}^{+peptide} / \text{Targets}_{naive}^{+nil}} \right) \right] \times 100.$$

In addition, % IFN-γ CD8$^+$ T cells was assessed in spleen cells isolated from sacrificed host mice, after they were cultured for 6 hr in vitro with 10 µg/ml SIINFEKL peptide and Golgistop (BD bioscience), using intracellular cytokine staining (ICS) with antibody and flowcytometry.

Figure 6:
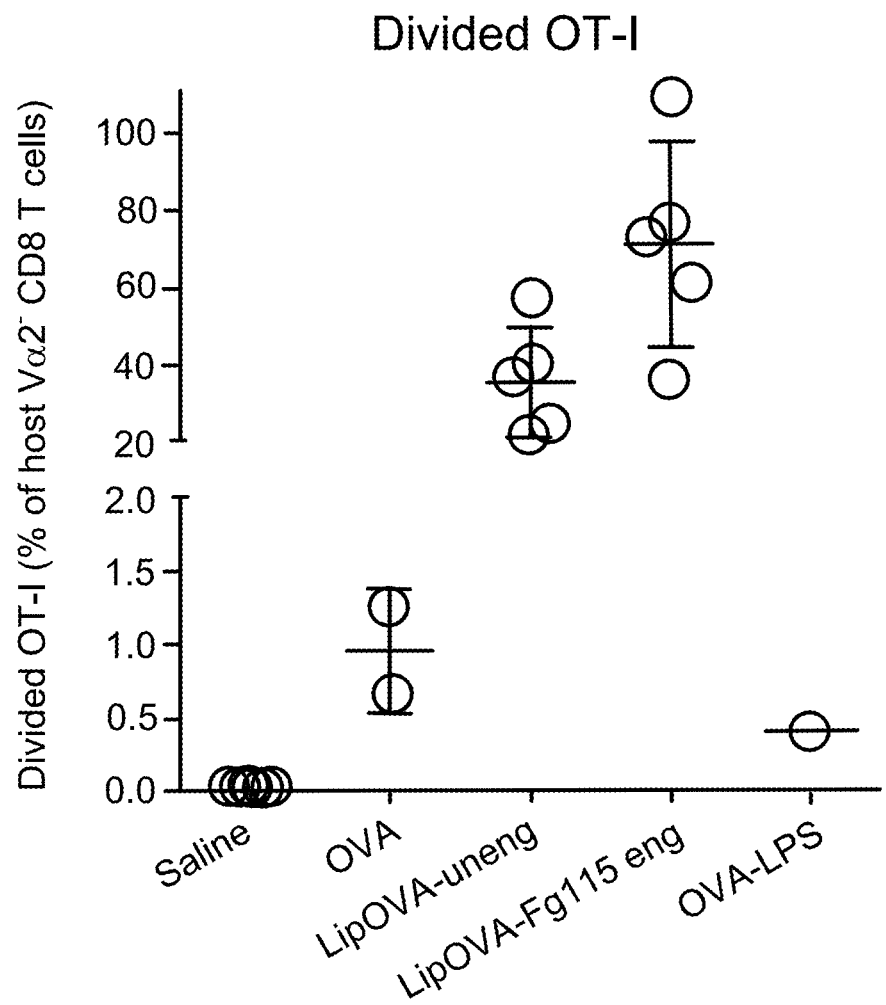
FIG. 6 shows CD8$^+$ T cell proliferation following immunisation of mice with liposomes loaded with OVA (LipOVA) and engrafted with Fgl15, and subsequent in vivo activation of the cellular response.

The results shown in FIG. 6 demonstrate that Fg115-engrafted liposomes induced the proliferation of CD8$^+$ T cells in vivo (division being assessed by CFSE dilution). Fg115-engrafted liposomes induced killing by effector T cells specific for the OVA peptide SIINFEKL and related peptides N6 (SIINFNKL), G4 (SIIGFEKL) and E1(EIINFEKL), but not the control peptide NP68, but at this level of protein cargo, unengrafted liposomes were also very effective at inducing killing (data not shown).

Example 27

Ability of Fg115 Engrafted Liposomes to Induce Antigen-specific T Cell-mediated Killing in Vivo To assess the ability of Fg115 engrafted liposomes to induce antigen-specific T cell-mediated killing in vivo, Fg115 engrafted and unengrafted LipOVA liposome were prepared as described above and shown in Tables 29 and 30.

TABLE 29

| Formulation | 0.25% 3NTADTDA, 67.25% DOPC, 30% DOPG, 2.5% DSPE-PEG750 |
|---|---|
| Encapsulation | 300 µg/mL OVA in saline |
| Extrusion | 0.2 µm, 5x at 40 C. |
| [OVA] post dialysis | 95.2 µg/mL |
| [Lipids] post dialysis | 25.64 mM |

TABLE 30

| | Final [OVA] | Final [lipid] | Final [Fg115] |
|---|---|---|---|
| Fg115-LipOVA | 50 µg/mL | 13.46 mM | 31.03 µg/mL |
| LipOVA | 50 µg/mL | 13.46 mM | 0 |
| OVA | 50 µg/mL | 0 | 0 |

OT-I CD8 T cells were transferred to mice 24 hours prior to immunisation. Mice were immunised with the formulations shown in above at 2.5 µg per mouse (0.673 mM lipid per 50 µL bolus, intramuscularly).

OVA-specific CD8$^+$ T cells were purified by negative selection from OT-I TCR-transgenic mice via magnetic MACS separation (Miltenybiotec) using anti-B220/anti-TER119 antibodies attached to Microbeads (Miltenybiotec). CD8$^+$ T cells (10$^6$ cells) were adoptively transferred into C57BL/6J host mice via i.v. injection into the lateral tail vein. After 24 hrs, host mice were then immunized in replicates of 5 mice per group with various liposome formulations that carried OVA as antigen, danger signals and/or various targeting motifs in a 50 µl bolus of saline injected i.m. After 6 days, a fluorescent target array (FTA) was generated using splenocytes from CD45.1$^+$C57BL/6J mice and comprised of target cells pulsed with different concentrations of several variant OVA MHC-I-binding peptides; 1-5×10$^6$ FTA cells were injected i.v. into host mice via the lateral tail vein. After 18 hr in host animals, FTA cells were assessed for death in spleen cells isolated from sacrificed host mice using antibody and Hoechst 33258 (to assess viability of cells) labeling and flowcytometry. % specific killing of FTA cells was assessed as described above.

It was observed that Fg115 engrafted liposomes effectively induce antigen-specific T cell-mediated killing in vivo (data not shown).

Example 28

Effect of OVA Levels on in Vivo OVA-specific Killing Following Immunization with Fg115 Engrafted Liposomes LipOVA formulations with varying levels of encapsulated OVA were prepared to assess the effect of OVA levels on in vivo OVA-specific killing. Briefly, LipOVA liposomes were prepared as shown in Table 31. The liposomes were engrafted with Fg115 or left unengrafted to produce the formulations set forth in Table 32.

TABLE 31

| LipOVA (1) | |
|---|---|
| Formulation | 0.25% 3NTADTDA, 67.25% POPC, 30% DOPG, 2.5% DSPE-PEG750 |
| Encapsulation/rehydration of lipid film | 250 mg/mL in saline (no Nickel) |
| extrusion | 5x 0.2 µm |
| [OVA] | 93.5 µg/mL |
| [Lipid] | 27.68 mM |
| LipOVA (2) | |
| Formulation | 0.25% 3 NTADTDA, 67.25% POPC, 30% DOPG, 2.5% DSPE-PEG750 |
| Encapsulation/rehydration of lipid film | 125 mg/mL in saline (no Nickel) |
| extrusion | 5x 0.2 µm |
| [OVA] | 56.6 µg/mL |
| [Lipid] | 28.25 mM |
| LipOVA (3) | |

TABLE 31-continued

| Formulation | |
|---|---|
| Encapsulation/rehydration of lipid film | 0.25% 3NTADTDA, 67.25% POPC, 30% DOPG, 2.5% DSPE-PEG750 |
| extrusion | 62.5 mg/mL in saline (no Nickel) |
| | 5x 0.2 µm |
| [OVA] | 34.5 µg/mL |
| [Lipid] | LipOVA (4) |

| Formulation | 0.25% 3NTADTDA, 67.25% POPC, 30% DOPG, 2.5% DSPE-PEG750 |
|---|---|
| Encapsulation/rehydration of lipid film | 31.25 mg/mL in saline (no Nickel) |
| extrusion | 5x 0.2 µm |
| [OVA] | 24.4 µg/mL |
| [Lipid] | 24.16 mM |
| | Lip NO OVA |

| Formulation | 0.25% 3 NTADTDA, 67.25% POPC, 30% DOPG, 2.5% DSPE-PEG750 |
|---|---|
| [OVA] | 0 µg/mL |
| [Lipid] | 30.44 mM |

TABLE 32

| Liposome | Final volume (µL) | mM Lipid | OVA µg/mL | Fg115 µg/mL | OVA (µg per mouse) |
|---|---|---|---|---|---|
| LipOVA (1)-Fg115 | 150 | 11.84 | 40.00 | 59.21 | 2 |
| LipOVA (1)-Unengrafted | 100 | 11.84 | 40.00 | 0 | 2 |
| LipOVA (2)-Fg115 | 150 | 11.84 | 23.73 | 59.21 | 1.19 |
| LipOVA(2)-unengrafted | 100 | 11.84 | 23.73 | 0 | 1.19 |
| LipOVA(3)-Fg115 | 150 | 11.84 | 13.63 | 59.21 | 0.68 |
| LipOVA(3)-Unengrafted | 100 | 11.84 | 13.63 | 0 | 0.68 |
| LipOVA(4)-Fg115 | 150 | 11.84 | 11.48 | 59.21 | 0.57 |
| LipOVA(4) unengrafted | 100 | 11.84 | 11.48 | 0 | 0.57 |
| Lip No OVA-Fg115 | 150 | 11.84 | 0.00 | 59.21 | 0.00 |
| Lip No OVA-unengrafted | 100 | 11.84 | 0 | 0 | 0.00 |

Figure 7:
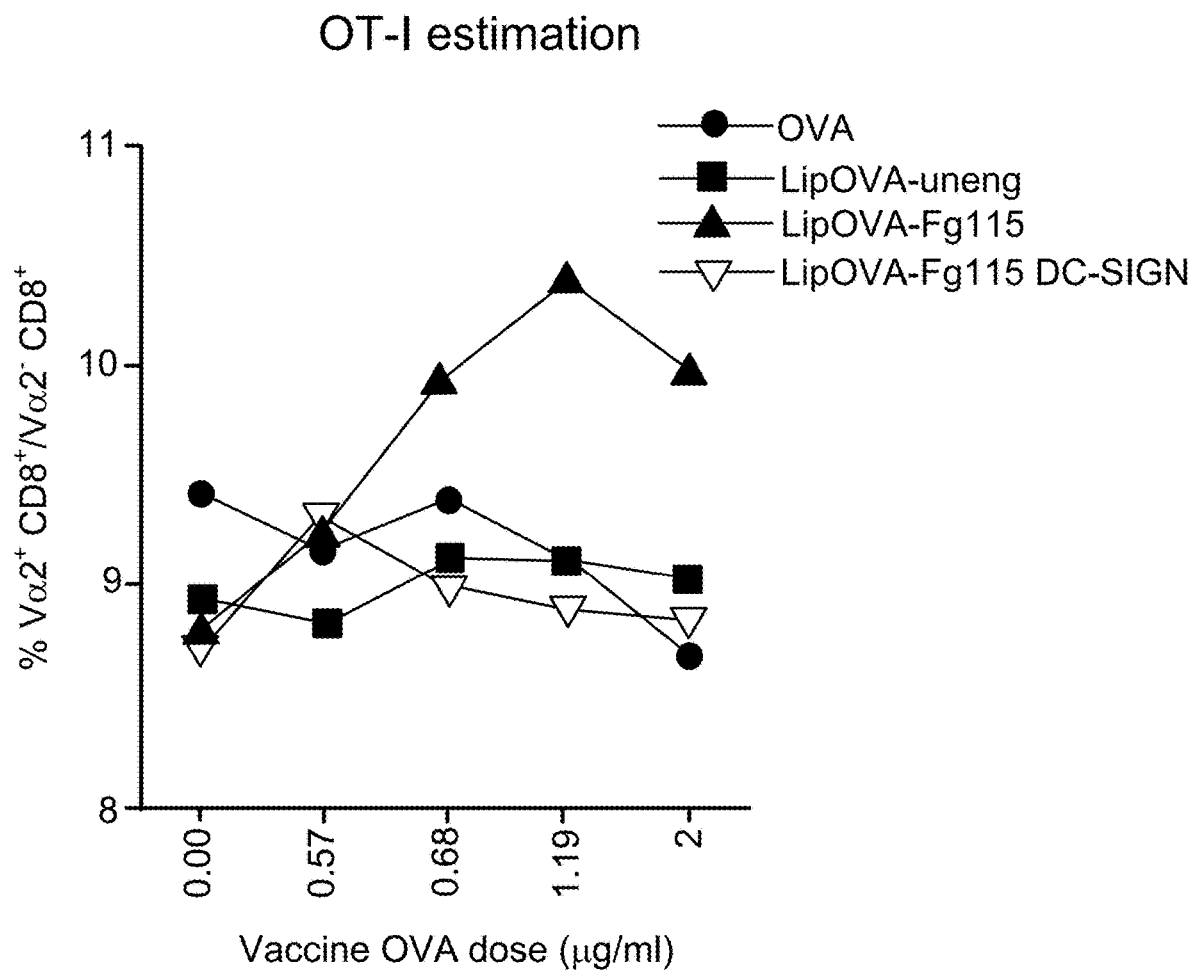
FIG. 7 shows CD8$^+$ T cell proliferation following immunisation of mice with liposomes engrafted with Fgl15 and loaded with varying amounts of OVA so that each mice received 0.57, 0.68, 1.19 or 2 μg OVA.

Mice were immunised with the liposome formulations and target specific killing was assessed as described above. Engrafted liposomes were able to induce improved cell proliferation, particularly at doses of 1.19 µg OVA (FIG. 7). When specific killing following pulsing of target cells with ovalbumin peptide SIINFEKL at various OVA doses was assessed (using cells from wild type mice), a clear increase in OVA-specific killing with Fg115-engrafted liposomes compared to unengrafted liposomes was observed when the amount of ovalbumin encapsulated in the liposomes was reduced (data not shown). The advantages of Fg155-engraftment were particularly apparent when mice were administered 0.57 µg OVA, with negligible antigen-specific killing observed using unengrafted liposomes compared to strong antigen-specific killing observed with Fg115-engrafted liposomes.

In addition to wild-type mice, a group of DC-SIGN transgenic mice were also immunized with the Fg115-engrafted OVA liposome formulations listed in Table 32. Higher level of antigen-specific killing (following pulsing of target cells with ovalbumin peptide SIINFEKL at 0.57 or 2 µg OVA doses, using CD11c+ cells from DC-SIGN transgenic mice or wild-type mice) was seen in the DC-SIGN transgenic mice than in the wild type mice at the lower dose (0.57 µg dose; data not shown). This improved killing in DC-SIGN transgenic mice was not evident at the higher dose. This suggests that whilst DC-SIGN targeting can augment Fg115 mediated responses, the advantage is most evident at the lower antigen dose.

Example 29

Polyclonal Response Elicited by Fg115 Engrafted Liposomes

To assess the polyclonal response, liposomes on a background of 67.25% POPC, 30% DOPG and 2.5% DSPE-PEG750, with 0.05% 3NTADTDA, loaded with OVA and engrafted with 110 µg/mL Fg115 or 55 µg/mL FliC were prepared as described above to produce LipOVA liposomes with 130 µg/mL OVA (22 mM, dose 1) or 300µg/mL, 22 mM dose 2). Mice (C57/B16 wild type mice) were immunised with the liposome formulations and target specific killing was assessed as described above. T helper responses were also assessed on the basis of CD69 upregulation on FTA (Fluorescent Target Array) B cells, which were pulsed with MHC-II-binding peptide epitopes, using antibody labeling and flow cytometry. Before sacrifice, mice were bleed via their retro-orbital sinus and serum isolated for measurement of circulating cytokines and antigen specific Ig by ELISA. In addition, % IFN-γ CD8+ T cells was assessed in spleen cells isolated from sacrificed host mice, after they were cultured for 6 hr in vitro with 10 µg/ml antigen peptide and Golgistop (BD bioscience), using intracellular cytokine staining (ICS) using antibody and labeling and flowcytometry.

Figure 8A:
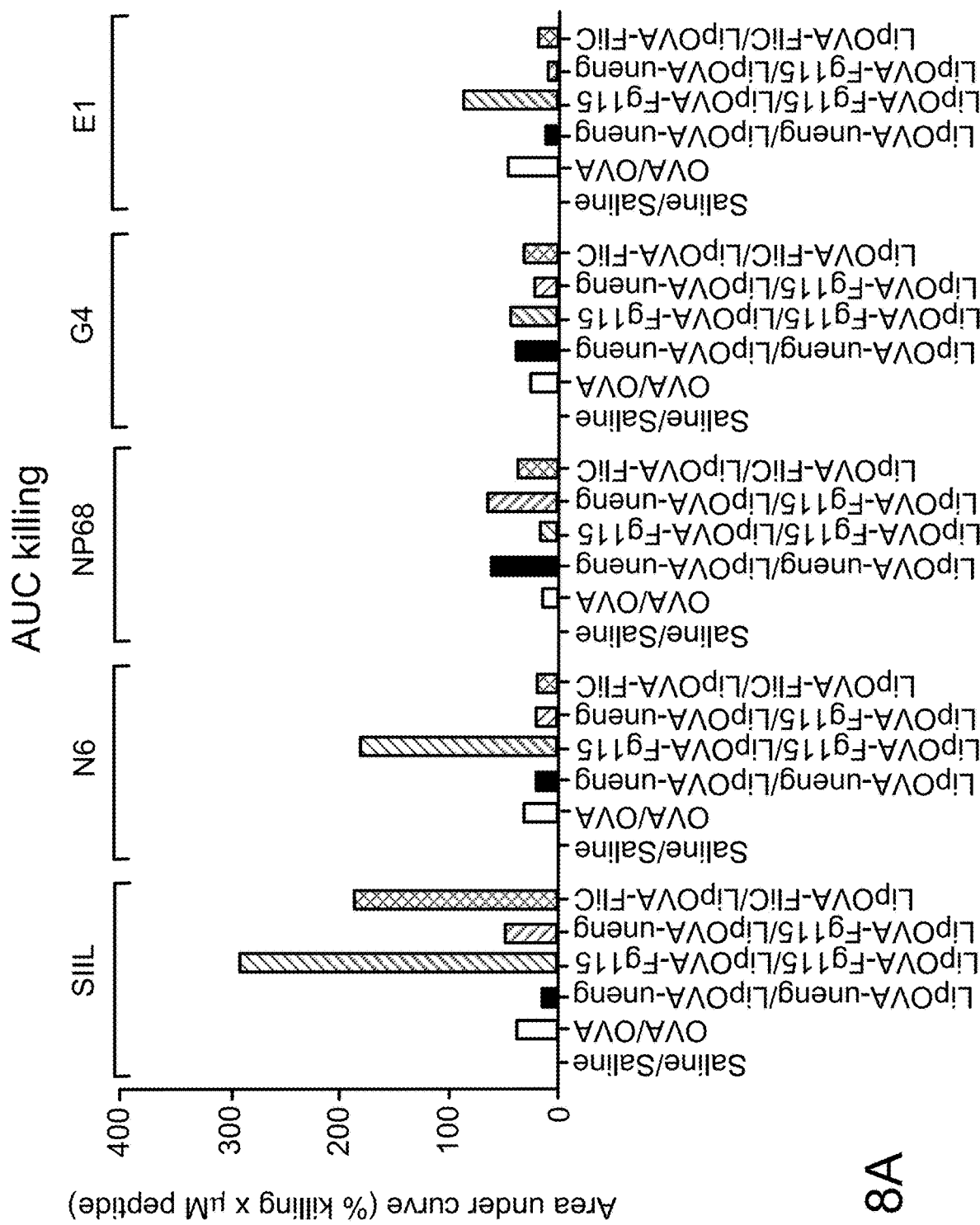
FIG. 8 shows the induction of immune responses following immunisation of mice with liposomes engrafted with Fgl15 or FliC and loaded with OVA. (A) Specific killing following pulsing of target cells with peptides, represented by Area Under the Curve (AUC) values. (B) IFN-γ CD8$^-$ T cells. (C) T helper cell response as represented by AUC.
Figure 8B:
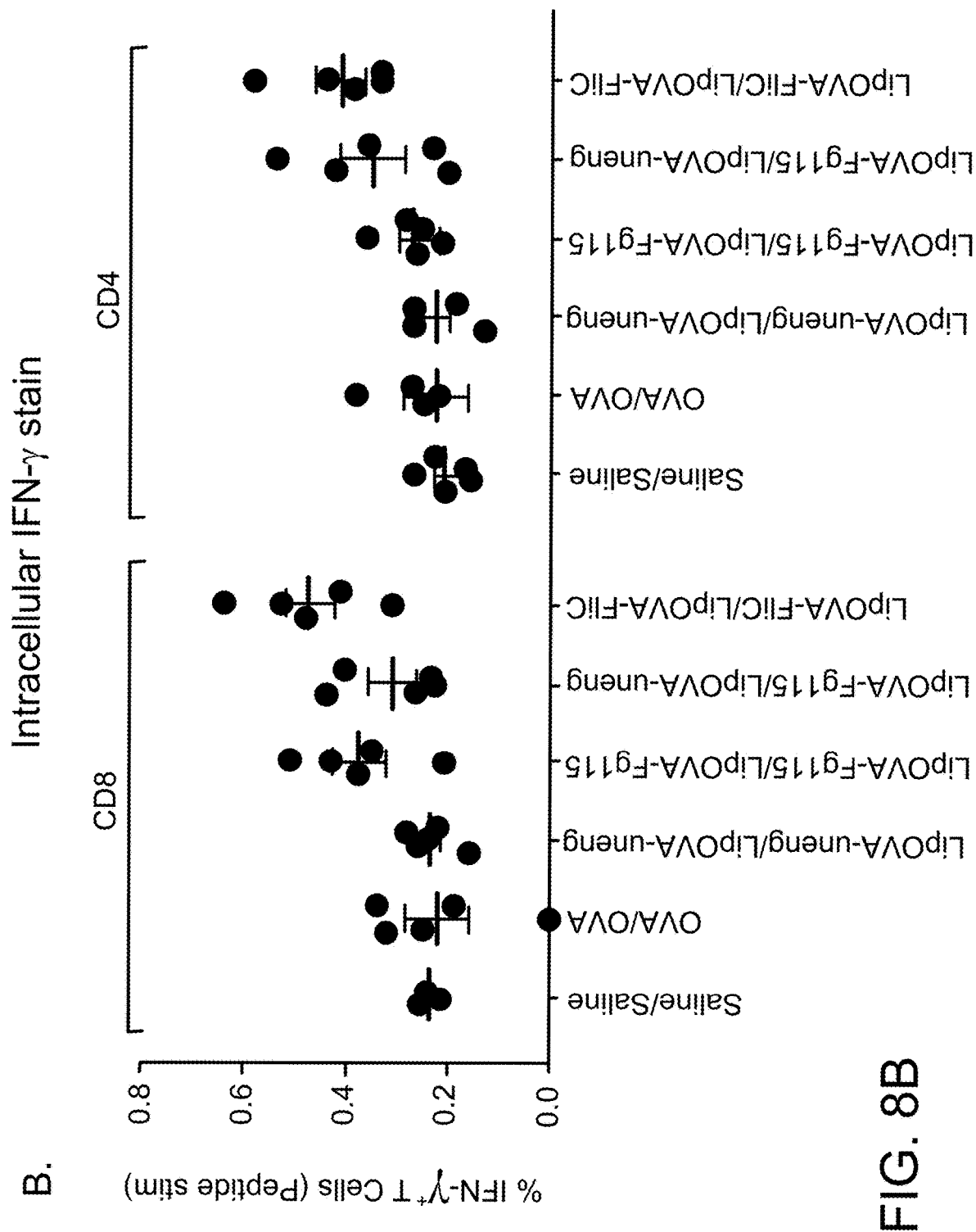
Figure 8C:
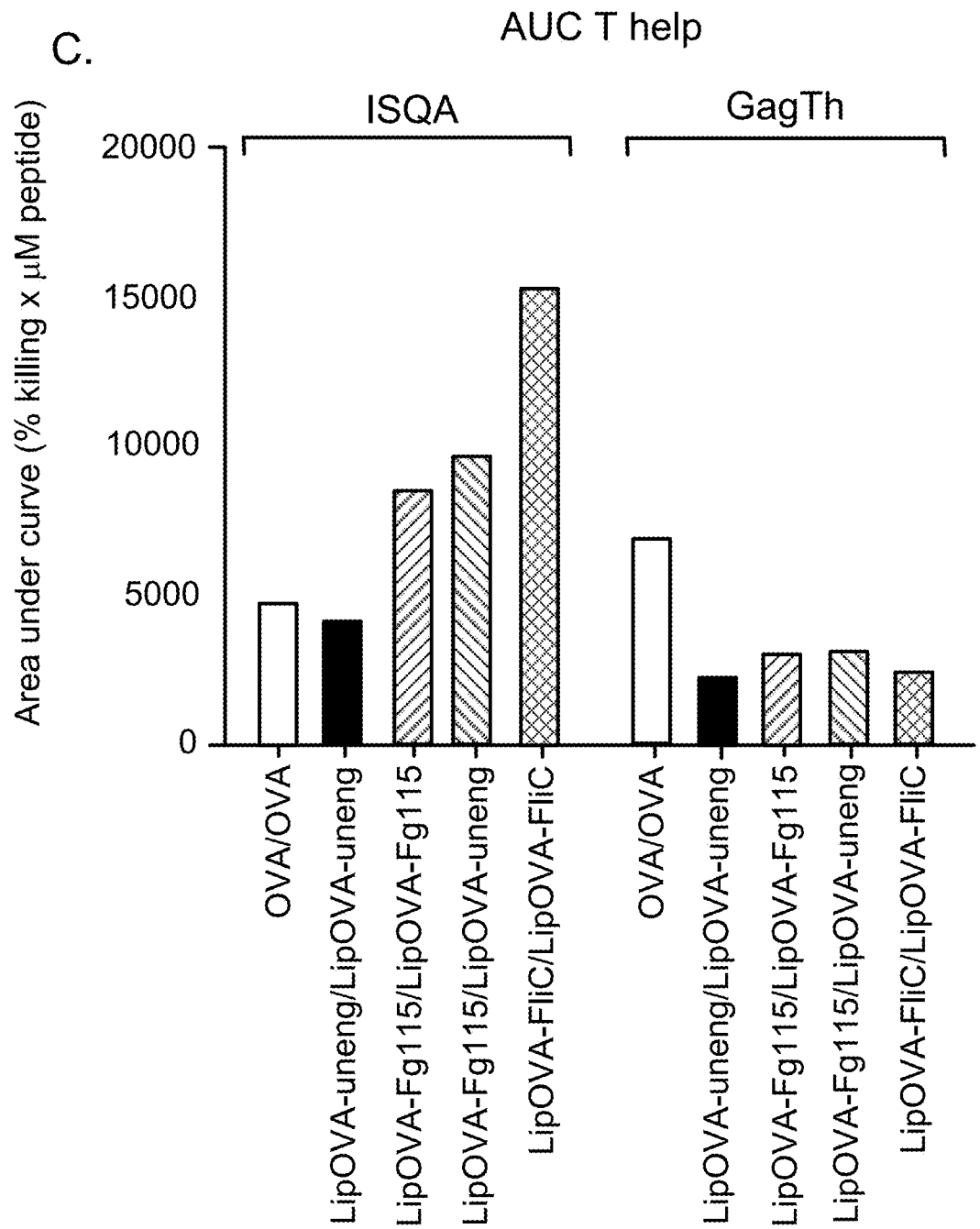

OVA-specific killing (SIIN and N6 peptide) was detected only in animals that had received a prime and boost of OVA liposomes engrafted either with Fg115 or FliC (FIG. 8A). When animals were immunized with unengrafted OVA liposomes, minimal killing was detected. When only the first dose was engrafted with Fg115, minimal killing was observed. Increased numbers of antigen-specific IFNγ-producing CD8+ T cells were detected when animals were immunized with OVA liposomes engrafted with either Fg115 or FliC (FIG. 8B). The frequency of antigen-specific IFNγ producing CD4+ T cells on the other hand was highest when OVA-liposomes were engrafted with FliC. The in vivo T helper response was assessed by measuring FTA B cell activation after 18 hr in vivo, indicating generation of T helper cells capable of cognate interaction with antigen-specific B cells. Mice that received LipOVA-Fg115/LipOVA-Fg115, LipOVA-Fg115/LipOVA-uneng and LipOVA-FliC/LipOVA-FliC vaccine regimes generated CD4 T helper cells capable of activating OVA-peptide-specific B cell responses. However, LipOVA-FliC/LipOVA-FliC overall generated a significantly better CD4 T helper response than the other vaccines. These trends are well summarised by measuring the area under each dose response curve (AUC), as shown in FIG. 8C.

The invention claimed is:

1. A chimeric protein, comprising a first polypeptide and a second polypeptide, wherein:
   the first polypeptide is a Toll Like Receptor 5 (TLR5) agonist, wherein the TLR5 agonist is a flagellin polypeptide that has at least 90% sequence identity to the sequence set forth in SEQ ID NO:3; and
   the second polypeptide has at least 90% sequence identity to the gp120 polypeptide set forth in SEQ ID NO:1 and at least 8 N-glycosylation sites.

2. The chimeric protein of claim 1, wherein the chimeric protein has at least 90% sequence identity to the polypeptide set forth in SEQ ID NO:5.

3. The chimeric protein of claim 1, wherein the chimeric protein is glycosylated.

4. A nanoparticulate carrier, comprising the chimeric protein of claim 1.

5. The nanoparticulate carrier of claim 4, comprising at least one additional TLR agonist.

6. The nanoparticulate carrier of claim 4, wherein the chimeric protein comprises a histidine tag and the nanoparticulate carrier comprises a nitrilotriacetic acid moiety, and the chimeric protein is attached to the nanoparticulate carrier via chelation between the histidine tag, the nitrilotriacetic acid moiety and a metal ion.

7. The nanoparticulate carrier of claim 6, wherein the nitrilotriacetic acid moiety is nitrilotriacetic acid (NTA) or trinitrilotriacetic acid (3NTA).

8. The nanoparticulate carrier of claim 4, wherein the nitrilotriacetic acid moiety is attached to ditetradecylamine (DTDA), Pam2Cys, or Pam3Cys.

9. The nanoparticulate carrier of claim 4, comprising nitrilotriacetic acid ditetradecylamine (NTA-DTDA), 3(nitrilotriacetic acid)-ditetradecylamine (3NTADTDA) or Pam2CysSerLys8Cys-3NTA.

10. The nanoparticulate carrier of claim 4, wherein the nanoparticulate carrier is selected from among a liposome, virosome, virus-like particle, archaeosome, plasma membrane vesicle, niosome, lipid core peptide, immunostimulating complex and polymer based nanoparticle.

11. The nanoparticulate carrier of claim 4, further comprising an antigen.

12. A method of eliciting an immune response to an antigen in a subject, the method comprising administering to the subject the nanoparticulate carrier of claim 11.

13. A method of internalizing an antigen in an antigen presenting cell, the method comprising contacting the antigen presenting cell with the nanoparticulate carrier of claim 11.

* * * * *

SEQUENCE LISTING

<160> NUMBER OF SEQ ID NOS: 12

<210> SEQ ID NO 1

<211> LENGTH: 509
<212> TYPE: PRT
<213> ORGANISM: HIV

<400> SEQUENCE: 1

```
Met Arg Val Lys Glu Lys Tyr Gln His Leu Trp Arg Trp Gly Trp Lys
 1               5                  10                  15

Trp Gly Thr Met Leu Leu Gly Ile Leu Met Ile Cys Ser Ala Thr Glu
             20                  25                  30

Lys Leu Trp Val Thr Val Tyr Tyr Gly Val Pro Val Trp Lys Glu Ala
         35                  40                  45

Thr Thr Thr Leu Phe Cys Ala Ser Asp Ala Lys Ala Tyr Asp Thr Glu
     50                  55                  60

Val His Asn Val Trp Ala Thr His Ala Cys Val Pro Thr Asp Pro Asn
 65                  70                  75                  80

Pro Gln Glu Val Val Leu Glu Asn Val Thr Glu Asn Phe Asn Met Trp
                 85                  90                  95

Lys Asn Asn Met Val Glu Gln Met His Glu Asp Ile Ile Ser Leu Trp
            100                 105                 110

Asp Gln Ser Leu Lys Pro Cys Val Lys Leu Thr Pro Leu Cys Val Thr
        115                 120                 125

Leu Asn Cys Thr Asp Leu Arg Asn Val Thr Asn Ile Asn Asn Ser Ser
    130                 135                 140

Glu Gly Met Arg Gly Glu Ile Lys Asn Cys Ser Phe Asn Ile Thr Thr
145                 150                 155                 160

Ser Ile Arg Asp Lys Val Lys Lys Asp Tyr Ala Leu Phe Tyr Arg Leu
                165                 170                 175

Asp Val Val Pro Ile Asp Asn Asp Asn Thr Ser Tyr Arg Leu Ile Asn
            180                 185                 190

Cys Asn Thr Ser Thr Ile Thr Gln Ala Cys Pro Lys Val Ser Phe Glu
        195                 200                 205

Pro Ile Pro Ile His Tyr Cys Thr Pro Ala Gly Phe Ala Ile Leu Lys
    210                 215                 220

Cys Lys Asp Lys Lys Phe Asn Gly Thr Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Val Val Ile Arg Ser Ser
            260                 265                 270

Asn Phe Thr Asp Asn Ala Lys Asn Ile Ile Val Gln Leu Lys Glu Ser
        275                 280                 285

Val Glu Ile Asn Cys Thr Arg Pro Asn Asn Asn Thr Arg Lys Ser Ile
    290                 295                 300

His Ile Gly Pro Gly Arg Ala Phe Tyr Thr Thr Gly Asp Ile Ile Gly
305                 310                 315                 320

Asp Ile Arg Gln Ala His Cys Asn Ile Ser Arg Thr Lys Trp Asn Asn
                325                 330                 335

Thr Leu Asn Gln Ile Ala Thr Lys Leu Lys Glu Gln Phe Gly Asn Asn
            340                 345                 350

Lys Thr Ile Val Phe Asn Gln Ser Gly Gly Asp Pro Glu Ile Val
        355                 360                 365

Met His Ser Phe Asn Cys Gly Gly Glu Phe Tyr Cys Asn Ser Thr
    370                 375                 380

Gln Leu Phe Asn Ser Thr Trp Asn Phe Asn Gly Thr Trp Asn Leu Thr
```

```
            385                 390                 395                 400
    Gln Ser Asn Gly Thr Glu Gly Asn Asp Thr Ile Thr Leu Pro Cys Arg
                    405                 410                 415
    Ile Lys Gln Ile Ile Asn Met Trp Gln Glu Val Gly Lys Ala Met Tyr
                    420                 425                 430
    Ala Pro Pro Ile Arg Gly Gln Ile Arg Cys Ser Ser Asn Ile Thr Gly
                    435                 440                 445
    Leu Ile Leu Thr Arg Asp Gly Gly Asn Asn His Asn Asn Asp Thr Glu
                    450                 455                 460
    Thr Phe Arg Pro Gly Gly Gly Asp Met Arg Asp Asn Trp Arg Ser Glu
    465                 470                 475                 480
    Leu Tyr Lys Tyr Lys Val Val Lys Ile Glu Pro Leu Gly Val Ala Pro
                    485                 490                 495
    Thr Lys Ala Lys Arg Arg Val Val Gln Arg Glu Lys Arg
                    500                 505

<210> SEQ ID NO 2
<211> LENGTH: 1527
<212> TYPE: DNA
<213> ORGANISM: HIV

<400> SEQUENCE: 2
atgagagtga aggagaagta tcagcacttg tggagatggg ggtggaaatg gggcaccatg      60
ctccttggga tattgatgat ctgtagtgct acagaaaaat tgtgggtcac agtctattat     120
ggggtacctg tgtggaaaga agcaaccacc actctatttt gtgcatcaga tgctaaagca     180
tatgatacag aggtacataa tgtttgggcc acacatgcct gtgtacccac agaccccaac     240
ccacaagaag tagtattgga aaatgtgaca gaaaatttta acatgtggaa aaataacatg     300
gtagaacaga tgcatgagga taataatcagt ttatgggatc aaagcctaaa gccatgtgta     360
aaattaaccc cactctgtgt tactttaaat tgcactgatt tgaggaatgt tactaatatc     420
aataatagta gtgagggaat gagaggagaa ataaaaaact gctctttcaa tatcaccaca     480
agcataagag ataaggtgaa gaaagactat gcactttttt atagacttga tgtagtacca     540
atagataatg ataatactag ctataggttg ataaattgta taccctcaac cattacacag     600
gcctgtccaa aggtatcctt tgagccaatt cccatacatt attgtaccccc ggctggtttt     660 gcgattctaa agtgtaaaga taagaagttc aatggaacag gccatgtaa aaatgtcagc     720 acagtacaat gtacacatgg aattaggcca gtagtgtcaa ctcaactgct gttaaatggc     780
agtctagcag aagaagaggt agtaattaga tctagtaatt tcacagacaa tgcaaaaaac     840
ataatagtac agttgaaaga atctgtagaa attaattgta caagacccaa caacaataca     900
aggaaaagta tacatatagg accaggaaga gcatttttata acaggagaa cataatagga     960 gatataagac aagcacattg caacattagt agaacaaaat ggaataacac tttaaatcaa    1020
atagctacaa aattaaaaga acaatttggg aataataaaa caatagtctt taatcaatcc    1080
tcaggagggg acccagaaat tgtaatgcac agttttaatt gtggagggga attttttctac    1140 tgtaattcaa cacaactgtt taatagtact tggaattttta atggtacttg gaatttaaca    1200
caatcgaatg gtactgaagg aaatgacact atcacactcc catgtagaat aaaacaaatt    1260
ataaacatgt ggcaagaagt aggaaaagca atgtatgccc ctcccatcag aggacaaatt    1320
agatgttcat caaatattac agggctgata ttaacaagag atggtggaaa taaccacaat    1380
aatgataccg agacctttag acctggagga ggagatatga gggacaattg gagaagtgaa    1440
```

```
ttatataaat ataaagtagt aaaaattgaa ccattaggag tagcacccac caaggcaaag    1500
agaagagtgg tgcagagaga aaaaaga                                        1527
```

<210> SEQ ID NO 3
<211> LENGTH: 495
<212> TYPE: PRT
<213> ORGANISM: Salmonella typhimurium

<400> SEQUENCE: 3

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
```

```
              355                 360                 365
Gly Lys Thr Glu Val Val Ser Ile Gly Gly Lys Thr Tyr Ala Ala Ser
            370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
                435                 440                 445

Ser Ala Arg Ser Arg Ile Glu Asp Ser Asp Tyr Ala Thr Glu Val Ser
        450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
                485                 490                 495

<210> SEQ ID NO 4
<211> LENGTH: 1485
<212> TYPE: DNA
<213> ORGANISM: Salmonella typhimurium

<400> SEQUENCE: 4
atggcacaag tcattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca ctcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tatcgatctg     480
aagcagatca actctcagac cctgggtctg gatacgctga atgtgcaaca aaaatataag     540
gtcagcgata cggctgcaac tgttacagga tatgccgata ctacgattgc tttagacaat     600
agtactttta aagcctcggc tactggtctt ggtggtactg accagaaaat tgatggcgat     660
ttaaaatttg atgatacgac tggaaaatat tacgccaaag ttaccgttac gggggggaact     720 ggtaaagatg gctattatga agtttccgtt gataagacga acggtgaggt gactcttgct     780
ggcggtgcga cttccccgct tacaggtgga ctacctgcga cagcaactga ggatgtgaaa     840
aatgtacaag ttgcaaatgc tgatttgaca gaggctaaag ccgcattgac agcagcaggt     900
gttaccggca cagcatctgt tgttaagatg tcttatactg ataataacgg taaaactatt     960
gatggtggtt tagcagttaa ggtaggcgat gattactatt ctgcaactca aaataaagat    1020
ggttccataa gtattaatac tacgaaatac actgcagatg acggtacatc caaaactgca    1080
ctaaacaaac tgggtggcgc agacggcaaa accgaagttg tttctattgg tgtaaaaact    1140
tacgctgcaa gtaaagccga aggtcacaac tttaaagcac agcctgatct ggcggaagcg    1200
gctgctacaa ccaccgaaaa cccgctgcag aaaattgatg ctgctttggc acaggttgac    1260
acgttacgtt ctgacctggg tgcggtacag aaccgtttca actccgctat taccaacctg    1320
ggcaacaccg taaacaacct gacttctgcc cgtagccgta tcgaagattc cgactacgcg    1380
```

```
accgaagttt ccaacatgtc tcgcgcgcag attctgcagc aggccggtac ctccgttctg    1440
gcgcaggcga accaggttcc gcaaaacgtc ctctctttac tgcgt                   1485
```

<210> SEQ ID NO 5
<211> LENGTH: 1018
<212> TYPE: PRT
<213> ORGANISM: Artificial sequence
<220> FEATURE:
<223> OTHER INFORMATION: Fg115

<400> SEQUENCE: 5

```
Met Ala Gln Val Ile Asn Thr Asn Ser Leu Ser Leu Leu Thr Gln Asn
  1               5                  10                  15

Asn Leu Asn Lys Ser Gln Ser Ala Leu Gly Thr Ala Ile Glu Arg Leu
                 20                  25                  30

Ser Ser Gly Leu Arg Ile Asn Ser Ala Lys Asp Asp Ala Ala Gly Gln
             35                  40                  45

Ala Ile Ala Asn Arg Phe Thr Ala Asn Ile Lys Gly Leu Thr Gln Ala
         50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Leu
        130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
```

-continued

```
                340                 345                 350
Asp Asp Gly Thr Ser Lys Thr Ala Leu Asn Lys Leu Gly Gly Ala Asp
                355                 360                 365
Gly Lys Thr Glu Val Val Ser Ile Gly Gly Lys Thr Tyr Ala Ala Ser
            370                 375                 380
Lys Ala Glu Gly His Asn Phe Lys Ala Gln Pro Asp Leu Ala Glu Ala
385                 390                 395                 400
Ala Ala Thr Thr Thr Glu Asn Pro Leu Gln Lys Ile Asp Ala Ala Leu
                405                 410                 415
Ala Gln Val Asp Thr Leu Arg Ser Asp Leu Gly Ala Val Gln Asn Arg
            420                 425                 430
Phe Asn Ser Ala Ile Thr Asn Leu Gly Asn Thr Val Asn Asn Leu Thr
            435                 440                 445
Ser Ala Arg Ser Arg Ile Glu Asp Ser Asp Tyr Ala Thr Glu Val Ser
    450                 455                 460
Asn Met Ser Arg Ala Gln Ile Leu Gln Gln Ala Gly Thr Ser Val Leu
465                 470                 475                 480
Ala Gln Ala Asn Gln Val Pro Gln Asn Val Leu Ser Leu Leu Arg Thr
                485                 490                 495
Ser Met Arg Val Lys Glu Lys Tyr Gln His Leu Trp Arg Trp Gly Trp
            500                 505                 510
Lys Trp Gly Thr Met Leu Leu Gly Ile Leu Met Ile Cys Ser Ala Thr
        515                 520                 525
Glu Lys Leu Trp Val Thr Val Tyr Tyr Gly Val Pro Val Trp Lys Glu
    530                 535                 540
Ala Thr Thr Thr Leu Phe Cys Ala Ser Asp Ala Lys Ala Tyr Asp Thr
545                 550                 555                 560
Glu Val His Asn Val Trp Ala Thr His Ala Cys Val Pro Thr Asp Pro
                565                 570                 575
Asn Pro Gln Glu Val Val Leu Glu Asn Val Thr Glu Asn Phe Asn Met
            580                 585                 590
Trp Lys Asn Asn Met Val Glu Gln Met His Glu Asp Ile Ile Ser Leu
        595                 600                 605
Trp Asp Gln Ser Leu Lys Pro Cys Val Lys Leu Thr Pro Leu Cys Val
    610                 615                 620
Thr Leu Asn Cys Thr Asp Leu Arg Asn Val Thr Asn Ile Asn Asn Ser
625                 630                 635                 640
Ser Glu Gly Met Arg Gly Glu Ile Lys Asn Cys Ser Phe Asn Ile Thr
                645                 650                 655
Thr Ser Ile Arg Asp Lys Val Lys Lys Asp Tyr Ala Leu Phe Tyr Arg
            660                 665                 670
Leu Asp Val Val Pro Ile Asp Asn Asp Asn Thr Ser Tyr Arg Leu Ile
        675                 680                 685
Asn Cys Asn Thr Ser Thr Ile Thr Gln Ala Cys Pro Lys Val Ser Phe
    690                 695                 700
Glu Pro Ile Pro Ile His Tyr Cys Thr Pro Ala Gly Phe Ala Ile Leu
705                 710                 715                 720
Lys Cys Lys Asp Lys Lys Phe Asn Gly Thr Gly Pro Cys Lys Asn Val
                725                 730                 735
Ser Thr Val Gln Cys Thr His Gly Ile Arg Pro Val Val Ser Thr Gln
            740                 745                 750
Leu Leu Leu Asn Gly Ser Leu Ala Glu Glu Val Val Ile Arg Ser
        755                 760                 765
```

Ser Asn Phe Thr Asp Asn Ala Lys Asn Ile Ile Val Gln Leu Lys Glu
    770                 775                 780

Ser Val Glu Ile Asn Cys Thr Arg Pro Asn Asn Thr Arg Lys Ser
785                 790                 795                 800

Ile His Ile Gly Pro Gly Arg Ala Phe Tyr Thr Thr Gly Asp Ile Ile
                805                 810                 815

Gly Asp Ile Arg Gln Ala His Cys Asn Ile Ser Arg Thr Lys Trp Asn
            820                 825                 830

Asn Thr Leu Asn Gln Ile Ala Thr Lys Leu Lys Glu Gln Phe Gly Asn
        835                 840                 845

Asn Lys Thr Ile Val Phe Asn Gln Ser Ser Gly Gly Asp Pro Glu Ile
    850                 855                 860

Val Met His Ser Phe Asn Cys Gly Gly Glu Phe Phe Tyr Cys Asn Ser
865                 870                 875                 880

Thr Gln Leu Phe Asn Ser Thr Trp Asn Phe Asn Gly Thr Trp Asn Leu
                885                 890                 895

Thr Gln Ser Asn Gly Thr Glu Gly Asn Asp Thr Ile Thr Leu Pro Cys
            900                 905                 910

Arg Ile Lys Gln Ile Ile Asn Met Trp Gln Glu Val Gly Lys Ala Met
        915                 920                 925

Tyr Ala Pro Pro Ile Arg Gly Gln Ile Arg Cys Ser Ser Asn Ile Thr
    930                 935                 940

Gly Leu Ile Leu Thr Arg Asp Gly Gly Asn Asn His Asn Asn Asp Thr
945                 950                 955                 960

Glu Thr Phe Arg Pro Gly Gly Gly Asp Met Arg Asp Asn Trp Arg Ser
                965                 970                 975

Glu Leu Tyr Lys Tyr Lys Val Val Lys Ile Glu Pro Leu Gly Val Ala
            980                 985                 990

Pro Thr Lys Ala Lys Arg Arg Val Val Gln Arg Glu Lys Arg Leu Val
        995                 1000                1005

Pro Arg Gly Ser His His His His His His
    1010                1015

<210> SEQ ID NO 6
<211> LENGTH: 3075
<212> TYPE: DNA
<213> ORGANISM: Artificial sequence
<220> FEATURE:
<223> OTHER INFORMATION: Fg115

<400> SEQUENCE: 6
ggatccatgg cacaagtcat taatacaaac agcctgtcgc tgttgaccca gaataacctg        60
aacaaatccc agtccgctct gggcaccgct atcgagcgtc tgtcttccgg tctgcgtatc       120
aacagcgcga agacgatgc ggcaggtcag gcgattgcta accgttttac cgcgaacatc       180
aaaggtctga ctcaggcttc ccgtaacgct aacgacggta tctccattgc gcagaccact       240
gaaggcgcgc tgaacgaaat caacaacaac ctgcagcgtg tgcgtgaact ggcggttcag       300
tctgctaaca gcaccaactc ccagtctgac ctcgactcca tccaggctga aatcacccag       360
cgcctgaacg aaatcgaccg tgtatccggc agactcagt tcaacggcgt gaaagtcctg        420
gcgcaggaca cacccctgac catccaggtt ggtgccaacg acggtgaaac tatcgatatc       480
gatctgaagc agatcaactc tcagaccctg gtctggata cgctgaatgt gcaacaaaaa        540
tataaggtca gcgatacggc tgcaactgtt acaggatatg ccgatactac gattgcttta       600

```
gacaatagta cttttaaagc ctcggctact ggtcttggtg gtactgacca gaaaattgat    660
ggcgatttaa aatttgatga tacgactgga aaatattacg ccaaagttac cgttacgggg    720
ggaactggta aagatggcta ttatgaagtt tccgttgata agacgaacgg tgaggtgact    780
cttgctggcg gtgcgacttc cccgcttaca ggtggactac ctgcgacagc aactgaggat    840
gtgaaaaatg tacaagttgc aaatgctgat ttgacagagg ctaaagccgc attgacagca    900
gcaggtgtta ccggcacagc atctgttgtt aagatgtctt atactgataa taacggtaaa    960
actattgatg gtggtttagc agttaaggta ggcgatgatt actattctgc aactcaaaat   1020
aaagatggtt ccataagtat taatactacg aaatacactg cagatgacgg tacatccaaa   1080
actgcactaa acaaactggg tggcgcagac ggcaaaaccg aagttgtttc tattggtggt   1140
aaaacttacg ctgcaagtaa agccgaaggt cacaaccttta aagcacagcc tgatctggcg   1200
gaagcggctg ctacaaccac cgaaaacccg ctgcagaaaa ttgatgctgc tttggcacag   1260
gttgacacgt tacgttctga cctgggtgcg gtacagaacc gtttcaactc cgctattacc   1320
aacctgggca acaccgtaaa caacctgact tctgcccgta ccgtatcga agattccgac    1380 tacgcgaccg aagtttccaa catgtctcgc gcgcagattc tgcagcaggc cggtacctcc   1440
gttctggcgc aggcgaacca ggttccgcaa aacgtcctct ctttactgcg tactagtatg   1500
agagtgaagg agaagtatca gcacttgtgg agatgggggt ggaaatgggg caccatgctc   1560
cttgggatat tgatgatctg tagtgctaca gaaaaattgt gggtcacagt ctattatggg   1620
gtacctgtgt ggaaagaagc aaccaccact ctattttgtg catcagatgc taaagcatat   1680
gatacagagg tacataatgt ttgggccaca catgcctgtg tacccacaga ccccaaccca   1740
caagaagtag tattggaaaa tgtgacagaa aattttaaca tgtggaaaaa taacatggta   1800
gaacagatgc atgaggatat aatcagttta tgggatcaaa gcctaaagcc atgtgtaaaa   1860
ttaaccccac tctgtgttac tttaaattgc actgatttga ggaatgttac taatatcaat   1920
aatagtagtg agggaatgag aggagaaata aaaaactgct cttttcaatat caccacaagc   1980 ataagagata aggtgaagaa agactatgca ctttttttata gacttgatgt agtaccaata   2040
gataatgata atactagcta taggttgata aattgtaata cctcaaccat tacacaggcc   2100
tgtccaaagg tatcctttga gccaattccc atacattatt gtaccccggc tggttttgcg   2160
attctaaagt gtaaagataa gaagttcaat ggaacagggc catgtaaaaa tgtcagcaca   2220
gtacaatgta cacatggaat taggccagta gtgtcaactc aactgctgtt aaatggcagt   2280
ctagcagaag aagaggtagt aattagatct agtaatttca cagacaatgc aaaaaacata   2340
atagtacagt tgaaagaatc tgtagaaatt aattgtacaa gacccaacaa caatacaagg   2400
aaaagtatac atataggacc aggaagagca ttttatacaa caggagacat aataggagat   2460
ataagacaag cacattgcaa cattagtaga acaaaatgga taacactttt aaatcaaata   2520
gctacaaaat taaagaaaca atttgggaat aataaaacaa tagtctttaa tcaatcctca   2580
ggaggggacc cagaaattgt aatgcacagt tttaattgtg gagggaatt tttctactgt   2640 aattcaacac aactgtttaa tagtacttgg aattttaatg gtacttggaa tttaacacaa   2700
tcgaatggta ctgaaggaaa tgacactatc acactcccat gtagaataaa acaaattata   2760
aacatgtggc aagaagtagg aaaagcaatg tatgcccctc ccatcagagg acaaattaga   2820
tgttcatcaa atattacagg gctgatatta acaagagatg gtggaaataa ccacaataat   2880
gataccgaga cctttagacc tggaggagga gatatgaggg acaattggag aagtgaatta   2940
tataaatata agtagtaaaa aattgaacca ttaggagtag cacccaccaa ggcaaagaga   3000
```

```
agagtggtgc agagagaaaa aagactggtt ccgcgtggat ctcaccatca ccatcaccat    3060
taagtaagcg gccgc                                                     3075
```

<210> SEQ ID NO 7
<211> LENGTH: 6
<212> TYPE: DNA
<213> ORGANISM: Artificial sequence
<220> FEATURE:
<223> OTHER INFORMATION: Linker

<400> SEQUENCE: 7

```
actagt                                                                  6
```

<210> SEQ ID NO 8
<211> LENGTH: 6
<212> TYPE: PRT
<213> ORGANISM: Artificial sequence
<220> FEATURE:
<223> OTHER INFORMATION: Thrombin cleavage sequence

<400> SEQUENCE: 8

```
Leu Val Pro Arg Gly Ser
1               5
```

<210> SEQ ID NO 9
<211> LENGTH: 18
<212> TYPE: DNA
<213> ORGANISM: Artificial sequence
<220> FEATURE:
<223> OTHER INFORMATION: Thrombin cleavage sequence

<400> SEQUENCE: 9

```
ctggttccgc gtggatct                                                    18
```

<210> SEQ ID NO 10
<211> LENGTH: 6
<212> TYPE: PRT
<213> ORGANISM: Artificial sequence
<220> FEATURE:
<223> OTHER INFORMATION: His(6) tag

<400> SEQUENCE: 10

```
His His His His His His
1               5
```

<210> SEQ ID NO 11
<211> LENGTH: 18
<212> TYPE: DNA
<213> ORGANISM: Artificial sequence
<220> FEATURE:
<223> OTHER INFORMATION: His(6) tag

<400> SEQUENCE: 11

```
caccatcacc atcaccat                                                    18
```

<210> SEQ ID NO 12
<211> LENGTH: 44
<212> TYPE: PRT
<213> ORGANISM: Artificial sequence
<220> FEATURE:
<223> OTHER INFORMATION: FlgT peptide

<400> SEQUENCE: 12

```
His His His His His His His His His His His Gly Ser Gly Ser
1               5                   10                  15
```

```
Gly Ile Asn Asn Asn Leu Gln Arg Val Arg Glu Leu Ala Val Gln Ser
            20                  25                  30

Ala Asn Ser Thr Asn Ser Gln Ser Asp Leu Asp Ser
            35                  40
```